US007316928B2

(12) United States Patent
Chapman et al.

(10) Patent No.: US 7,316,928 B2
(45) Date of Patent: Jan. 8, 2008

(54) PLANT FATTY ACID AMIDE HYDROLASES

(75) Inventors: Kent D. Chapman, Denton, TX (US); Rhidaya Shrestha, East Lansing, MI (US); Elison Blancaflor, Ardmore, OK (US); Richard A. Dixon, Ardmore, OK (US)

(73) Assignees: The University of North Texas, Denton, TX (US); The Samuel Roberts Noble Foundation, Ardmore, OK (US)

( * ) Notice: Subject to any disclaimer, the term of this patent is extended or adjusted under 35 U.S.C. 154(b) by 148 days.

(21) Appl. No.: 10/862,063

(22) Filed: Jun. 4, 2004

(65) Prior Publication Data

US 2005/0028233 A1    Feb. 3, 2005

Related U.S. Application Data

(60) Provisional application No. 60/475,628, filed on Jun. 4, 2003.

(51) Int. Cl.
 *C12N 15/82* (2006.01)
 *C12N 5/14* (2006.01)
 *C12N 15/63* (2006.01)
 *C07H 21/04* (2006.01)
 *A01N 5/00* (2006.01)

(52) U.S. Cl. ............... 435/468; 435/320.1; 435/419; 435/69.1; 536/23.2; 800/281; 800/295; 800/260; 800/278

(58) Field of Classification Search ............... None
See application file for complete search history.

(56) References Cited

FOREIGN PATENT DOCUMENTS

WO    WO 00/73745    12/2000

OTHER PUBLICATIONS

Elomaa et al. (Molecular Breeding, 2:41-50, 1996).*
Colliver et al. (Plant molecular Biology, 35:509-522, 1997).*
Tripathy et al. (Plant Physiology, 121:1299-1308, 1999).*
Chapman et al., (Plant Physiology, 120:1157-1164, 1999; p. 1163).*
Keskin et al. (Protein Science, 13:1043-1055, 2004).*
Chang et al. (NCBI, GenBank, Accession No: AF223949, pp. 1-2, Published Jun. 2, 2000).*
Hiei et al. (The Plant Journal, 6:271-282, 1994).*
Valvekens et al. (PNAS, 85:5536-5540, 1988).*
Maniatis et al., Molecular Cloning: A Laboratory Manual, Cold Spring Harbor Laboratory (1982).*
Altschul et al., "Gtapped BLAST and PSI-BLAST: a new generation of protein database search programs," *Nucleic Acids Research*, 25(17):3389-3402, 1997.
Blancaflor et al., "Elevated levels of N-lauroylethanolamine, a endogenous constituent of desiccated seeds, disrupt normal root development in Arabidopsis thaliana seedlins," *Planta*, 217(2):206-217, 2003.

Bracey et al., "Structural adaptations in a membrane enzyme that terminates endocannabinoid signaling," *Science*, 298:1793-1796, 2002.
Chang and Abelson, "Identification of a putative amidase gene in yeast *Saccharomyces cerevisiae*," *Nucleic Acids Research*, 18(23):7180, 1990.
Chapman et al., "N-acylethanolamines in seeds. Quantification of molecular species and their degradation upon imbibition," *Plant Physiol.*, 120:1157-1164, 1999.
Chapman, "Emerging physiological roles for N-acylphosphatidylethanolamine metabolism in plants: signal transduction and membrane protection," *Chem. Phys. Lipids*, 108:221-230, 2000.
Chebrou et al., "Study of the amidase signature group," *Biochim. Biophys. Acta*, 1298:285-293, 1996.
Cravatt and Lichtman, "The enzymatic inactivation of the fatty acid amide class of signaling lipids," *Chem. Phys. Lipids*, 121:135-148, 2002.
Cravatt et al., "Molecular characterization of an enzyme that degrades neuromodulatory fatty-acid amides," *Nature*, 384:83-87, 1996.
Curnow et al., "Glu-tRNA$^{Gln}$ amidotransferase: a novel heterotrimeric enzyme required for correct decoding of glutamine codons during translation," *Proc. Natl. Acad. Sci., USA*, 94:11819-11826, 1997.
Deutsch et al., "Methyl arachidonyl fluorophosphonate: a potent irreversible inhibitor of anadamide amidase," *Biochem. Pharmacol.*, 53:255-260, 1999.
GenBank Accession No. AB027132.
GenBank Accession No. U72497.
GenBank Accession No. U82535.
GenBank Accession No. U82536.
Genomic Sequence At5g64440.
Giang and Cravatt, "Molecular characterization of human and mouse fatty acid amide hydrolases," *Proc. Natl. Acad. Sci., USA*, 94:2238-2242, 1997.
Hashimoto et al., "Cloning and characterization of an amidase gene from Rhodococcus species N-774 and its expression in *Escherichia coli*," *Biochim. Biophys. Acta*, 1088:225-233, 1991.
Lambert et al., "The palmitoylethanolamide family: a new class of anti-inflammatory agnes?" *Current Med. Chem.*, 9:739-755, 2002.
Mayaux et al., "Purification, cloning and primary structure of an Enantiomer-selective amidase from Brevibacterium sp. Strain R312: structural evidence for genetic coupling with nitrile hydratase," *J. Bacteriol.*, 172:6764-6773, 1990.
Patricelli and Cravatt, "Clarifying the catalytic roles of conserved residues in the amidase signature family," *J. Biol. Chem.*, 275(25):19177-19184, 2000.
Patricelli et al., "Chemical and mutagenic investigations of fatty acid amide hydrolase: evidence for a family of serine hydrolases with distinct catalytic properties," *Biochemistry*, 38:9804-9812, 1999.

(Continued)

*Primary Examiner*—Phuong T Bui
*Assistant Examiner*—Vinod Kumar

(57) ABSTRACT

The invention provides plant fatty acid amide hydrolase (FAAH) coding sequences. Also provided are constructs comprising these sequences, plants transformed therewith and methods of use thereof. The invention allows the modification of plants for FAAH activity and N-Acylethanolamine levels. Such modification may be used to produce plants that are improved with respect to growth, seed germination, pathogen response and stress tolerance.

30 Claims, 22 Drawing Sheets

OTHER PUBLICATIONS

Schmid and Berdyshev, "Cannabinoid receptor-inactive N-acylethanolamines and other fatty acid amides: metabolism and function," *Prostag. Leukotr. Essent. Fatty Acids*, 66:363-376, 2002.

Schmid et al., "N-acylated glycerophospholipids and their derivatives," *Prog. Lipid Res.*, 29:1-43, 1990.

Schmid et al., "The N-acylation-phosphodiesterase pathway and cell signalling," *Chem. Phys. Lipids*, 80:133-142, 1996.

Schmid et al., "Cell signaling by endocannabinoids and their congeners: questions of selectivity and other challenges," *Chem. Phys. Lipids*, 121:111-134, 2002.

Shrestha et al., "Molecular identification of a functional homologue of the mammalian fatty acid amide hydrolase in Arabidopsis thaliana," *J. Biol. Chem.*, 278:34990-34997, 2003.

Shrestha et al., "N-acylethanolamines are metabolized by lipoxygenase and amidohydrolase in competing pathways during cottonseed imbibition," *Plant Physiol.*, 130:391-401, 2002.

TC identifier AW695697.
TC identifier TC111212.
TC identifier TC117552.
TC identifier TC132131.
TC identifier TC150217.
TC identifier TC18099.
TC identifier TC188324.
TC identifier TC199488.
TC identifier TC210025.
TC identifier TC21641.
TC identifier TC230081.
TC identifier TC242273.
TC identifier TC36243.
TC identifier TC76474.
TC identifier TC87636.

Tripathy et al., "N-acylethanolamine signaling in tobacco is mediated by a membrane-associated, high-affinity binding protein," *Plant Physiol.*, 131:1781-1791, 2003.

Tsuchiya et al., "High homology between 6-aminohexanoate-cyclic-dimer hydrolases of Flavobacterium and Pseudomonas strains," *J. Bacteriol.*, 171(6):3187-3191, 1989.

Ueda et al., "The fatty acid amide hydrolase (FAAH)," *Chem. Phys. Lipids*, 108:107-121, 2000.

Ueda et al., "Endocannabinoid hydrolases," *Prostaglandis Other Lipid Mediators*, 68-69:521-534, 2002.

Wilson and Nicoll, "Endocannabinoid signaling in the brain," *Science*, 296:678-682, 2002.

Adachi et al., "Oryza sativa (japonica cultivar-group) cDNA clone:J033061L19, full insert sequence," Database EMBL, Database Accession No. AK101740, 2003.

Feng et al., "Sequence and analysis of rice chromosome 4," Database EMBL, Database Accession No. Q7XTB3, 2003.

Kikuchi et al., "Collection, Mapping, and Annotation of over 28,000 cDNA clones from japonica rice," *Science*, 301:376-379, 2003.

Shrestha, "N-acyelthanolamine metabolism during cotton (Goddypium Hirsutum L.) seed imbibition," *J. Annual Meetings Am. Soc. Plant Biol. Canadian Soc. Plant Physiol.*, Abstract No. 480, 2001.

\* cited by examiner

A

```
Rat          ------------------------------------------------------------
Arabidopsis  MGKYQVMKRASEVDLSTVKYKAETMKAPHLTGLSFKLFVNLLEAPLIGSLIVDYLKKDNG  60

Rat          -------MVLSEVWTTLSGVSGVCLACSLLSAAVVLRWTGRQKARGAATRARQKQRASLE  53
Arabidopsis  MTKIFRNTVIPEEPMFRPEFPSQEPEHDVVIVGEDESPIDRLETALKCLPQYDPSRSLHA 120

Rat          TMDKAVQRFRLQNPDLDSEALLTLPLLQLVQKLQSGELSPEAVFFTYLGKAWEVNKGTNC 113
Arabidopsis  DPVSSFRYWKIRDYAYAYRSKLTTPLQVAKRIIS----IIEEFGYDKPPTPFLIRFDANE 176
                                               ↓
Rat          VTSYLTDCETQLSQAPRQGLLYGVPVSLKECFSYKGHDSTLG-LSLNEGMPSESDCVVVQ 172
Arabidopsis  VIKQAEASTRRFEQGNPISVLDGIFVTIKDDIDCLPHPTNGGTTWLHEDRSVEKDSAVVS 236
                                                        ↓↓
Rat          VLKLQGAVPFVHTNVPQSMLSFDCSNPLFGQTMNPWKSSKSPGGSSGGEGALIGSGGSPL 232
Arabidopsis  KLRSCGAILLGKANMHELGMGTTGNNSNYGTTRNPHDPKRYTGGSSSGSAAIVAAGLCSA 296
                                 ↓↓
Rat          GLGTDIGGSIRFPSAFCGICGLKPTGNRLSKSGLKGCVYGQTAVQLSLGPMARDVESLAL 292
Arabidopsis  ALGTDGGGSVRIPSALCGITGLKTT---YGRTDMTGSLCEGGTVEIIG-PLASSLEDAFL 352

Rat          CLKALLCEHLFTLDPTVPPLPFREEVYRSSRPLRVGYYETDNYTMPSPAMRRALIETKQR 352
Arabidopsis  VYAAILGSSSADRYNLKPSPPCFPKLLSHNGSNAIGSLRLGKYTKWFNDVS------SSD 406

Rat          LEAAGHTLIPFLPNNIPYALEVLSAGGLFSDGGRSFLQNFKGDFVDPCLGDLILILRLPS 412
Arabidopsis  ISDKCEDILKLLSNNHGCKVVEIVVPELEEMRAAHVISIGSPTLSSLTPYCEAGKNSKLS 466

Rat          WFKRLLSLLLKPLFPRLAAFLNSMRPRSAEKLWKLQHEIEMYRQSVIAQWKAMNLDVLLT 472
Arabidopsis  YDTRTSFAIFRSFSASDYIAAQCLRRR------LMEYHLNIFKDVDVIVTPTTGMTAPVI 520

Rat          PMLGPALDLNTPGRATGAISYTVLYNCLDFPAGVVPVTTVTAEDDAQMELYKGYFGDIWD 532
Arabidopsis  PPDALKNGETNIQVTTDLMRFVLAANLLGFPAISVPVG---------------------- 558

Rat          IILKKAMKNSVGLPVAVQCVALPWQEELCLRFMREVEQLMTPQ-KQPS--------- 579
Arabidopsis  -------YDKEGLPIGLQIMGRPWAEATVLGLAAAVEELAPVT-KKPAIFYDILNTN 607
```

B

```
              215                                          257    Identities   Positive
1 Mouse     GGSSGGEGALIGSGG SPLGLGTDIGGSIRF PSAFCGICGLKPT    25/43 (58%)  31/43 (72%)
2 Porcine   GGSSGGEGALIAAGG SPLGLGTDIGGSIRF PSAFCGICGIKPT    26/43 (60%)  30/43 (69%)
3 Rat       GGSSGGEGALIGSGG SPLGLGTDIGGSIRF PSAFCGICGLKPT    25/43 (58%)  31/43 (72%)
4 Human     GGSSGGEGALIGSGG SPLGLGTDIGGSIRF PSSFCGICGLKPT    24/43 (56%)  32/43 (74%)
              279                                          321
5 At        GGSSSGSAAIVAAGL CSAALGTDGGGSVRI PSALCGITGLKTT
```

C

```
           CCCCHHHHHHHHHCCCHHHCCCCCCCHHCHHHHHCCCEECCCC
Rat        GGSSGGEGALIGSGGSPLGLGTDIGGSIRFPSAFCGICGLKPT

CCCCHHHHHHHHHCCHHHCCCCCCCCCCCHHHHCCCEECCCC
At         GGSSSGSAAIVAAGLCSAALGTDGGGSVRIPSALCGITGLKTT
```

FIG. 2A–C

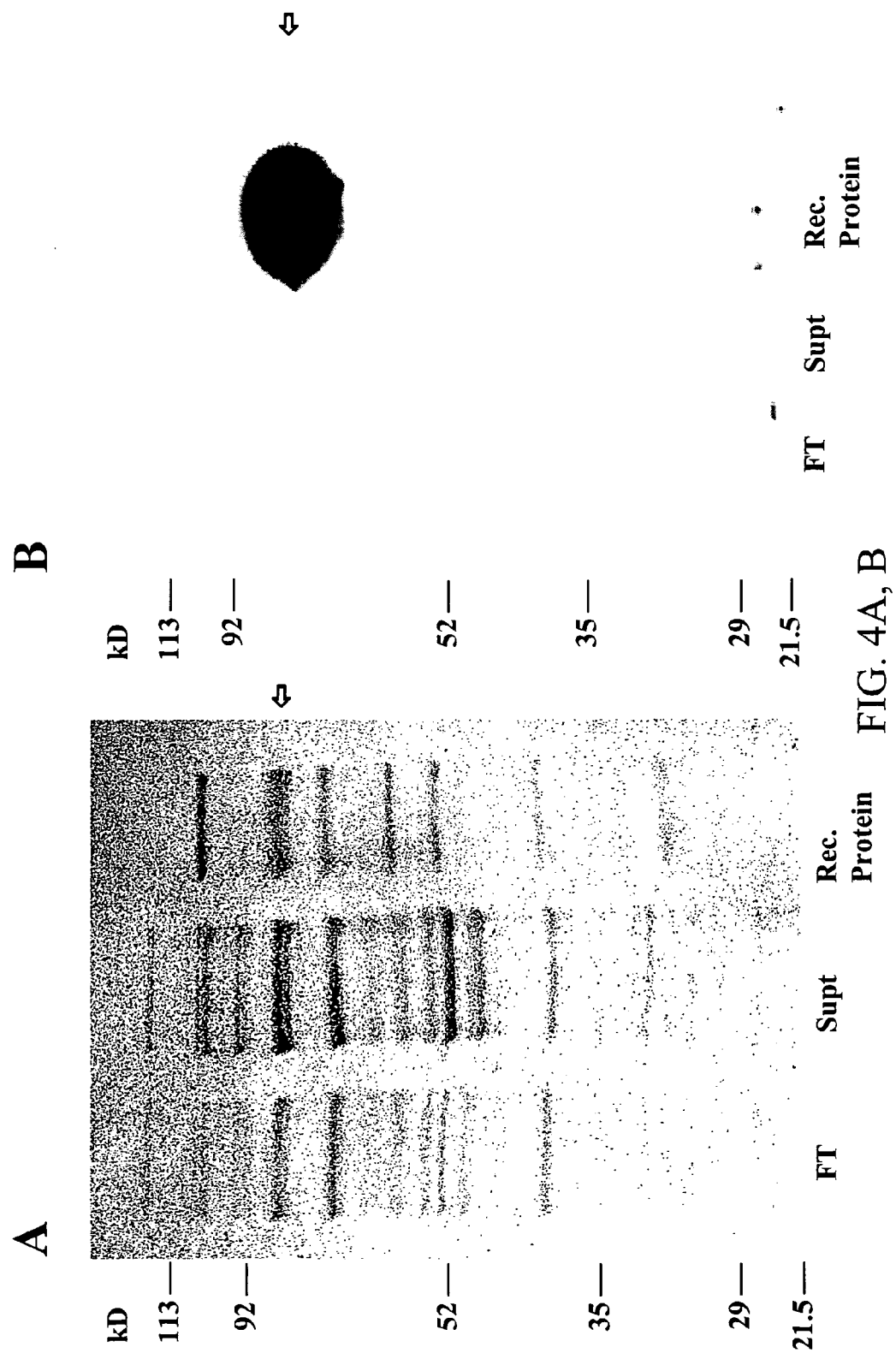
FIG. 4A, B

A
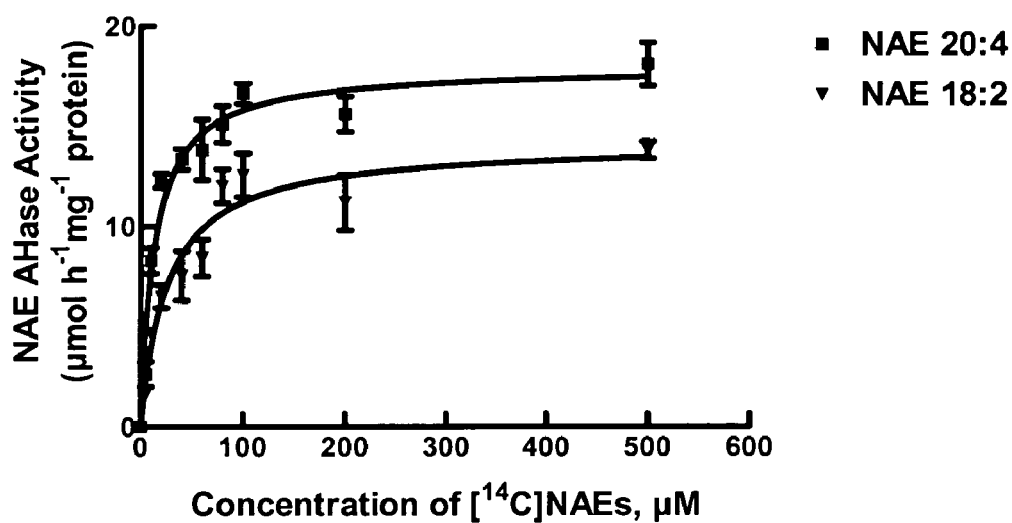
B
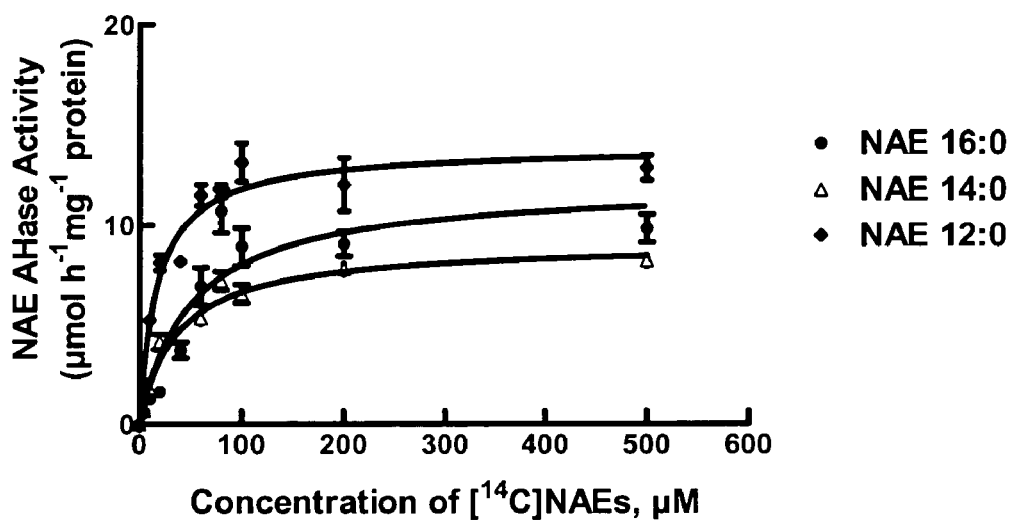
FIG. 5

```
At    1   MGKYQVMKRASEVDLSTVKYKAETMKAPHLTGLSFKLFVNLLEAPLIGSLIVDYLKKDNG
Mt    1   MGKKRVMVPAKDVDLSSIKYEPEIVQAPHLTGFWPRFFVRLIEAPLIGPFLLTMLKKENK
Os    1   ------MTPVEEVDLSAVRYQSPSLQAPHLTGPSLRAFVWLMESPLFGRLLTSVLKSQNN

At    61  MTKIFRNTVIPEEPMPRPEFPSQEPEHDVVIVGEDESPIDRLETALKCLPQYDPSRSLHA
Mt    61  IDQLLRNTVFPEEPMPKPEYPPQEKEHSVVELDEDGRPEGRVESALNCLPHYDP-AKLWE
Os    55  ITRMLQDTVIPERPMYLPEYPPQEPEQGVLLLGDDRDPVDRVEEALHCLPPYDPSLRWPA

At    121 DPVSSFRYWKIRDYAYAYRSKLTTPLQVAKRIISIIEEFGYDKPPTPFLIRFDANEVIKQ
Mt    120 NSSATFRYWKIRDYAYAYQSRKVTPSMVAESIISMIEENGIDKPPTPLLLSFDAAEVRKQ
Os    115 GDKPPFLYWKIRDFAHAYRSGITTPSVVAEHIIAGVEEWSNKKPPMPMLVYFNADDLRKQ

At    181 AEASTRRFEQGNPISVLDGIPVTIKDDIDCLPHPTNGGTTWLHEDRSVEKDSAVVSKLRS
Mt    180 AAASTQRFESGNPLSILDGIFIAIKDDIDCHPHPSTGGSTWMHEVRDVKKDAVCVSRLRS
Os    175 AEASTKRFQQGNPISILDGIFIAIKDDIDCFPYPSKGATTFFDKIRSVEKDAVCVARLRK

At    241 CGAILLGKANMHELGMGTTGNNSNYGTTRNPHDPKRYTGGSSSGSAAIVAAGLCSAALGT
Mt    240 CGVIFIGKTNMHEFGMGTTGNNSNYGTARNPHAPDRYTGGSSSGPAAIVASGLCSAALGT
Os    235 CGVLFIGKANMHELGLGVTGNNPNYGTARNPHSTDRYTGGSSSGPAALVSSGLCSAAIGT

At    301 DGGGSVRIPSALCGITGLKTTYGRTDMTGSLCEGGTVEIIGPLASSLEDAPLVYAAILGS
Mt    300 DGGSSVRIPSSLCGVVGLKINYGRTSMEGSLCDSGTVEVIGPIASTVEDAMLVYAAMLGA
Os    295 DGGGSVRIPSSLCGIIGLKTTYGRTDMTGALCDCGTVEVASPLAASVEDALLVYSAIAGS

At    361 SSADRYNLKPSPPCFPKLLSHNGSNAIGSLRLGKYTKWFNDVSSSDISDKCEDILKLLSN
Mt    360 SPANRISMKPSTPCLPTLSSDDDTDALRSLRIGIYTPWFNNVHSTEVSDKCEDALNLLSK
Os    355 RPMDKLTLRPSPLCVPNLVSPDNNNILGSVKIGKYTEWPHDVSDRDISNTCEDALNLLCS

At    421 NHGCKVVEIVVPELEEMRAAHVISIGSPTLSSLTPYCEAGKNSKLSYDTRTSFAIFRSFS
Mt    420 AHGCEVVEVVIPEIVEMRTAHLVSIGSECLSSLNPDIEDGKGVKLSYDTRTSLALFQSFT
Os    415 SFGCQIEEIILPELEEMRTAHVVSIGTESFCDLNPHYRAGKRTEFTLDTRTSLALFGSFT

At    481 ASDYIAAQCLRRRLMEYHLNIPKDVDVIVTPTTGMTAPVIPPDALKNGETNIQVTTDLMR
Mt    480 AADYVAAQCIRRRIMHYFMEIPKKVDVIVTPTTGMTAPRIPPSALKSGETDMPTTGYLMR
Os    475 STDYVASQRIRRRIMYYHNEAPKKVDVIATPTTGITAPEIPQSSLKLGESNYVVSAYLMR

At    541 FVLAANLLGFPAISVPVGYDKEGLPIGLQIMGRPWAEATVLGLAAAVEELAP-VTKKPAI
Mt    540 FVVPANLLGLPAISVPVGYDKEGLPIGLQVIGRPWAEATILRVAAAVEKLCGESKRRPVT
Os    535 FVIAGNLLGLPAITVPVGHDKQGLPIGLQLIGRPWGEASLLRVASAIEELCLQKRKRPSA

At    600 FYDILNTN
Mt    600 YYDVLGAN
Os    595 FHDILNA-
```

FIG. 6

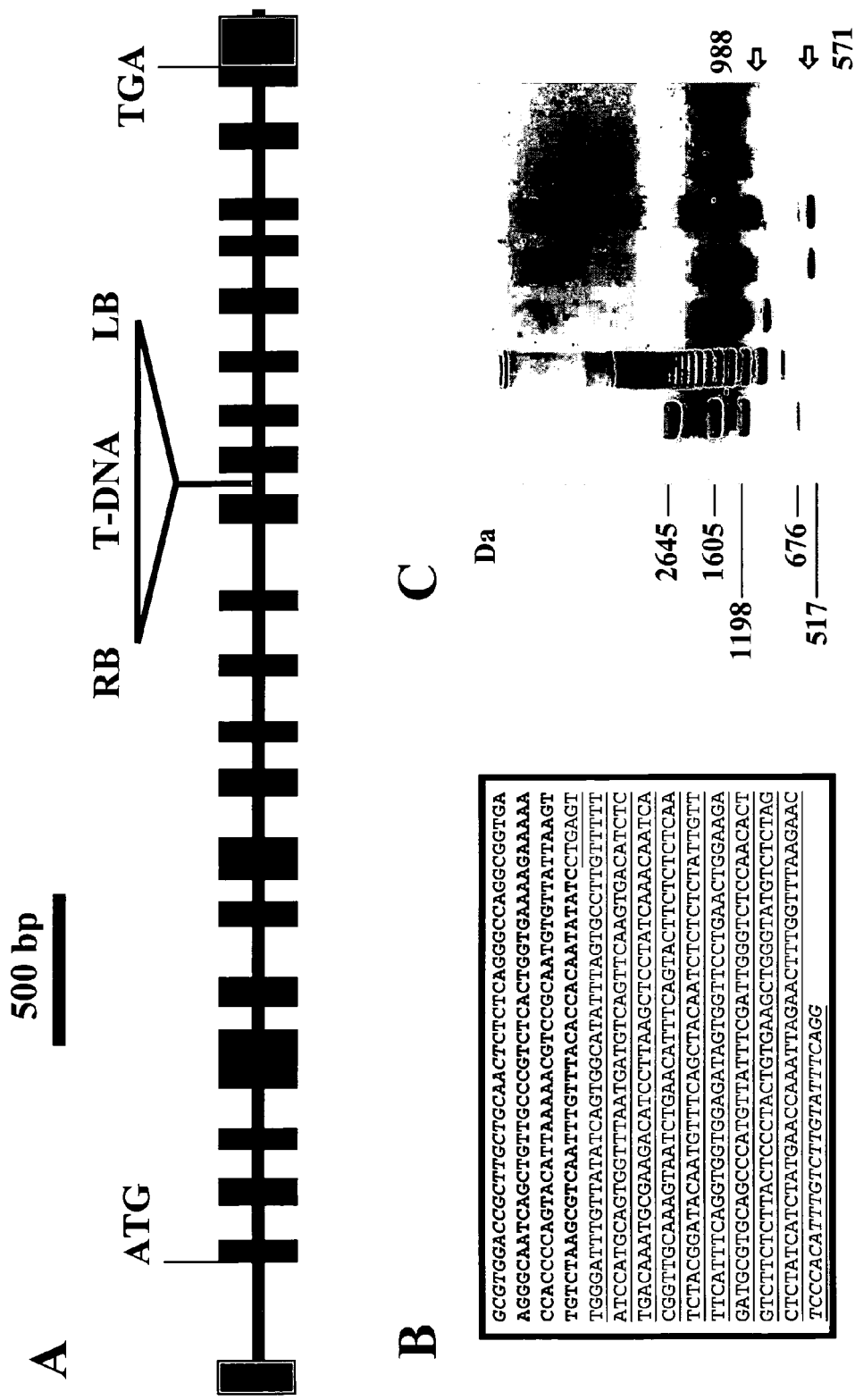
FIG. 8A-C

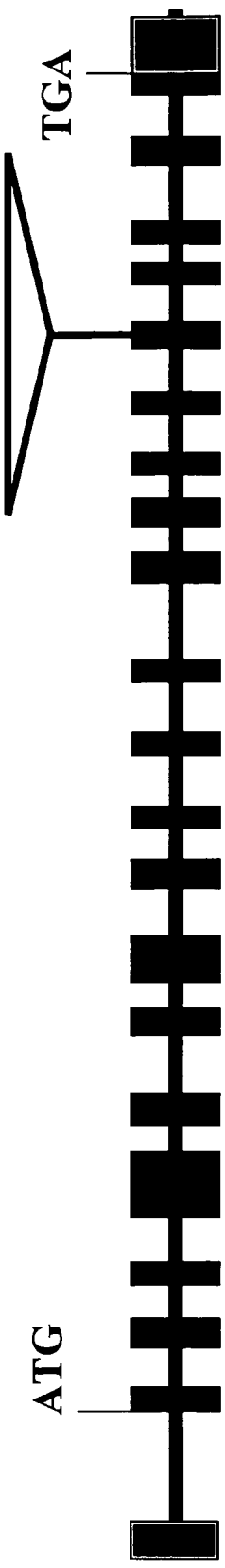
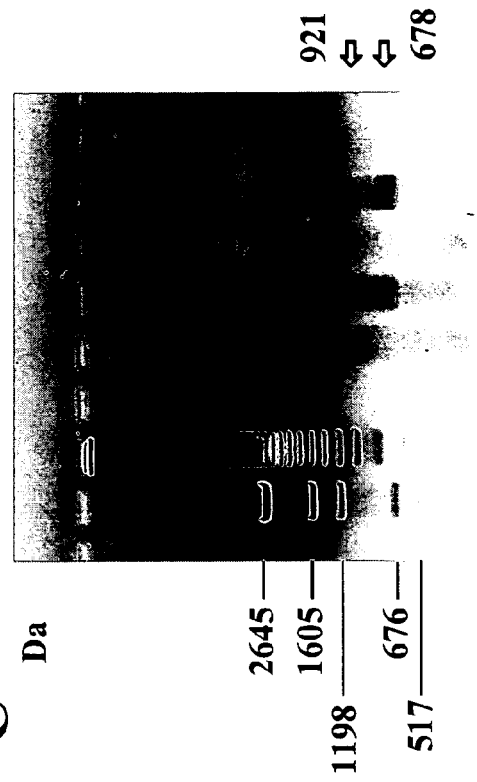
FIG. 9A-C

PLANT FATTY ACID AMIDE HYDROLASES

This application claims the priority of U.S. Provisional Patent Application Ser. No. 60/475,628, filed Jun. 4, 2003, the entire disclosure of which is specifically incorporated herein by reference. The government may own rights in this invention pursuant to grant number 2002-35318-12571 from USDA-NRICGP.

BACKGROUND OF THE INVENTION

1. Field of the Invention

The present invention relates generally to the field of molecular biology. More specifically, the invention relates to plant fatty acid amide hydrolase genes and methods of use thereof.

2. Description of the Related Art

N-Acylethanolamines (NAEs) are endogenous constituents of plant and animal tissues, and in vertebrates their hydrolysis terminates their participation as lipid mediators in the endocannabinoid signaling system. The membrane-bound enzyme responsible for NAE hydrolysis in mammals has been identified at the molecular level (designated fatty acid amide hydrolase, FAAH), and although an analogous enzyme activity was identified in microsomes of cotton seedlings, no molecular information has been available for this enzyme in plants.

NAEs are produced from the hydrolysis of N-acylphosphatidylethanolamines (NAPEs), a minor membrane lipid constituent of cellular membranes, by phospholipase D in animal systems (Schmid et al., 1996). One example of an NAE, anandamide (NAE 20:4), has varied physiological roles as an endogenous ligand for cannabinoid receptors and functions in modulation of neurotransmission in the central nervous system (Wilson and Nicoll, 2002). Anandamide also activates vanilloid receptors and functions as an endogenous analgesic (Pertwee, 2001) and appears to be involved in neuroprotection (Hansen et al., 2000; Van der Stelt et al., 2001). While a principal role for NAE20:4 as an endogenous ligand for cannabinoid receptors has emerged as a paradigm for endocannabinoid signaling (Desarnaud et al., 1995; Wilson and Nicoll, 2002), other types of NAEs as well as other fatty acid derivatives likely interact with this pathway and perhaps others directly or indirectly to modulate a variety of physiological functions in vertebrates (Lambert and Di Marzo, 1999; Lambert et al., 2002; Schmid and Berdyshev, 2002; Schmid et al., 2002).

NAEs have been implicated in immunomodulation (Buckley et al., 2000), synchronization of embryo development (Paria and Dey, 2000), and induction of apoptosis (Sarker et al., 2000). These endogenous bioactive molecules lose their signaling activity upon hydrolysis by fatty acid amide hydrolase (FAAH). Advances in the understanding of FAAH function in mammals at the structural level (Bracey et al., 2002), mechanistic level, and the physiological level (knockouts), have been made possible only through the cloning, expression and manipulation of the cDNA/gene encoding FAAH (Giang and Cravatt, 1997). Such studies have been lacking in plants due to the failure to isolate identify FAAH genes.

Research in the last decade has, however, indicated that NAE metabolism occurs in plants by pathways analogous to those in vertebrates and invertebrates (Chapman, 2000, Shrestha et al., 2002), pointing to the possibility that these lipids may be an evolutionarily conserved mechanism for the regulation of physiology in multicellular organisms. In plants, NAEs are present in substantial amounts in desiccated seeds (~1 µg g$^{-1}$ fresh wt) and their levels decline after a few hours of imbibition (Chapman et al., 1999). Individual plant NAEs have been identified in plants as predominantly 16C and 18C species with N-palmitoylethanolamine (NAE 16:0) and N-linoleoylethanolamine (NAE 18:2) generally being the most abundant. Like in animal cells, plant NAEs are derived from N-acylphosphatidylethanolamines (NAPEs) (Schmid et al., 1990; Chapman, 2000) by the action of a phospholipase D (PLD). The occurrence of NAEs in seeds and their rapid depletion during seed imbibition (Chapman, 2000) suggests that these lipids may have a role in the regulation of seed germination.

Recently, depletion of NAEs during seed imbibiton/germination was determined to occur via two metabolic pathways—one lipoxygenase—mediated, for the formation of NAE oxylipins from NAE 18:2, and one amidase—mediated for hydrolysis of saturated and unsaturated NAEs (Shrestha et al., 2002). Hydrolysis of NAEs was reconstituted and characterized in microsomes of cottonseeds, and appeared to be catalyzed by an enzyme similar to the FAAH of mammalian species (Shrestha et al., 2002).

While the foregoing studies have provided a further understanding of the metabolism of plant secondary metabolism, the prior art has failed to provide genes encoding plant fatty acid amide hydrolase. The identification of such genes would allow the creation of novel plants with improved phenotypes and methods for use thereof. There is, therefore, a great need in the art for the identification of plant fatty acid amide hydrolase genes.

SUMMARY OF THE INVENTION

In one aspect, the invention provides an isolated nucleic acid sequence encoding a plant fatty acid amide hydrolase and operably linked to a heterologous promoter. In certain aspects of the invention, the plant fatty acid amide hydrolase may be from a species selected from the group consisting of: *Arabidopsis thaliana*, barley, cotton, grape, maize, potato, rice, sugarcane, sorghum, soybean, tomato, wheat and *Medicago truncatula*. In one embodiment, the nucleic acid is further defined as selected from the group consisting of: (a) a nucleic acid sequence encoding the polypeptide of SEQ ID NO:2; (b) a nucleic acid sequence comprising the sequence of SEQ ID NO:1; and (c) a nucleic acid sequence hybridizing to SEQ ID NO 1 under conditions of 5× SSC, 50% formamide and 42° C. In another embodiment, the nucleic acid sequence encodes the polypeptide of SEQ ID NO:2, comprises the sequence of SEQ ID NO: 1 or hybridizes to SEQ ID NO:1 under conditions of 5× SSC, 50% formamide and 42° C.

In another aspect, the invention provides a recombinant vector comprising an isolated polynucleotide of the invention. In certain embodiments, the recombinant vector may further comprise at least one additional sequence chosen from the group consisting of: a regulatory sequence, a selectable marker, a leader sequence and a terminator. In further embodiments, the additional sequence is a heterologous sequence and the promoter may be developmentally-regulated, organelle-specific, inducible, tissue-specific, constitutive, cell-specific, seed specific, or germination-specific promoter. The recombinant vector may or may not be an isolated expression cassette.

In still yet another aspect, the invention provides an isolated polypeptide comprising the amino acid sequence of SEQ ID NO:2, or a fragment thereof having fatty acid amide hydrolase activity.

In still yet another aspect, the invention provides a transgenic plant transformed with a selected DNA comprising a nucleic acid sequence of the invention encoding FAAH. The transgenic plant may be a monocotyledonous or dicotyledonous plant. The plant may also be an R0 transgenic plant and/or a progeny plant of any generation of an R0 transgenic plant, wherein the transgenic plant has inherited the selected DNA from the R0 transgenic plant.

In still yet another aspect, the invention provides a seed of a transgenic plant of the invention, wherein the seed comprises the selected DNA. The invention also provides a host cell transformed with such a selected DNA. The host cell may express a protein encoded by the selected DNA. The cell may have inherited the selected DNA from a progenitor of the cell and may have been transformed with the selected DNA. The cell may be a plant cell.

In still yet another aspect, the invention provides a method of altering the N-Acylethanolamine content of a plant comprising up- or down-regulating fatty acid amide hydrolase in the plant. In one embodiment, the method comprises down-regulating fatty acid amide hydrolase in the plant and wherein the N-Acylethanolamine content of the plant is increased as a result of the down-regulating. In another embodiment of the invention, the method comprises up-regulating fatty acid amide hydrolase in the plant and wherein the N-Acylethanolamine content of the plant is decreased as a result of the up-regulating.

In still yet another aspect, the invention provides a method of modulating the growth of a plant or part thereof, comprising up- or down-regulating fatty acid amide hydrolase in the plant or part thereof. In one embodiment, the method comprises down-regulating fatty acid amide hydrolase in the plant and wherein the growth of the plant is decreased as a result of the down-regulating. In another embodiment of the invention, the method comprises up-regulating fatty acid amide hydrolase in the plant and wherein the growth of the plant is increased as a result of the up-regulating.

In still yet another aspect, the invention provides a method of modulating stress tolerance in a plant or part thereof, comprising up- or down-regulating fatty acid amide hydrolase in the plant or part thereof. In one embodiment, the method comprises down-regulating fatty acid amide hydrolase in the plant and wherein the stress tolerance of the plant is increased as a result of the down-regulating. In another embodiment of the invention, the method comprises up-regulating fatty acid amide hydrolase in the plant and wherein the stress tolerance of the plant is decreased as a result of the up-regulating.

In still yet another aspect, the invention provides a method of modulating pathogen perception in a plant or part thereof, comprising up- or down-regulating fatty acid amide hydrolase in the plant or part thereof. In one embodiment, the method comprises down-regulating fatty acid amide hydrolase in the plant and wherein the pathogen perception of the plant is increased as a result of the down-regulating. In another embodiment of the invention, the method comprises up-regulating fatty acid amide hydrolase in the plant and wherein the pathogen perception of the plant is decreased as a result of the up-regulating.

In a method of the invention, up-regulating may comprise introducing a recombinant vector of the invention into a plant. Down-regulating may comprise introducing a recombinant vector into a plant, wherein the nucleic acid or antisense oligonucleotide thereof is in antisense orientation relative to the heterologous promoter operably linked thereto. The vector may be introduced by plant breeding and/or direct genetic transformation.

In still yet another aspect, the invention provides a method of making food for human or animal consumption comprising: (a) obtaining the plant of the invention; (b) growing the plant under plant growth conditions to produce plant tissue from the plant; and (c) preparing food for human or animal consumption from the plant tissue. In the method, preparing food may comprise harvesting plant tissue. In certain embodiments, the food is starch, protein, meal, flour or grain.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

(FIG. 1A) The structure and organization of the *Arabidopsis* NAE amidohydrolase genomic sequence (TIGR/TAIR ID At5g64440). This gene is 4689 bp in length and the predicted protein is 607 amino acids in length with predicted molecular weight of 66.1 kDa and pI 6.44. There are 21 exons including 5'utr (untranslated region) and 3' utr (tigr.com on the worldwide web). The boxes represent exons and bars between exons represents introns. The light shaded boxes are utrs. (FIG. 1B) Schematic Structure of cDNA corresponding to At5g64440. Sequence-specific reverse transcriptase(RT) PCR primers (SEQ ID NOs:3 and 4, SEQ ID NO:4 shown in reverse) were designed based on the genomic sequence of *Arabidopsis thaliana* (*Arabidopsis* Genome Initiative, 2000) annotated at the Institute for Genomic Research (TIGR). The arrows denote the position of primers in the 5' and 3' utr. RT-PCR was performed with a total RNA extracted from the *Arabidopsis* leaves and the nucleotide sequence of the isolated cDNA is given in SEQ ID NO: 1. The sequence was 99.9% identical to coding region of TC139316 (*Arabidopsis*.org). (FIG. 1C) Schematic of domain organization of predicted *Arabidopsis* NAE amidohydrolase protein. Various domains identified in other proteins (ProDom, Altschul et al., 1997) are depicted above the diagram of the polypeptide (domains organized to scale and summarized in Table 1). These domains are also found in rat FAAH except the one denoted by an asterisk. PS00571 (PROSITE dictionary) denotes the amidase consensus sequence pattern of G-[GA]-S-[GS]-[GS]-G-x-[GSA]-[GSAVY (SEQ ID NO:27)]-x-[LIVM (SEQ ID NO:28)]-[GSA]-x(6)-[GSAT (SEQ ID NO:29)]-x-[GA]-x-[DE]-x-[GA]-x-S-[LIVM (SEQ ID NO:28)]-R-x-P-[GSAC (SEQ ID NO:30)]present in all proteins of the amidase class (Mayaux et al., 1990; Hashimoto et al., 1991; Chang and Abelson, 1990, Tsuchiya et al., 1989; Cumow et al., 1997; Cravatt et al., 1996). A single predicted transmembrane spanning region (shaded near N-terminus (ProDom, Altschul et al., 1997) and amidase signature sequence (Patricelli and Cravatt, 2000) are also shown.

FIG. 2A-2C. Comparative Alignment of *Arabidopsis* NAE amidohydrolase amino acid sequence FAAH. (FIG. 2A) Full length alignment of *Arabidopsis* amino acid sequence (SEQ ID NO:2) with rat FAAH (GenBank U72497; SEQ ID NO:7) (Cravatt et al., 1996). These proteins are members of the amidase signature (AS) sequence-containing superfamily which includes amidase or amidohydrolase (EC 3.5) enzymes involved in the reduction of organic nitrogen compounds and ammonia production (Chebrou et al., 1996; Patricelli and Cravatt, 2000). This AS region is underlined and consists of about 125 amino acids. There is 18.5% identity between the *Arabidopsis* protein and rat FAAH when compared over the entire length of the proteins, whereas there is 37% identity within the AS. Residues (Lys142, Ser217, Ser218, Ser241 and Arg243) are indicated with arrowheads. (FIG. 2B) Alignment of more conserved AS sequence (Ueda et al., 2000) for the enzymes that hydrolyze NAEs; mouse (GB # U82536) (Giang and Cravatt, 1997), porcine (GB # AB027132) (Goparaju et al., 1999), rat (GB # U72497) (Cravatt et al., 1996), and human (GB # U82535) (Giang and Cravatt, 1997) (see SEQ ID NOs:31-35). Out of fourteen conserved residues (in bold) in other amidase signature sequences (Patricelli et al., 1999) only two are different in *Arabidopsis* NAE amidohydrolase. (FIG. 2C) Secondary structure prediction (PSIPRED, McGuffin et al., 2000; Jones, 1999) of the AS (C, coil; H, helix; B, strand) are depicted above the rat and *Arabidopsis* AS sequences. Secondary structure organization is similar in the active site (or AS sequence in NAE amidohydrolase, Ueda et al., 2000) (SEQ ID NOs:36-37). This structural organization has been confirmed for rat FAAH by X-ray crystallography (Bracey et al., 2002) and suggests a functional link between these rat and *Arabidopsis* motif sequences despite limited primary amino acid sequence identity.

FIG. 4A-4C. SDS-PAGe, western blot, and activity assays of recombinant *Arabidopsis* NAE amidohydrolase expressed in *E. coli*. The c-myc-6×His-tagged recombinant protein expressed in *E. coli* was solubilized in DDM and affinity-purified in a Ni$^{2+}$ precharged resin column (PROBOND, Invitrogen) under "native" conditions. (FIG. 4A) Scan of Coomassie blue (R)-stained SDS gel (10 µg of total proteins in each lane except for rec. protein which was 2 µg) of select fractions. (FIG. 4B) Western blot analysis of same proteins as in A, probed with anti-myc monoclonal antibodies and visualized by indirect chemiluminescence (goat-antimouse IgG conjugated to horseradish peroxide). The position of the recombinant *Arabidopsis* fusion protein product (predicted to be ~70 kDa) is marked with open arrows. Positions of pre-stained standards (not shown) are indicated. FT=flow through and represents proteins not specifically bound to the Ni$^{2+}$ resin (pooled 4 washes) from Supt=supernatant and represents total proteins in *E.coli* lysates solubilized in DDM. Rec. protein=recombinant protein fraction affinity purified under "native" conditions. A small but detectable amount of 70 kDa immunoreactive protein was evident in total protein extracts, and as expected this protein was substantially enriched in the affinity-purification. (FIG. 4C) Enzymatic assays for NAE 18:2 hydrolysis, showed that amidohydrolase activity was enriched coincident with recombinant protein product.

FIG. 5. NAE-concentration dependent hydrolysis to FFA by affinity-purified recombinant *Arabidopsis* NAE amidohydrolase for NAE 20:4 and NEA 18:2 (FIG. 5A) or NAE 16:0, NAE 14:0 and NAE 12:0 (FIG. 5B). Initial velocity measurements were made at increasing concentrations of respective [1-$^{14}$C]NAE, combined with appropriate amount of non-radiolabeled NAE to give the final substrate concentration indicated. Reactions were initiated by the addition of 1 µg recombinant protein and were carried out in 50 mM Bis-Tris buffer, pH 9.0 in a final volume of 800 µL. Reactions were incubated for 30 minutes with shaking (100 rpm) at 30° C., and stopped by the addition of 2 mL boiling isopropanol. Lipids were extracted into chloroform, washed, and separated by TLC (Shrestha et al., 2002). Activity was calculated based on the amount of radioactive product formed. Data points represent means and standard deviations of triplicate assays, all performed on the same "batch" of purified protein. Plots were generated with Prism software v3.0 (GRAPHPAD Software, San Diego) by fitting the data to the Michaelis-Menten equation. Curve fits yielded correlation coefficients of $r^2 \geq 0.95$, and kinetic parameters summarized in Table 2 were derived from these plots.

FIG. 6. Alignment of amino acid sequences of the *Arabidopsis* (At5g64440) FAAH (At) (SEQ ID NO:2) with those of candidate FAAH orthologs from *Medicago truncatula* (Mt; SEQ ID NO:14) and *Oryza sativa* (OS, SEQ ID NO:12). Identical amino acid residues are blocked in black, whereas similar amino acid residues are shaded in gray. Alignment was generated with ClustalW algorithms. Over their full length, *Arabidopsis* and *Medicago* sequences were 64% identical, whereas *Arabidopsis* and rice sequences were 56% identical. *Medicago* and rice sequences were 57% identical. Residues determined to be important for amidase catalysis by the rat FAAH (K205, S281, S282, S305, R307 in the At sequence) are conserved in all plant sequences.

(FIG. 7A) rat FAAH cDNA, (FIG. 7B) Mt cDNA forward orientation, (FIG. 7C) Mt cDNA cloned in reverse orientation so as not to direct expression of a recombinant protein, (FIG. 7D) Os cDNA forward orientation, (FIG. 7E) Os cDNA cloned in reverse orientation so as not to direct expression of a recombinant protein, (FIG. 7F), At FAAH cDNA. The enzyme reactions were conducted as described for *Arabidopsis* recombinant FAAH (Shrestha et al., 2003; *J. Biol. Chem.* 278: 34990-34997). NAE amidohydrolase activities were detectable for both Mt and Os cDNAs cloned in the forward orientation (not in reverse), similar to that for At and rat FAAH enzymes, indicating that the candidate Mt and Os cDNAs indeed encode functional FAAH enzymes.

FIG. 8A-8C. Diagram of the location of the T-DNA disruption (intron 13) in the *Arabidopsis* FAAH gene in the SALK line 118043 (FIG. 8A) and the sequence of the gene region adjacent to the T-DNA insert amplified by PCR with T-DNA and gene specific primers (FIG. 8B) (SEQ ID NO:39). *Arabidopsis* plants homozygous for the T-DNA disruption were identified by PCR of genomic DNA (FIG. 8C).

FIGS. 9A-9C. Diagram of the location of the T-DNA disruption (exon 17) in the *Arabidopsis* FAAH gene in the SALK line 095198 (FIG. 9A) and the sequence of the gene region adjacent to the T-DNA insert amplified by PCR with T-DNA and gene specific primers (FIG. 9B) (SEQ ID NO:40). *Arabidopsis* plants homozygous for the T-DNA disruption were identified by PCR of genomic DNA (FIG. 9C).

DETAILED DESCRIPTION OF THE INVENTION

Figure 1:
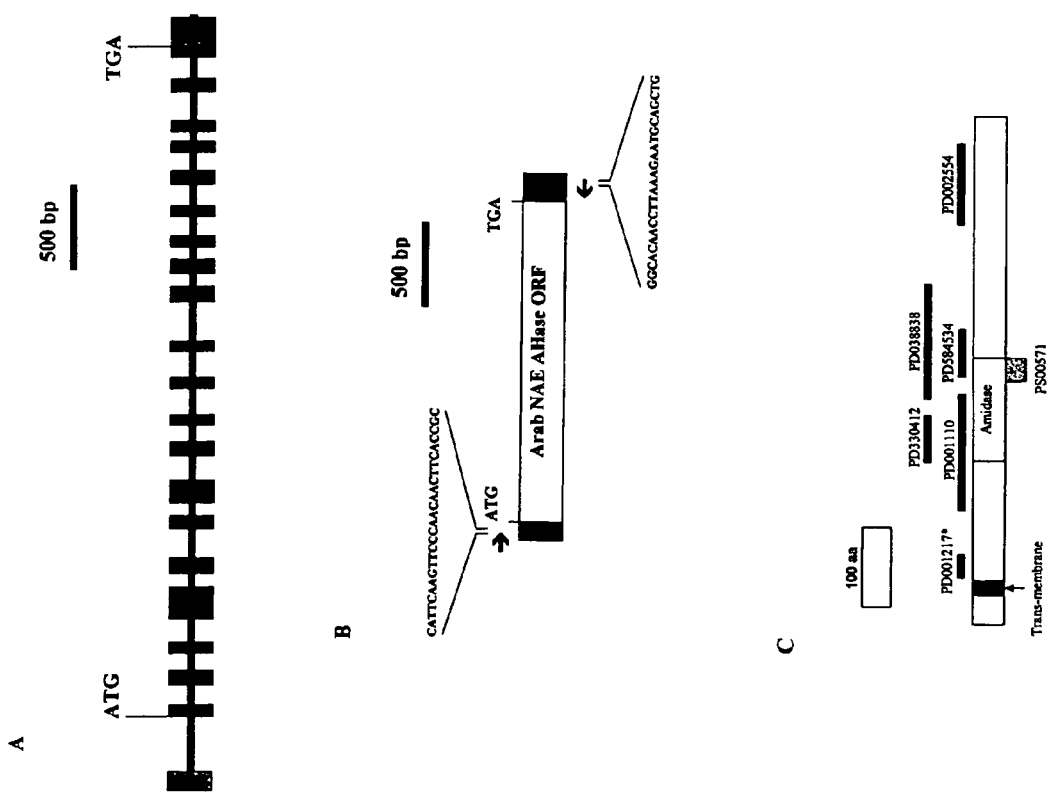
FIG. 1A-1C.

The invention overcomes the limitations of the prior art by providing plant fatty acid amide hydrolase (FAAH) coding sequences. As plant FAAH genes have not previously been isolated and identified, the invention represents a major advance and allows, for the first time, the creation of transgenic plants modified for plant FAAH expression. By introduction of one or more heterologous FAAH coding sequence into a plant, FAAH may be up-regulated in accordance with the invention. Similarly, the invention now allows the down-regulation of FAAH in a plant or any parts thereof, including a given cell, for example, using antisense, RNAi or any other desired technique known in the art using the nucleic acid sequences provided herein.

In plants, FAAH catalyzes the hydrolysis of N-acylethanolamines (NAEs), which are endogenous constituents of plant and animal tissues. The hydrolysis terminates a number of biological activities of NAEs, yielding important physiological responses. Therefore, by up-regulating FAAH, decreased levels of NAEs may be achieved and, conversely, down-regulation of FAAH may be used to increase NAE levels. Consistent with this, FAAH has been shown to be a key regulator of the degradation of bioactive NAEs, and hence, NAE levels and function in vivo (Cravatt and Lichtman, 2002; Ueda et al., 2000; Ueda 2002).

In initial studies by the inventors, a bioinformatics approach was taken to identify potential homologs of the mammalian FAAH in the *Arabidopsis thaliana* genome (*Arabidopsis* Genome Initiative, 2000) as a means to begin to understand at the molecular level, the physiological significance of this lipid metabolism pathway in higher plants. Initially, candidate *Arabidopsis* DNA sequences containing a characteristic amidase signature sequence (PS00571) were identified in plant genome databases and a cDNA was isolated from leaf RNA by RT-PCR using *Arabidopsis* genome sequences to develop appropriate oligonucleotide primers. The cDNA was sequenced and predicted to encode a protein of 607 amino acids with 37% identity to rat FAAH within the amidase signature domain (18% over the entire length). An analysis revealed conserved residues between the *Arabidopsis* and rat protein sequences determined to be important for FAAH catalysis. In addition, a single transmembrane domain near the N-terminus was predicted in the *Arabidopsis* protein sequence, resulting in a postulated topology similar to that of the rat FAAH protein.

Heterologous expression (in *E. coli*) and biochemical characterization of the *Arabidopsis thaliana* FAAH was carried out. The putative plant FAAH cDNA was expressed as an epitope/His-tagged fusion protein in *E. coli*, and solubilized from cell lysates in the nonionic detergent dodecylmaltoside. Affinity-purified recombinant protein was confirmed active in hydrolyzing a variety of naturally-occurring N-acylethanolamine types. Kinetic parameters and inhibition data for the recombinant *Arabidopsis* protein were consistent with these properties of the enzyme activity characterized previously in plant and animal systems. The identity of the functional *Arabidopsis* NAE amidohydrolase was thus confirmed.

The results provide, for the first time, molecular evidence for a conserved pathway in both plants and animals for the hydrolysis of NAEs. Moreover, the studies now provide a means to manipulate the levels of endogenous NAEs in plants. This, more importantly, now allows the manipulation of NAE levels in plants as a means to achieve improved plant phenotypes. For example, NAEs have been implicated in cellular response to physiological stresses. Therefore, an example of an application of the invention is in the modulation of NAE levels to achieve improved stress tolerance.

Important physiological roles have been indicated for NAEs in plants. One such role is in the perception of fungal elicitors by plant cells. In particular, the levels of endogenous NAE 14:0 are elevated 10-50 fold in leaves of tobacco plants following fungal elicitation (Tripathy et al., 1999). These NAE levels measured endogenously were shown sufficient to activate downstream defense gene expression in plants (Tripathy et al., 1999), and mammalian cannabinoid receptor antagonists abrogated the downstream response (Tripathy et al., 2003). A high-affinity NAE14:0-binding protein was identified in plant membranes and was indicated to mediate the NAE activation of defense gene expression (Tripathy et al., 2003). Therefore, one application of the current invention is in the alteration of plant perception to one or more pathogens through modulation of FAAH. By down-regulating FAAH, and thereby increasing NAEs, increased perception of pathogen elicitors may thereby be obtained. Similarly, it may be desired to decrease host cell defense mechanisms through the heterologous expression of FAAH. The foregoing may be achieved, for example, using inducible promoters activated by one or more pathogen elicitor, or using constitutive or other desired regulatory elements.

NAEs (primarily C12, C16 and C18 types) have also been shown to be present in high levels in desiccated seeds of higher plants, but metabolized rapidly during the first few hours of seed imbibition/germination (Chapman et al., 1999), in part by an amidohyrolase-mediated pathway (Shrestha et al., 2002), indicating that the transient changes in NAE content play a role in seed germination. In fact, *Arabidopsis* seedlings germinated and grown in the presence of exogenous NAE exhibited dramatically altered developmental organization of root tissues. An important role in seed germination and cell division in general has therefore been indicated. This is supported by evidence in mammalian cells that NAEs can stimulate apoptosis. Therefore, it may also be desired in accordance with the invention to modulate NAE levels in order to modulate cell division. By decreasing FAAH activity to increase NAE levels, a corresponding decrease in cell division may be obtained. This may be desirable, for example, for the creation of plants having shortened stature, or, through use of temporally- and/or developmentally-regulated heterologous promoter, for modulating growth at a given time period or stage of development. Seed germination may also thereby be modified. Alternatively, growth of plants may be increased by decreasing FAAH. This could be achieved, for example, using expression of FAAH or antisense or RNAi constructs thereof using seed and germination specific promoters, or constitutive or other promoters as desired.

I. Plant Transformation Constructs

Certain embodiments of the current invention concern plant transformation constructs. For example, one aspect of the current invention is a plant transformation vector comprising one or more FAAH coding sequence. Exemplary coding sequences for use with the invention include the *Arabidopsis thaliana*, rice and *M. truncatula* FAAH coding sequences (SEQ ID NOs:1, 11 and 13, respectively). Such coding sequences may encode a polypeptide having the amino acid sequence of SEQ ID NO:2, 12 or 14. The FAAH may in certain embodiments of the invention be characterized as from a species selected from the group consisting of: barley, cotton, grape, maize, potato, rice, sugarcane, sorghum, soybean, tomato, wheat and *Medicago truncatula*, as described herein. As such, the invention in certain embodiments provides nucleic acids comprising the sequence of any one of SEQ ID NOs:15-26. Also provided are nucleic acids encoding the polypeptides encoded by these sequences.

Sequences that hybridize to these coding sequences under stringent conditions are also provided by the invention. An example of such conditions is 5×SSC, 50% formamide and 42° C. It will be understood by those of skill in the art that stringency conditions may be increased by increasing temperature, such as to about 60° C. or decreasing salt, such as to about 1×SSC, or may be decreased by increasing salt, for example to about 10×SSC, or decreasing temperature, such as to about 25° C.

Nucleic acids provided by the invention include those encoding active FAAH fragments. Those of skill in the art will immediately understand in view of the disclosure that such fragments may readily be prepared by placing fragments of FAAH coding sequences in frame in an appropriate expression vector, for example, comprising a plant promoter. Using the assays described in the working examples, FAAH activity can be efficiently confirmed for any given fragment. Fragments of nucleic acids may be prepared according to any of the well known techniques including partial or complete restriction digests and manual shearing.

Sequences provided by the invention may be defined as encoding an active FAAH. In certain further aspects of the invention, a plant FAAH may be characterized as from a monocotyledonous or dicotyledonous plant. Coding sequences may be provided operably linked to a heterologous promoter, in either sense or antisense orientation. Expression constructs are also provided comprising these sequences, including antisense oligonucleotides thereof, as are plants and plant cells transformed with the sequences.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with FAAH coding sequences. The FAAH coding sequence may be provided with other sequences and may be in sense or antisense orientation with respect to a promoter sequence. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with an FAAH coding sequences will often depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV $^{35}$S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of a FAAH coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that FAAH coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a FAAH coding sequence is used. Alternatively, a heterologous 3' end may enhance the expression of sense or antisense FAAH coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

II. Antisense Constructs

Antisense treatments represent one way of altering FAAH activity in accordance with the invention. In particular, constructs comprising a FAAH coding sequence, including fragments thereof, in antisense orientation, may be used to decrease or effectively eliminate the expression of FAAH in a plant. Accordingly, this may be used to increase NAE levels and activity in a plant or given plant tissue. As such, antisense technology may be used to "knock-out" the function of a FAAH coding sequence or homologous sequences thereof.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject. In certain embodiments of the invention, such an antisense oligonucleotide may comprise any unique portion of a nucleic acid sequence provided herein. In certain embodiments of the invention, such a sequence comprises at least 18, 30, 50, 75 or 100 or more contiguous nucleic acids of the nucleic acid sequence of SEQ ID NO:1, which may be in sense/and or antisense orientation. By including sequences in both sense and antisense orientation, increased suppression of the corresponding coding sequence may be achieved.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

III. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. Agrobacterium-Mediated Transformation

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, alfalfa and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

IV. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,508,468; each of the disclosures of which is specifically incorporated herein by reference in its entirety).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

V. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected FAAH coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an R0 transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Identification of *Arabidopsis* NAE Amidohydrolase (FAAH)

In animal systems, fatty acid amide hydrolase (E.C. 3.5.1.4), a member of the amidase signature (AS) family (Cravatt et al., 1996; Ueda, 2002), hydrolyzes NAEs to produce free fatty acid (FFA) and ethanolamine (Ueda et al., 2000). A similar enzymatic activity was characterized previously in cottonseed microsomes (Shrestha et al., 2002). Mammalian FAAH enzymes have a conserved stretch of approximately 130 amino acids containing a Ser/Ser/Lys catalytic triad (Patricelli and Cravatt, 2003). The predicted amidase structure has a central conserved motif of G-G-S-S-(G/A/S)-G (Chebrou et al., 1996) and a somewhat longer stretch of amino acids G-[GA]-S-[GS]-[GS]-G-x-[GSA]-[GSAVY (SEQ ID NO:27)]-x-[LIVM (SEQ ID NO:28)]-[GSA]-x(6)-[GSAT (SEQ ID NO:29)]-x-[GA]-x-[DE]-x-[GA]-x-S-[LIVM (SEQ ID NO:28)]-R-x-P-[GSAC (SEQ ID NO:30)] is present in all enzymes of the amidase class (PS00457). Two serine residues at 217 and 241, highly conserved in the amidase signature (AS) sequence, were found essential for enzymatic activity of the recombinant rat FAAH (Deutsch et al., 1999). Mutation of either one of the residues into alanine caused complete loss of activity of the enzyme (Omeir et al., 2000; Patricelli et al., 1999). The mutation of another serine at 218 in the motif into alanine also caused marked loss of activity (Patricelli et al., 1999).

To assess whether the gene was expressed and to isolate a full length cDNA for functional characterization, oligonucleotide primers were designed within the 5' and 3' utr, and a cDNA fragment was amplified by RT-PCR from *Arabidopsis* leaf RNA (FIG. 1B). The RT-PCR product was sequenced and found to be 99.9% identical with the corresponding TC139316 annotated at TIGR. Protein domain prediction program (ProDom, Altschul et al., 1997) identified six domains, five of which were also found in rat FAAH (FIG. 1C). A single putative transmembrane segment was identified near the N-terminus (TMHMM (SEQ ID NO:38), Krogh et al., 2001; Sonnhammer et al., 1998) similar to the organization of rat FAAH. Several domains identified in *Arabidopsis* NAE amidohydrolase are summarized in Table 1.

TABLE 1

Summary of protein domains identified in *Arabidopsis* NAE amidohydrolase (ProDom, Altschul et al., 1997).

| Amino Acid Position | ID | Name | No of proteins in family |
|---|---|---|---|
| 271-407 | PD038838 | Biosynthesis of ligase glutamyl-trnagln 6.3.5.- | 167 |
| 138-276 | PD001110 | Glutamyl-trnagln 6.3.5.-hydrolase | 121 |
| 477-575 | PD002554 | Biosynthesis ligase glutamyl-trnagln | 173 |
| 197-253 | PD330412 | Amidotansferase glutamyl-trnagln | 64 |
| 298-358 | PD584534 | FAAH_Rat | 36 |
| 60-88 | PD001217 | Oligopeptide oligopeptide-binding transporter plasmid | 234 |

Alignment of deduced amino acids from the *Arabidopsis* NAE amidohydrolase cDNA with rat FAAH (GenBank U72497) (Cravatt et al., 1996) showed only 18.5% identity over the entire length. Alignment within the AS sequence of 125 amino acids showed 37% identity with five residues determined to be important for catalysis Lys-142, Ser-217, Ser-218, Ser-241 and Arg-243 (Patricelli and Cravatt, 2000) absolutely conserved (denoted by arrows; FIG. 2A). Comparison of a 47 amino acid motif within the AS showed the *Arabidopsis* protein had close to 60% identity with FAAHs from several mammalian species (FIG. 2B). Organization of predicted secondary structure within this *Arabidopsis* and rat FAAH AS motif were similar (FIG. 2C) and the structure of the rat enzyme has been confirmed by X-ray crystallography (Bracey et al., 2002). In addition, this putative *Arabidopsis thaliana* NAE amidohydrolase and rat FAAH have similar predicted molecular weights (~66 kDa), similar predicted topologies (single transmembrane segment near the N-terminus with C-terminus facing the cytosol, (TMHMM, Krogh et al., 2001; Sonnhammer et al., 1998) and similar predicted subcellular locations (secretory pathway, pSORT, Nakai and Kanehisa, 1992).

Although, there was limited primary amino acid sequence identity over the length of the *Arabidopsis* protein compared with the rat protein (18%), there was substantially higher similarity within the amidase catalytic domain both at the primary (37-60% depending on the lengths compared) and secondary structural levels (FIG. 2). Indeed expression of this *Arabidopsis* cDNA in *E. coli* confirmed that the *Arabidopsis* protein product was capable of hydrolyzing a wide range of NAE substrates to free fatty acids (FIGS. 3-5, Table 2), a feature also of the mammalian enzyme (Ueda et al., 2000; Borger et al., 2000). Kinetic parameters summarized in Table 2 indicate that the plant enzyme has similar affinities for NAE substrates as the FAAH from several mammalian species (Boger et al., 2000; Fowler et al., 2001; Cravatt et al., 1996; Pertwee et al., 1995; Bisogno et al., 1997; Tiger et al., 2000). Moreover, the inhibition of the *Arabidopsis* NAE amidohydrolase by MAFP (Table 3), the active-site directed irreversible inhibitor of rat FAAH (Deutsch et al., 1997; Bracey et al., 2002), strongly suggests a conserved enzyme mechanism between the plant and animal NAE amidases supporting the predictions from sequence/domain comparisons. It is thus indicated that the previous annotation accompanying At5g64440 was incorrect.

EXAMPLE 2

Functional Confirmation of *Arabidopsis* NAE Amidohydrolase (FAAH)

Figure 3:
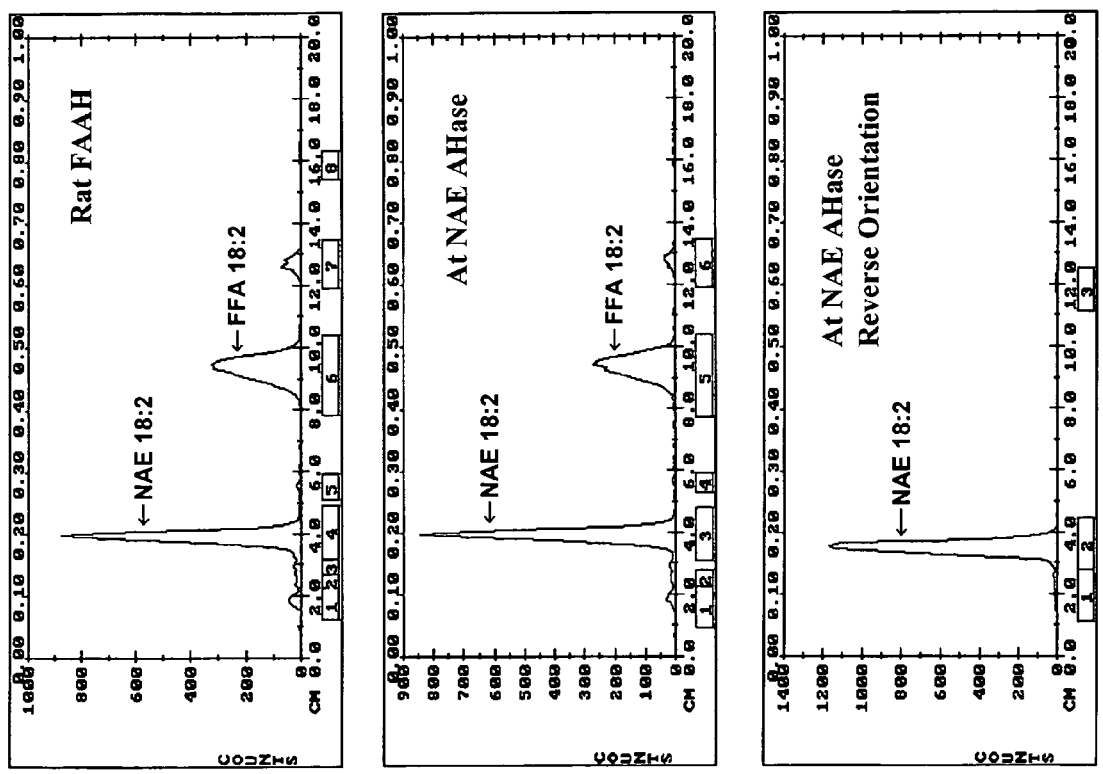
FIG. 3. Representative radiochromatograms of NAE amidohydrolase activity assays surveyed in *E. coli* harboring expression plasmids. Lysates from cells expressing recombinant rat FAAH (Patricelli et al., 1999) were compared with lysates of cells designed to express the *Arabidopsis* NAE amidohydrolase cDNA in forward (middle panel) or reverse orientation (lower panel) with respect to the lacZ promoter. In all cases cDNAs were in pTrcHis2 expression plasmids and recombinant protein expression was induced by 4 h incubation with 1 mM IPTG. For assays, 100 µM [1-$^{14}$C] NAE 18:2 (~20,000 dpm) in 50 mM Bis-Tris buffer (pH 9.0) was used. The reactions included 50 µg protein of respective cell lysate and were incubated for 30 min at 30° C. with shaking. Lipids were extracted and separated by TLC. The positions of [1-$^{14}$C]NAE 18:2 substrate and [1-$^{14}$C]FFA product are indicated.

The *Arabidopsis* putative NAE amidohydrolase was subcloned into pTrcHis and pTrcHis2 for expression in *E. coli* of N-terminal and C-terminal, epitope and polyhistidine-tagged fusion proteins. *E. coli* lysates were surveyed for expression of enzyme activity using [$^{14}$C]NAE 18:2 (N-linoleoylethanolamine; radiolabeled on the carbonyl carbon) as substrate. Representative chromatograms shown in FIG. 3 indicate that like the recombinant rat FAAH (expressed in the same vector), the recombinant *Arabidopsis* protein effectively hydrolyzed [1-$^{14}$C]NAE 18:2 to [1-$^{14}$C]FFA 18:2. As a control, *E. coli* expressing *Arabidopsis* cDNA in reverse orientation showed no hydrolytic activity (FIG. 3). In these preliminary studies with crude *E. coli* lysates, the *Arabidopsis* NAE amidohydrolase activity was determined to be time-, temperature- and protein concentration-dependent. The *Arabidopsis* NAE amidohydrolase did not hydrolyze ceramide, nor did ceramide influence NAE hydrolysis. The *Arabidopsis* NAE amidohydrolase did not catalyze the reverse reaction of NAE hydrolysis (formation of NAE) under any conditions tested. Higher activity was reproducibly recovered in cells expressing C-terminal fusions, compared with cells expressing N-terminal fusions. Similar to reports for the rat protein (Patricelli et al., 1998), the recombinant *Arabidopsis* NAE amidohydrolase was mostly associated with *E. coli* membranes.

EXAMPLE 3

Affinity-Purification of Recombinant Enzyme

The *Arabidopsis* NAE amidohydrolase, expressed as a C-terminal fusion protein, was solubilized in n-dodecyl-β-

Figure 4C:
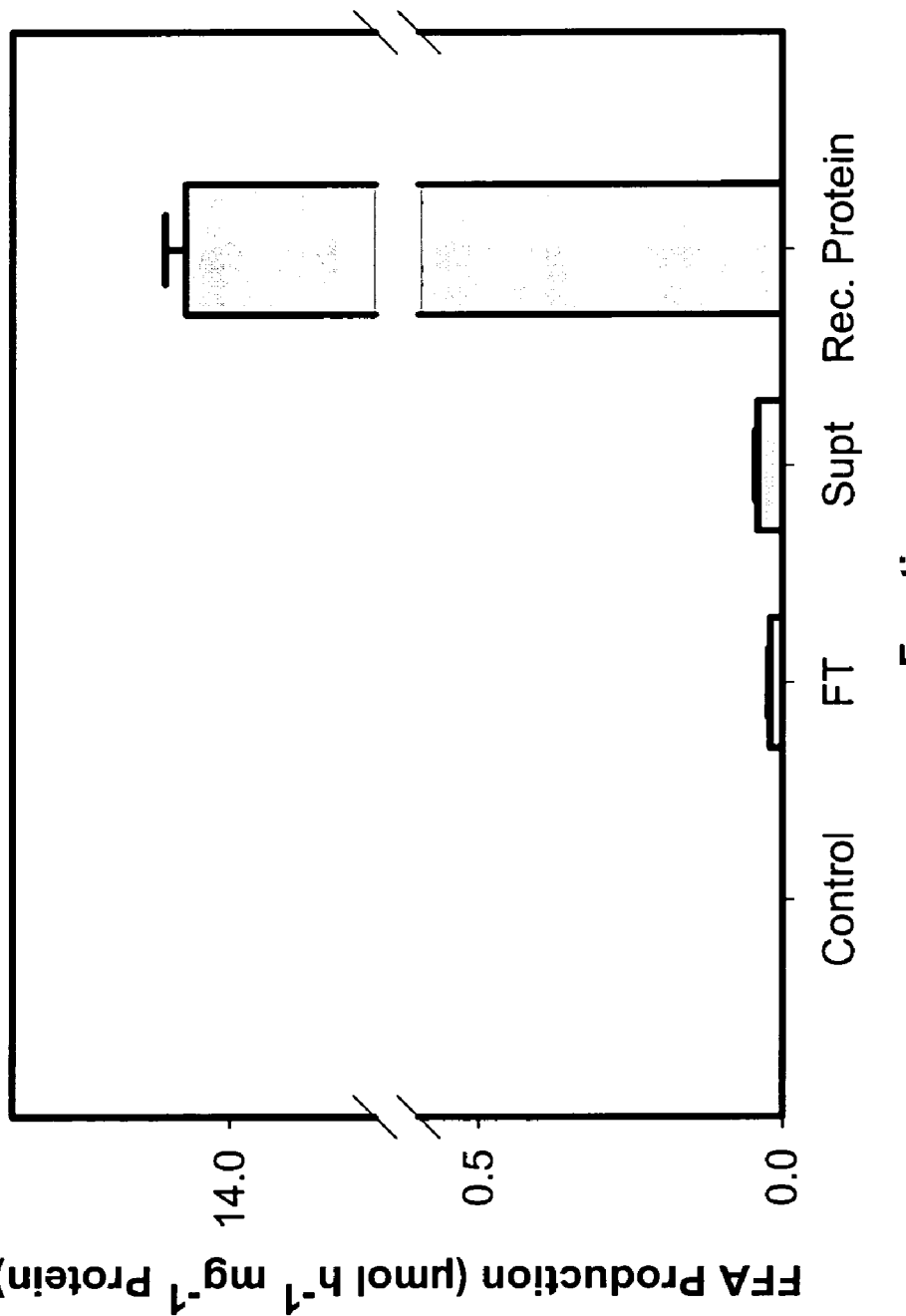
Figure 7A:
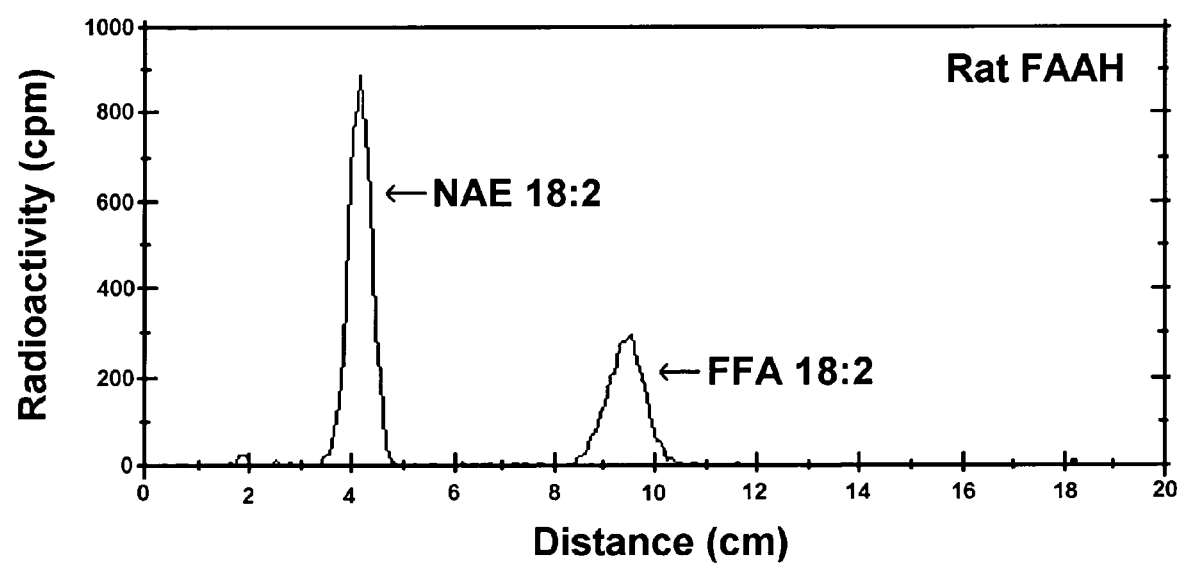
FIG. 7A-7F. Representative radiochromatograms of lipids extracted from reaction mixtures following assays of NAE amidohydrolase (NAE AHase) activity (measured as formation of radiolabeled FFA 18:2 from radiolabeled NAE18:2 in this case) and separated by Silica gel-thin layer chromatography (TLC). In all cases, *E. coli* lysate (20 µg protein) was used as the enzyme source, from cells harboring the following different cDNAs in pTrcHIS2 expression plasmids.
Figure 7B:
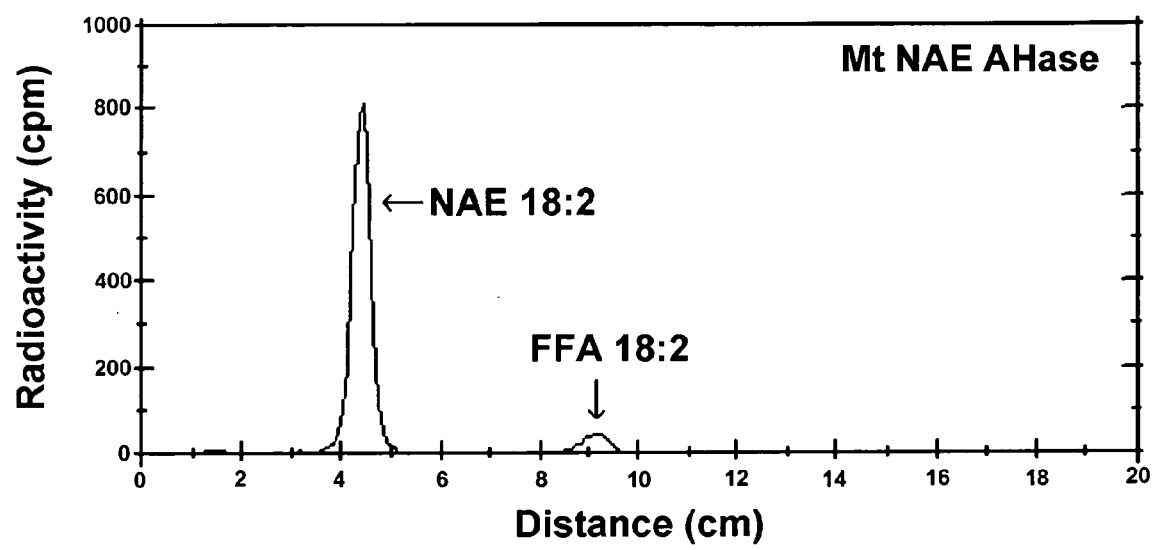
Figure 7C:
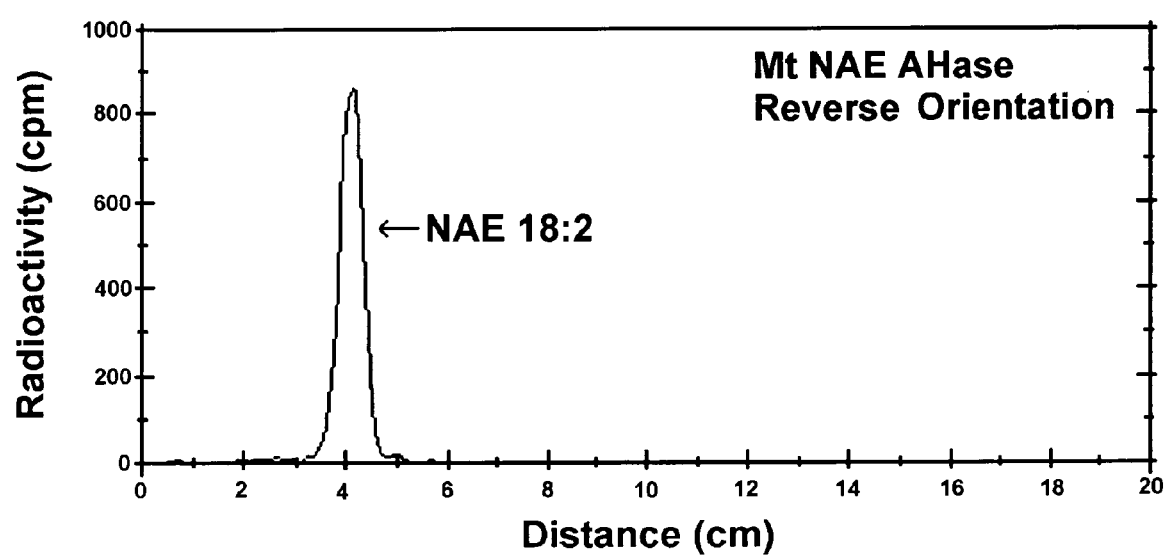
Figure 7D:
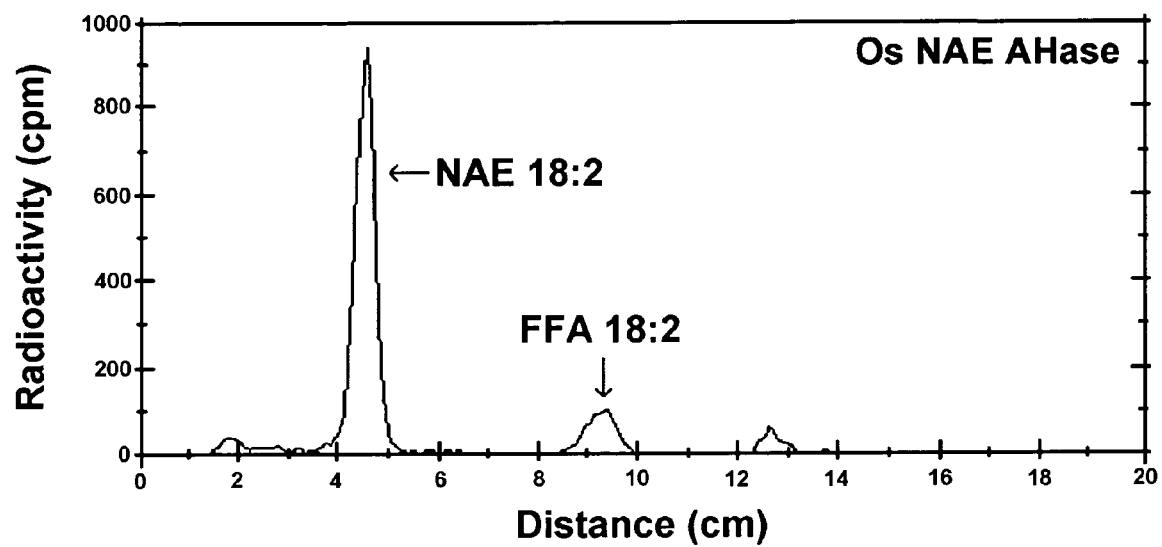
Figure 7E:
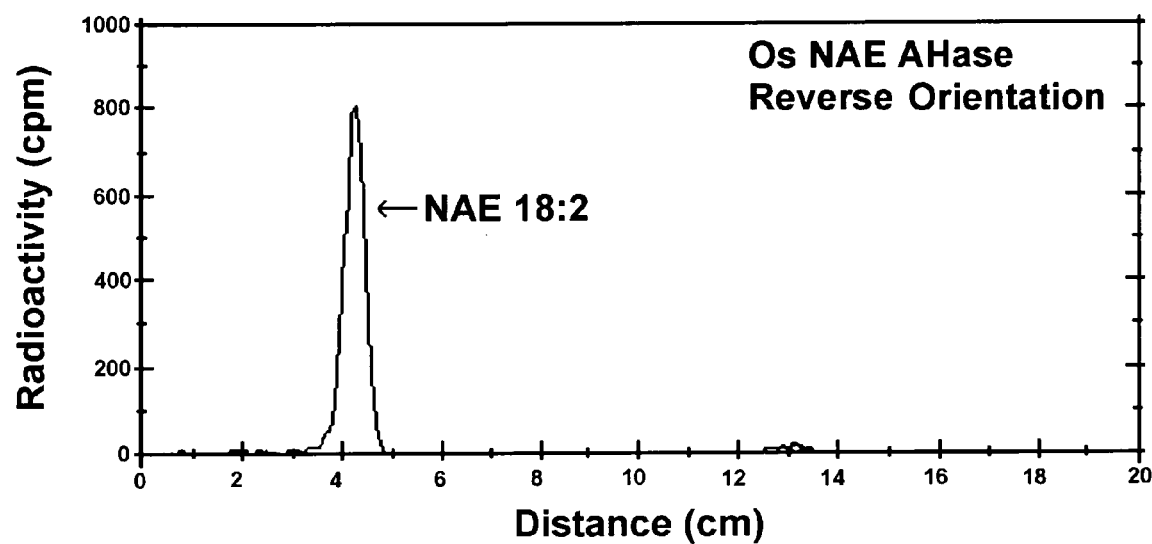
Figure 7F:
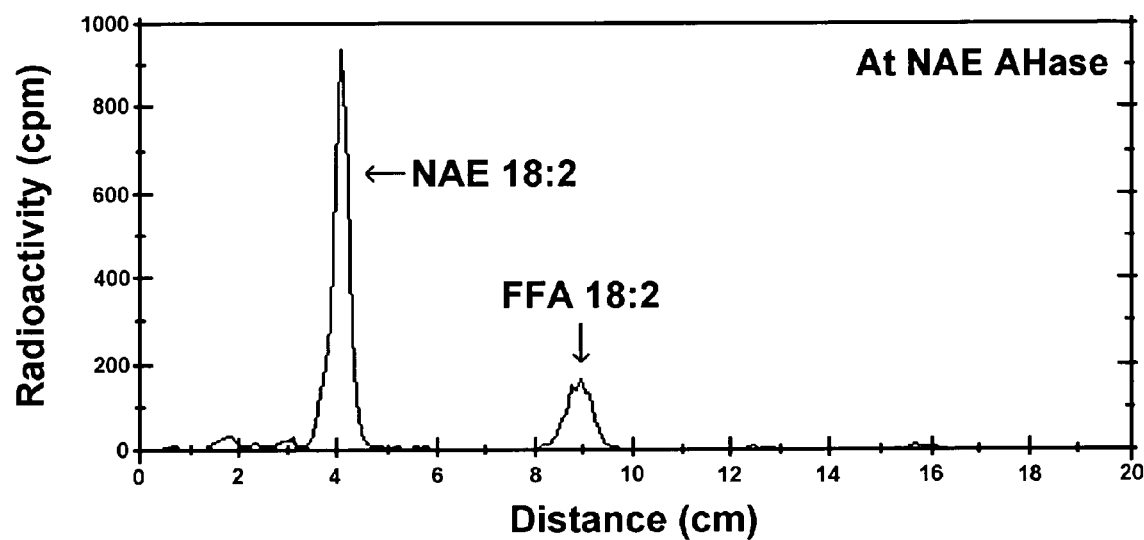

D-maltoside (DDM), and subjected to native $Ni^{2+}$-affinity purification, SDS-PAGE, western blot analyses, and enzyme activity assays (FIG. 4). A protein of approximately 70 kDa was enriched under native conditions by $Ni^{2+}$-affinity purification and was detected by the c-myc antibody (FIG. 4A, B arrows, recombinant protein lanes). Likewise, NAE amidohydrolase activity was enriched in this native affinity-purified protein fraction (FIG. 4C) by approximately 375 fold, relative to the DDM-solubilized supernatant (supt) fraction. More stringent denaturing conditions led to purification of the recombinant protein to homogeneity (single 70 kDa band on gel), but also inactivated the enzyme.

EXAMPLE 4

Biochemical Characterization

Recombinant NAE amidohydrolase (AHase) activity was evaluated by incubating affinity-purified NAE amidohydrolase with $[1-^{14}C]$NAE 20:4, $[1-^{14}C]$NAE 18:2, $[1-^{14}C]$NAE 16:0 (N-palmitoylethanolamine), $[1-^{14}C]$NAE 14:0 (N-myristoylethanolamine) or $[1-^{14}C]$NAE 12:0 (N-lauroylethanolamine) and measuring the rate of conversion to their respective $[1-^{14}C]$FFA products. NAE amidohydrolase exhibited saturation kinetics with respect to all NAE substrates tested, including those identified in plant tissues and those not found in plant tissues. The enzyme exhibited typical Michaelis-Menten kinetics when initial velocity measurements were made at increasing substrate concentrations (FIG. 5) and parameters calculated from these plots are summarized in Table 2. The relative apparent $K_m$ of the Arabidopsis enzyme varied by a factor of about four depending upon NAE type. Surprisingly, the Arabidopsis enzyme had a higher affinity toward the non-plant NAE 20:4, than toward the more abundant endogenous plant NAE 16:0 and 18:2. The highest maximum rate of NAE hydrolysis also was estimated for NAE 20:4 compared to the endogenous plant NAEs, although the range of the difference was not as great. Although this is not a purified protein preparation, these parameters together suggest that the Arabidopsis recombinant enzyme recognizes a wide range of NAE types, similar to the situation with mammalian FAAH, and highlights the caution of over interpreting in vitro kinetic data.

TABLE 2

Summary of apparent kinetic parameters of the affinity-purified recombinant Arabidopsis thaliana NAE amidohydrolase. Parameters were estimated by fitting the data in FIG. 5 to the Michaelis-Menten equation (Prism software, version 3.0, GraphPad software).

| Substrate | $K_m$ (μM) | $V_{max}$ (μmol $h^{-1}$ $mg^{-1}$ protein) |
|---|---|---|
| NAE 20:4 | 13.6 ± 2.1 | 17.9 ± 0.6 |
| NAE 18:2 | 26.2 ± 5.3 | 14.1 ± 0.8 |
| NAE 16:0 | 50.8 ± 14.1 | 12.1 ± 1.1 |
| NAE 14:0 | 37.0 ± 5.6 | 9.1 ± 0.4 |
| NAE 12:0 | 17.6 ± 2.8 | 13.9 ± 0.5 |

Two different mechanism-based inhibitors of mammalian FAAH were tested for potency on the hydrolysis of $[1-^{14}C]$NAE 18:2 by this novel plant NAE amidohydrolase (Table 3). Phenylmethylsulfonyl fluoride (PMSF), a non-specific irreversible serine hydrolase inhibitor that inhibits NAE hydrolysis by mammalian FAAH at low mM concentrations (Desarnaud et al., 1995) was only modestly affective on the Arabidopsis enzyme (inhibited by 44% at 10 mM). However, methyl arachidonyl fluorophosphonate (MAFP), the irreversible, active-site targeted inhibitor of rat FAAH (Bracey et al., 2002) completely eliminated NAE hydrolysis by the Arabidopsis enzyme at 10 nM. Overall, biochemical results strongly supported the identification of At5g64440 as a functional homologue of the mammalian FAAH.

TABLE 3

The effects of two mechanism-based inhibitors of mammalian FAAH on the hydrolysis of $[1-^{14}C]$NAE 18:2 by the affinity purified Arabidopsis recombinant enzyme. Assays were conducted for 30 min at 30° C. in the absence or presence of increasing concentrations of phenylmethylsulfonyl fluoride (PMSF) or methyl arachidonyl fluorophosphonate (MAFP). The amount of $[1-^{14}C]$FFA 18:2 formed was quantified by radiometric scanning following TLC or reactions products. The data are means and SD of three replicates and are representative of two studies.

| Concentrations | Specific Activity μmol $h^{-1}$ $mg^{-1}$ Protein | Relative Inhibition (%) |
|---|---|---|
| Phenylmethylsulfonyl fluoride (PMSF) | | |
| 0 mM | 10.56 ± 0.29 | 0 |
| 0.01 mM | 11.34 ± 0.55 | −7 |
| 0.1 mM | 9.06 ± 1.86 | 14 |
| 1 mM | 7.89 ± 0.37 | 25 |
| 2.5 mM | 6.72 ± 0.70 | 36 |
| 10 mM | 5.96 ± 0.43 | 44 |
| Methyl arachidonyl fluorophosphonate (MAFP) | | |
| 0 nM | 10.46 ± 0.32 | 0 |
| 0.1 nM | 9.69 ± 0.89 | 7 |
| 1 nM | 5.62 ± 0.56 | 46 |
| 10 nM | 0.00 ± 0.00 | 100 |

EXAMPLE 5

Materials $[1-^{14}C]$Arachidonic acid was purchased from PerkinElmer Life Sciences, and $[1-^{14}C]$Lauric acid was from Amersham Biosciences, and $[1-^{14}C]$myristic, arachidonic, lauric, linoleic, and myritstic acids, anandamide, and arachidonyl trifluoromethyl ketone (ATMK), phenylmethylsulfonyl fluoride (PMSF), and isopropyl β-D-thiogalactopyranoside (IPTG) were from Sigma. $[1-^{14}C]$Linoleic, and $[1-^{14}C]$palmitic acids, and $[1,2-^{14}C]$ethanolamine were purchased from NEN, ceramide was from Avanti Polar Lipids, and 2-arachidonyl glycerol (2-AG) was from Cayman Chemical (Ann Arbor, Mich.). Methyl arachidonyl fluorophosphonate (MAFP) was from TOCRIS (Ellisville, Mo.), n-dodecyl-β-D-maltoside (DDM) was from Calbiochem, and Silica Gel 60 Å glass plates for thin-layer chromatography (20 cm×20 cm, 0.25 mm thickness) were from Whatman (Clifton, N.J.). Specific types of N-$[1-^{14}C]$ acylethanolamines were synthesized from ethanolamine and respective $[1-^{14}C]$fatty acids by first producing the fatty acid chloride (Hillard, et al., 1995).

EXAMPLE 6

Bioinformatics and cDNA Isolation

BLAST searches (//blast.wustl.edu) in various databases were done using the amidase signature (AS) consensus block embedded in rat FAAH (//blocks.fhcrc.org). DNA sequences containing a characteristic AS sequence (PS00571) were identified in the Arabidopsis thaliana genome database annotated at www.tigr.org, and one candidate Arabidopsis FAAH ortholog, At5g64440, was selected for further analyses. Sequence-specific primers were designed within the 5' and 3' utr regions based on predicted exon sequences and used for reverse transcriptase PCR (forward, 5'-CATTCAAGTTCCCAACAACTTCAC-CGC-3' (SEQ ID NO:3) and reverse, 5'-GTCGACGTAA-GAAATTCCAACACGG-3' (SEQ ID NO:4). The template for RT-PCR was total RNA extracted from the leaves of mature *Arabidopsis* plants using Trizol reagent (Invitrogen). Fresh leaf tissue (100 mg) was harvested and ground to a fine powder in liquid nitrogen. The powdered tissue was combined with 2 mL of Trizol reagent and RNA was isolated per manufacturer's instructions.

For RT-PCR, the first-strand cDNA synthesis was carried out at 50° C. for 30 min and incubated for 4 min at 94° C. before the targeted amplification of the At5g64440 mRNA by RT/Platinum Taq mixture (Invitrogen) was achieved through 25 cycles of 94° C. for 1 min, 45° C. for 1 min, 72° C. for 2 min followed by a final polymerization step at 72° C. for 7 min. The RT-PCR product was gel-purified and ligated into pTrcHis for nucleotide sequencing. Commercial DNA sequencing of both strands (complete 2× each strand) verified the identity of the cDNA as the AT5g64440 gene product, and the complete cDNA sequence was deposited in GenBank.

EXAMPLE 7

Protein Expression

For protein expression, oligonucleotide primers (forward, 5'-ATGGGTAAGTATCAGGTCATGAAACG-3' (SEQ ID NO:5) and reverse, 5'-GTTTGTATTGAGAATATCAT-AAAAGATTGC-3' (SEQ ID NO:6) were designed to amplify only the open reading frame (ORF) of the above At5g64440 cDNA. The PCR product was gel purified as above and subcloned into expression vectors, pTrcHis and pTrcHis2, and the constructs were transformed into *E. coli* TOP10 as host. Transformed colonies were selected with correct in-frame fusions and cDNA sequence by sequencing of plasmid DNA over the vector insert junctions and by sequencing the inserts completely on both strands.

Selected transformed cell lines were grown in LB medium without glucose to an $OD_{600}$ of 0.6 to 0.7 and induced with 1 mM IPTG for 4 h. Pelleted cells were resuspended in lysis buffer (50 mM Tri-HCl, pH 8.0, 100 mM NaCl and 0.2 mM DDM) at a ratio of 2.3:1017 (*E. coli* cells:DDM molecules) (0.1 $OD_{600}=10^8$ cells/mL, Elbing and Brent, 2002). After incubation on ice for 30 min resuspended cells were sonicated on ice with six 10-s bursts at high intensity with a 10-s cooling period between each burst. The selection of DDM as the detergent, and determination of optimal DDM concentration and content ratio was based on empirical comparisons for recovery of solubilized active enzyme with the highest specific activity. DDM was for this purpose than either Titron X-100 or CHAPS (3-[(-Cholamidopropyl)dimethylammonia]-1-propanesulfonate).

EXAMPLE 8

Solubilization and $Ni^{2+}$ Affinity Purification

Routinely, cultured cells (50 mL) were pelleted, resuspended in 8 mL of native binding buffer (50 mM $NaPO_4$ and 0.5 M NaCl) with 8 mg of lysozyme, and 0.2 mM DDM (final) incubated on ice for 30 min, and disrupted by sonication as above. The crude lysate was centrifuged at 105,000×g for 1 h in a Sorvell Discovery 90 model ultracentrifuge (Beckman 45 Ti rotor). The supernatant was combined with ProBond resin, precharged with $Ni^{2+}$ and gently agitated for 60 min to keep the resin suspended in the lysate supernatant. The resin with adsorbed protein was settled and the supernatant was aspirated off. The resin was washed 4 times to remove non-specific proteins, and the adsorbed proteins were eluted with imidazole-containing buffer. Eluted proteins were concentrated and imidazole was removed with 50 mM Tris-HCl, pH 8.0, 100 mM NaCl and 0.2 mM DDM by filtration-centrifugation using Centricon YM-30 (Millipore, Bedford, Mass.). Affinity-purified proteins were stored at −80° C. in 10% glycerol and were stable for more than two months.

EXAMPLE 9

Gel Electrophoresis and Western Blotting

Protein samples were diluted in 60 mM Tris-HCl, pH 6.8, 2% SDS, 10% glycerol, 0.025% bromophenol blue in 1:1 ratio and separated on 8 cm precast 10% polyacrylamide/ SDS gel (Bio-Rad) at 35 mA for 30 min and 60 mA for 60 min. For western blot analysis, separated proteins were electrophoretically transferred to PVDF (polyvinylidene fluoride, 0.2 μm, Bio-Rad) membrane in a Semidry Trans-Blot apparatus (Bio-Rad) for 30 min at constant 14 volts. Recombinant proteins expressed as c-myc-epitope fusions were localized with 1:5000 dilution of anti-myc antibodies (mouse monoclonal, Invitrogen) and detected by chemiluminescence (Bio-Rad substrate solution) following incubation with 1:2500 goat-antimouse IgG conjugated to horseradish peroxidase (Bio-Rad).

EXAMPLE 10

NAE Amidohydrolase Assays

NAE substrates were synthesized and purified, and enzyme assays were conducted as previously described (Shrestha et al., 2002) with a few modifications. Generally the enzyme source was incubated with 100 μM [14C]NAE with 20,000 dpm in 50 mM Bis-Tris (2-[bis(2-hydroxyethyl) amino]-2-(hydroxymethyl)propane-1) buffer (pH 9.0) for 30 min to survey for NAE amidohydrolase activity (Shrestha et al., 2002). Enzyme activity was examined for time, temperature, protein- and substrate-concentration dependence. For enzyme characterization, reactions were initiated with 1 μg of affinity-purified protein and incubated at 30° C. with shaking for 30 min. Assays of lysate of *E. coli* cells expressing rat FAAH (WT) (Patricelli et al., 1999) served as a comparison of NAE amidohydrolase activity, whereas non-transformed cell lysates or cell lysates with the *Arabidopsis* cDNA cloned in reverse orientation with respect to the lacZ promoter served as negative controls for activity assays.

Enzyme assays were terminated by the addition of boiling isopropanol (70° C.) and lipids were extracted into chloroform. Lipid products were separated by TLC and the distribution of radioactivity was evaluated by radiometric scanning (Shrestha et al., 2002). Activity was calculated based on the radiospecific activity of [$^{14}C$]-labeled substrate. A general serine hydrolase inhibitor, phenylmethylsulfonyl fluoride (PMSF), and an irreversible active-site-directed FAAH inhibitor, methyl arachidonyl fluorophosphonate (MAFP), were used to probe the sensitivity of recombinant *Arabidopsis* NAE amidohydrolase activity. Inhibitors were added from stock solutions dissolved in (PMSF, isopropanol;

ATMK and MAFP, DMSO), and activity was adjusted for minimal solvent effects when necessary. Protein content was determined by using serum albumin as the standard (Bradford, 1976).

EXAMPLE 11

Identification of Candidate FAAH Sequences in Rice and Medicago truncatula

Using BLAST search programs, a candidate FAAH gene sequence was identified in the rice genome on chromosome 4 with similarity to the Arabidopsis FAAH gene, At5g64440. This gene was predicted in the database to encode a protein of 578 amino acids. The rice FAAH homologue predicted gene sequence is given in SEQ ID NO:8, the predicted mRNA (without untranslated regions) sequence is in SEQ ID NO:9 and the predicted amino acid sequence of the gene product is given in SEQ ID NO:10. The rice gene nucleotide sequence was retrieved from the Oryza sativa non-redundant database in Genbank using the Arabidopsis At5g64440 FAAH sequence as the query.

Using oligonucleotide primers directed to the 5' and 3' ends of the full-length rice ORF, a cDNA was isolated from total RNA of 2-d old Oryza sativa (cv japonica cultivar) seedlings by reverse-transcriptase (RT)-PCR. The rice cDNA fragment was cloned into the expression plasmid, pTrcHis2 TOPO (Invitrogen), and completely sequenced on both strands. The nucleic acid sequence of the cloned cDNA is given in SEQ ID NO:11 and the predicted amino acid sequence of the actual rice FAAH cDNA isolated by RT-PCR is given in SEQ ID NO:12.

The cDNA coding sequence was longer than what was predicted in DNA databases, such that the protein product was estimated to be 601 amino acids, closer to the 607 amino acids of the Arabidopsis FAAH protein than to the 578 amino acids of the predicted rice FAAH (SEQ ID NO:12). The segment that was missing in the predicted rice sequence was between amino acids 486 and 509 in the sequence isolated from rice seedlings and this segment was conserved in the Arabidopsis FAAH. It was therefore indicated that the annotation of the gene was in error, comprising a failure to identify the corresponding exon correctly, and that the correct sequence is in SEQ ID NO:12.

BLAST search programs also were used to query the Medicago truncatula EST database for to identify FAAH homologues. A candidate EST clone (Accession AW695697) was obtained from the S. R. Noble EST collection (designated as NF097F02ST1F1025), and was sequenced completely on both strands. The nucleotide sequence of the processed cDNA is given in SEQ ID NO:13 and the predicted amino-acid sequence in SEQ ID NO:14.

Primers designed to the 5' and 3' ends of the protein coding region were used to amplify and subclone a PCR product of this Medicago candidate FAAH into the expression plasmid, pTrcHis2 TOPO (Invitrogen), as above for the rice candidate FAAH. DNA sequencing verified the correct sequence, orientation and in-frame insertion of the PCR product in the recombinant expression vector.

An alignment of the amino acid sequences of the Arabidopsis FAAH (At; At5g6440) with the candidate sequences from rice (OS) and Medicago truncatula (Mt), showed that these sequences share a high degree of similarity (FIG. 6). Over their full lengths, Arabidopsis and Medicago sequences were 64% identical, whereas Arabidopsis and rice sequences were 56% identical. Medicago and rice sequences were 57% identical. Amino acid residues determined to be important for amidase catalysis (K205, S281, S282, S305, R307 in the At sequence) by the rat FAAH (genbank accession NM_024132) are conserved in all plant sequences. Based on sequence similarity and conserved amidase domains, it was indicated that the rice and Medicago truncatula cDNA sequences encode functional FAAH orthologs, and this was confirmed below using strategies similar to that described above for the Arabidopsis FAAH.

Using these three full-length, functional plant FAAH sequences to query non-redundant DNA databases, other plant orthologs were identified including those in barley, grape cotton, maize, potato, sugarcane, soybean, tomato and wheat (summarized in Table 4).

Table 4. Consensus (TC) identifiers prepared for the orthologous group of plant sequences that includes Arabidopsis, rice and Medicago truncatula FAAH sequences in this manuscript. Currently assembled as tentative ortholog group 520300 by The Institute for Genomic Research (tigr.org on the worldwide web), except for Medicago truncatula which not assembled into TC (AW695697 is a singleton). TCs built with available DNA sequences in various DNA databases including EST and other partial nucleotide sequences.

TABLE 4

Consensus (TC) identifiers prepared for the orthologous group of plant sequences that includes Arabidopsis, rice and Medicago truncatula FAAH sequences in this manuscript. Currently assembled as tentative ortholog group 520300 by The Institute for Genomic Research (tigr.org on the worldwide web), except for Medicago truncatula which not assembled into a TC (AW695697 is a singleton). TCs built with available DNA sequences in various DNA databases including EST and other partial nucleotide sequences.

| Plant | TC identifier | SEQ ID NO | % identity Arab FAAH | p-value | length |
|---|---|---|---|---|---|
| Arabidopsis | TC210025 | NO:15 | 100 | 0.00 | 2145 |
| Barley | TC111212 | NO:16 | 65 | 2.6e−91 | 1217 |
| Cotton | TC21641 | NO:17 | 71 | 1.1e−67 | 717 |
| Grape | TC36243 | NO:18 | 73 | 1.0e−143 | 1301 |
| Maize | TC230081 | NO:19 | 66 | 8.8e−26 | 377 |
| Potato | TC76474 | NO:20 | 64 | 2.0e−62 | 918 |
| Rice | TC188324 | NO:11 | 64 | 3.2e−132 | 1820 |
| Sugarcane | TC18099 | NO:26 | 65 | 1.4e−42 | 624 |
| Sorghum | TC87636 | NO:21 | 67 | 8.7e−30 | 439 |
| Soybean | TC179281 | NO:22 | 71 | 4.6e−51 | 552 |
| Soybean | TC199488 | NO:23 | 72 | 9.6e−53 | 554 |
| Tomato | TC117552 | NO:24 | 69 | 3.5e−75 | 859 |
| Tomato | TC132131 | None | 68 | 1.4e−166 | 1839 |
| Wheat | TC150217 | NO:25 | 64 | 3.6e−116 | 1589 |
| M. truncatula (single) | AW695697 | NO:13 | 71 | 4.0e−93 | 963 |

% identity is at the nucleotide level and the match length is provided over which the p-value was calculated.

EXAMPLE 12

Functional Expression of Rice and Medicago truncatula FAAH cDNAs in E. coli

Expression of recombinant candidate FAAH proteins as C-terminal fusions in pTrcHis2 and assays of NAE amidohydrolase (FAAH) activity was carried out as done as for the Arabidopsis FAAH (Shrestha et al., 2003). The rice (Os) and Medicago truncatula (Mt) cDNAs were expressed in E. coli (TOP10 cells) as His-tagged fusion proteins, with the lysates exhibiting NAE amidohydrolase activity similar to that of the Arabidopsis and Rat recombinant FAAH enzymes (FIG. 7A-7F). There was no amidohydrolase activity in lysates of *E. coli* harboring the rice (Os) or *Medicago truncatula* (Mt) cDNAs cloned in reverse orientation. Data in the figure are for the hydrolysis of NAE 18:2, but other NAEs such as NAE16:0 were equally suitable substrates for these recombinant enzymes, similar to the situation with *Arabidopsis* and rat FAAH. The data indicated that both the rice and *Medicago* cDNAs isolated and sequenced above encode functional FAAH enzymes.

EXAMPLE 13

*Arabidopsis* FAAH Encodes a Functional NAE Amidohydrolase In vivo

As a means to understand FAAH function in planta, transgenic and mutant *Arabidopsis* plants were generated and/or identified with altered expression of the *Arabidopsis* FAAH. Transgenic plants were generated with FAAH cloned downstream from the CaMV35S promoter in the sense orientation (as a FAAH:GFP fusion) or in the antisense orientation into appropriate pCAMBIA binary vectors. *Arabidopsis* plants were transformed by the floral dip method, and transgenic seedlings were selected on kanamycin. T2 and T3 seedlings from these selected plants were examined for their NAE amidohydrolase activity, NAE sensitivity, and phenotypic growth characteristics. Additionally, two T-DNA insertional mutants were identified with putative insertions in the At5g64440 gene. These lines were ordered from the *Arabidopsis* Biological Resource Center (Ohio State University), and seedlings were selected for growth on kanamycin. Plants from these seedlings were genotyped by PCR to determine zygosity, and homozygous mutant plants (no wildtype At5g64440 allele) were identified for biochemical and physiological experiments. The precise locations of the T-DNA inserts in the At5g64440 gene were confirmed by DNA sequencing of PCR products amplified with T-DNA and gene specific primers (insertion events summarized in FIGS. 8A-8C and 9A-9C). RT-PCR confirmed the lack of endogenous At5g64440 transcripts in the homozygous knockout lines. In the study equivalent amounts of total leaf RNA were used as template for AT5g64440 and EIF4A-2 specific primers. FAAH transcripts were somewhat lower than WT in antisense plants, and were not detectable in homozygous knockout lines, whereas most of the overexpressing lines showed higher relative amounts of FAAH transcript compared to WT without or with GFP C-terminal fusions.

Figure 10:
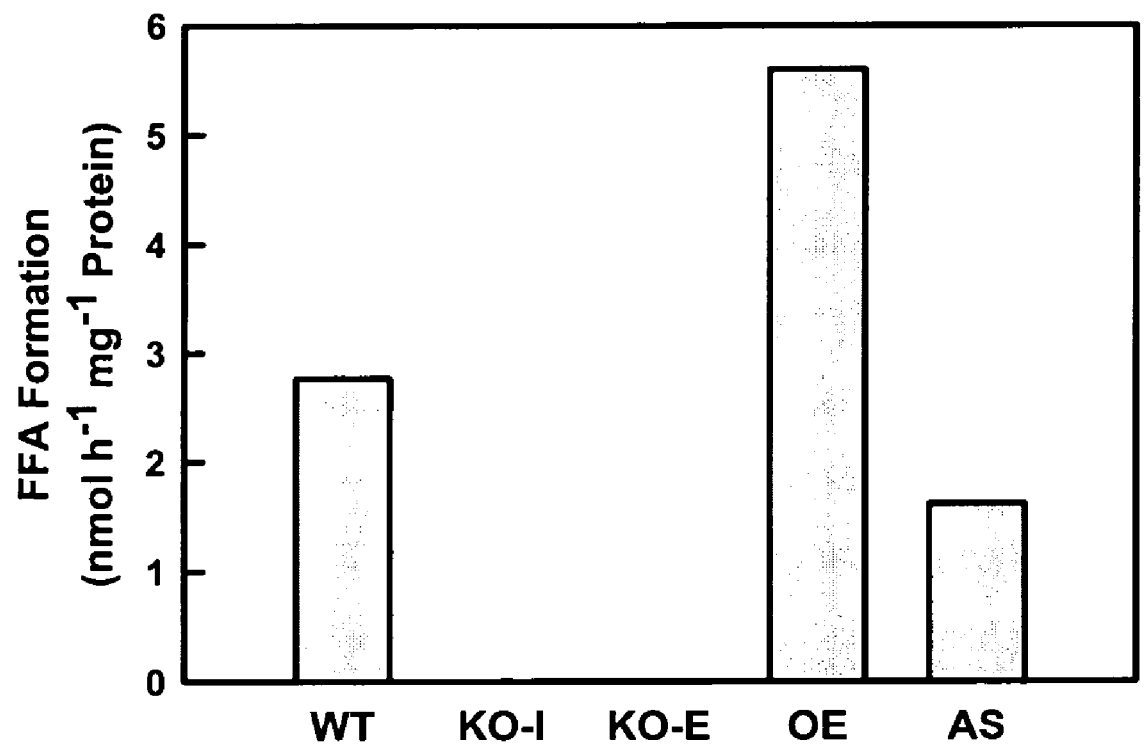
FIG. 10. NAE amidohydrolase specific activity in microsomes isolated from wildtype (WT), knockout (KO-I and KO-E), and transgenic (OE, overexpressors; AS, antisense expressors) *Arabidopsis* (Columbia background) plants. Enzyme activity was measured with equal amounts of microsomal protein extracts according to Shrestha et al., (2002) with [$^{14}$C]-NAE 18:2 as the substrate. Activity profiles were similar with assays of total homogenates, indicating that NAE amidohydrolase enzyme activity associated with microsomal membrane fractions represents the profile of the majority of active endogenous FAAH. Activity profiles were consistent with FAAH expression, such that antisense and knockouts have less or no activity compared with wildtype, whereas, overexpressors have more activity.

NAE amidohydrolase specific activity in microsomes isolated from wildtype (WT), knockout (KO-I, SALK__118043, and KO-E, SALK__095108), and transgenic (OE, overexpressors; AS, antisense expressors) *Arabidopsis* (Columbia background) plants was compared (FIG. 10). Enzyme activity was measured with equal amounts of microsomal protein extracts according to Shrestha et al., (2002) with [$^{14}$C]-NAE 18:2 as the substrate. Microsomes were isolated from above-ground tissues of six-week-old plants, all grown under the same environmental conditions. Activity profiles were similar with assays of total homogenates, supporting the conclusion that NAE amidohydrolase enzyme activity associated with microsomal membrane fractions represented the profile of the majority of active endogenous FAAH. Activity profiles were consistent with patterns of FAAH gene expression in these mutant and transgenic plants, such that microsomes from antisense and knockouts had less or no activity compared with wildtype, whereas overexpressors had more enzyme activity.

Seedlings were germinated and grown in MS-medium were continuously exposed to solvent-only control (0.5% DMSO), free fatty acid (FFA, as an inactive NAE12:0 analogue) or NAE 12:0, and the seedlings were photographed after 14 d growth. Composite images were taken from seedlings grown on different plates, and were representative of typical replicate experiments. Wildtype seedling growth was shown to be reduced by NAE12:0 treatment. The altered profiles of extractable FAAH enzyme activities in mutant and transgenic plants led to predictable differences in the sensitivity of seedlings to exogenous NAE 12:0 indicating a modified ability of these plants to metabolize NAEs. Seedling growth of *Arabidopsis* wildtype seedlings was inhibited by exogenous treatment of NAE12:0). This growth inhibition was greatly exacerbated when the FAAH gene expression was reduced, particularly in the knockouts, whereas FAAH overexpressors were essentially insensitive to NAE 12:0 application.

Figure 11A:
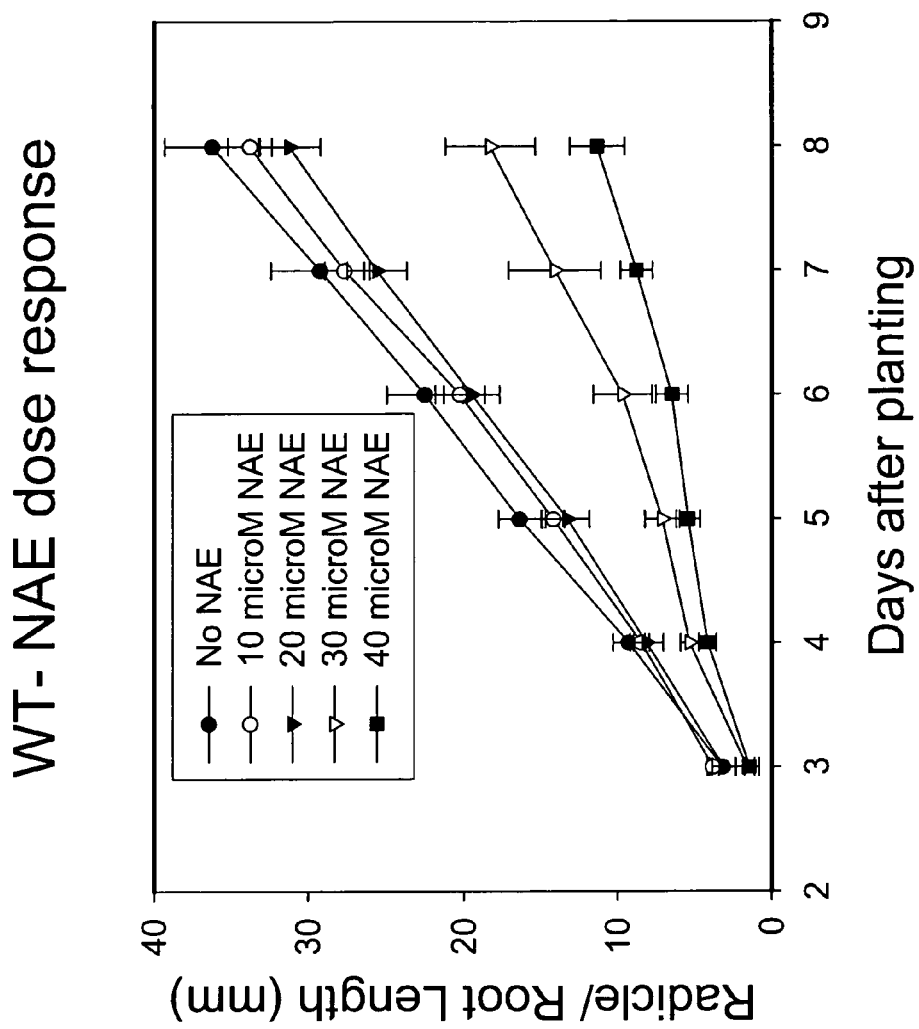
FIG. 11A-11C. Lengths of *Arabidopsis* seedling radicles/roots were measured daily after planting on MS medium that contained increasing concentrations of NAE 12:0. Data points are averages and standard deviation of 20 or more seedlings germinated and grown under identical conditions. There was a pronounced dose-dependent reduction in radicle/root length and elongation rate, similar to that shown previously (Blancaflor et al., 2003) for wildtype seedlings (FIG. 11A), and this seedling growth inhibition was more pronounced at higher NAE concentrations for both knockout lines (FIG. 11B and FIG. 11C).
Figure 11B:
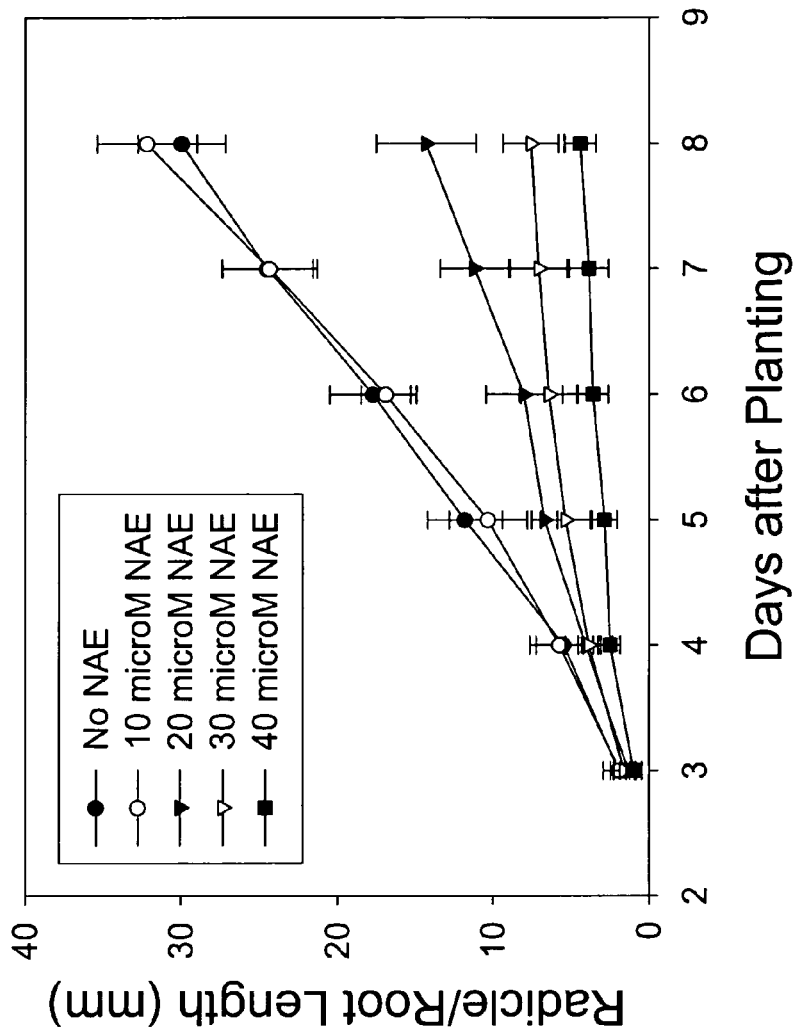
Figure 11C:
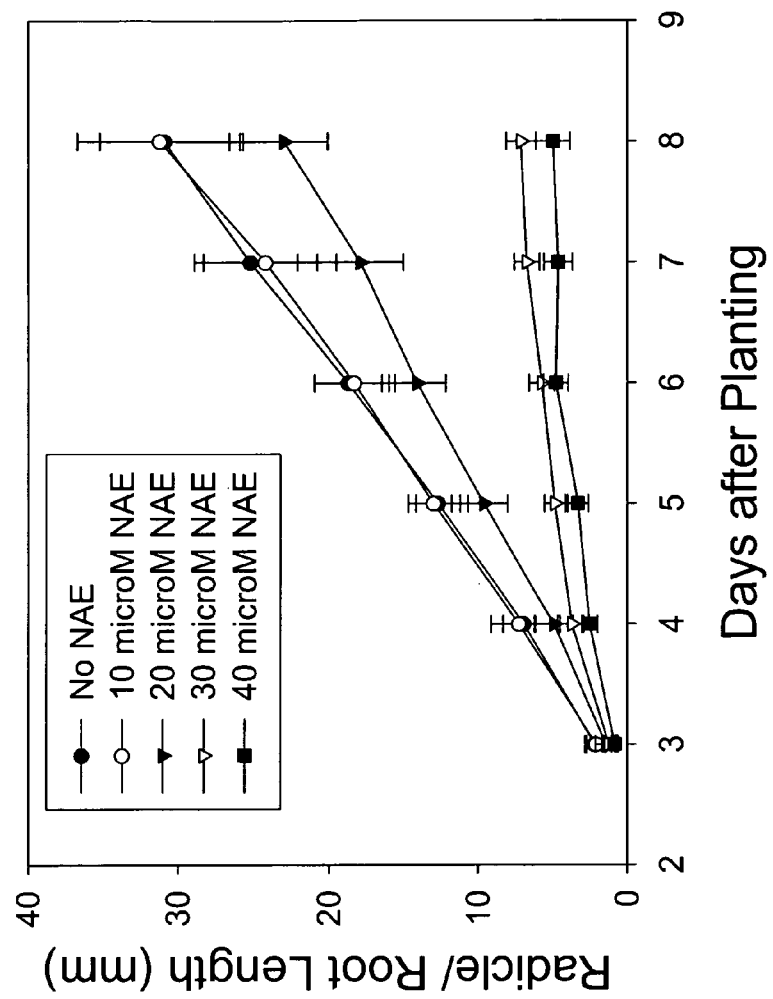
Figure 12:
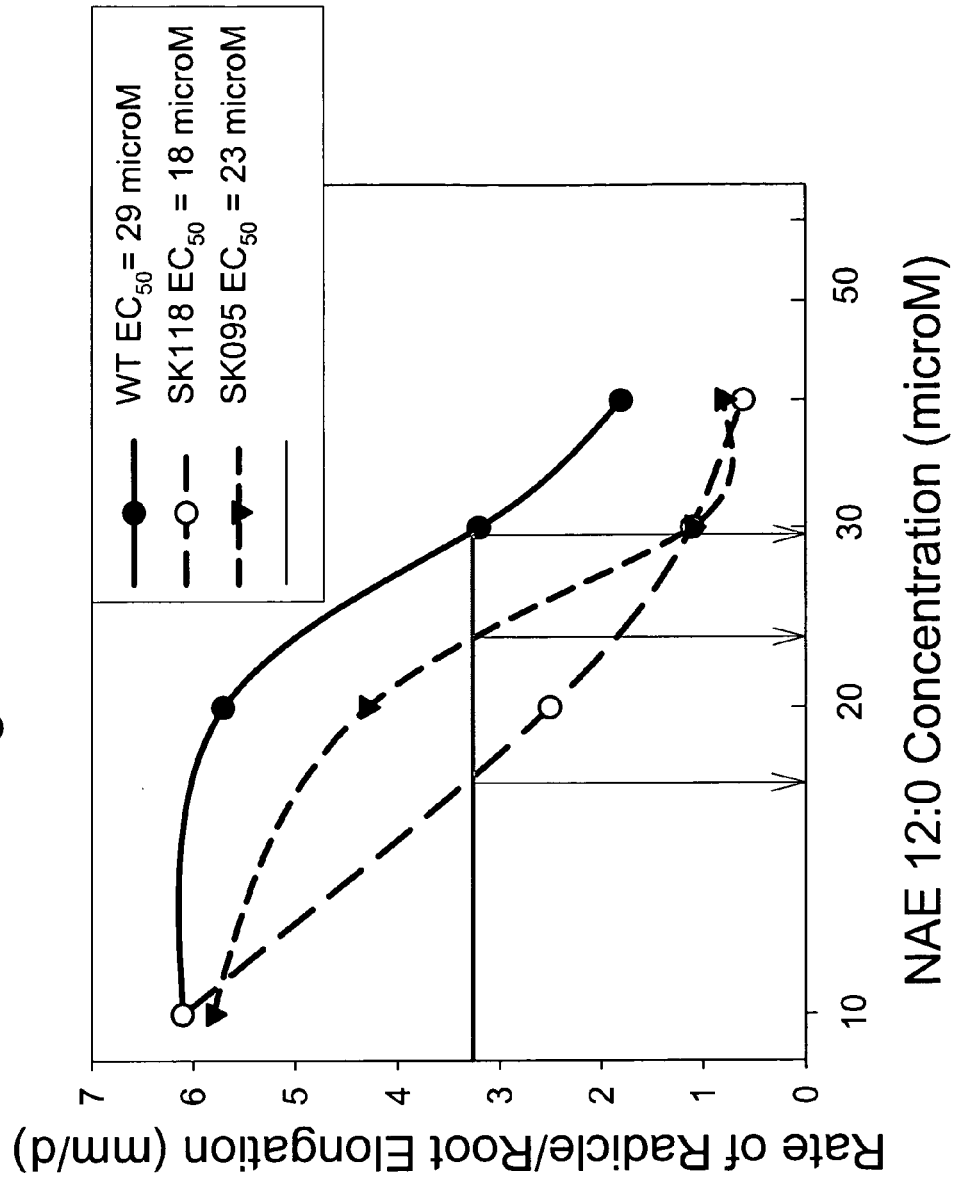
FIG. 12. The rate of root elongation was calculated by a linear regression of the data presented in FIG. 11, and plotted as a function of NAE concentration. Consistent with (Blancaflor et al., 2003) the concentration of NAE12:0 that reduced growth by 50% (EC50) was about 29 microM for wildtype seedlings, whereas the growth rate of both knockouts was more sensitive to exogenous NAE showing EC50's of 18 and 23 microM.
Figure 13:
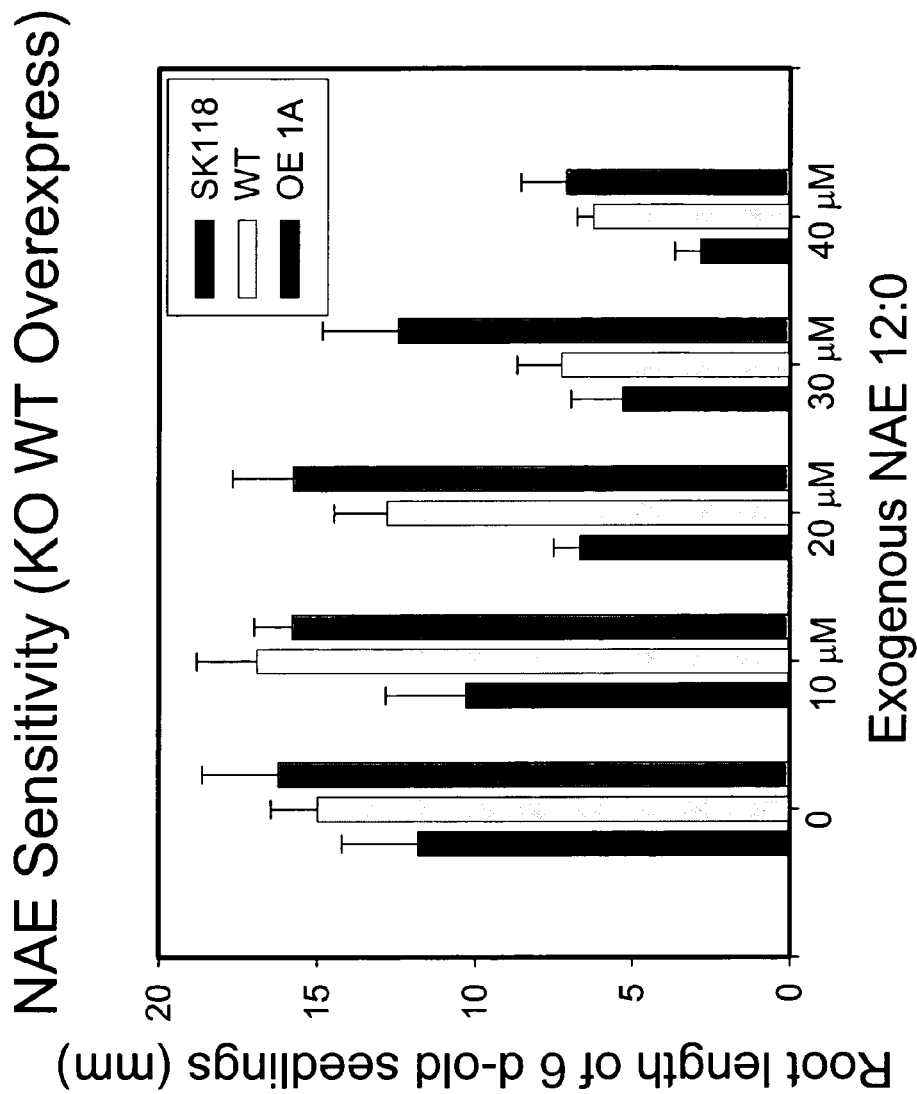
FIG. 13. Root lengths of 6-d-old *Arabidopsis* seedling germinated and grown in MS medium that contained increasing concentrations of NAE 12:0. Data points are averages and standard deviation of 20 or more seedlings germinated and grown under identical conditions. SKI 18, SALK homozygous knockout line 118043; WT, wildtype; OE 1A, over-expressing line with C-terminal GUS fusion ($^{35}$S:FAAH-GFP, #1a-1). Seedlings of At5g64440 knockouts were more sensitive to exogenous NAE compared with wildtype, whereas FAAH overexpressors were less sensitive to NAE 12:0 compared to wildtype.

Consequently the effects of NAE12:0 on plant growth and development can be altered predictably by altering FAAH expression. Additional quantitative data from *Arabidopsis* seedling root length measurements supported this link between At5g64440 gene function and seedling sensitivity to exogenous NAEs (FIGS. 11-13).

EXAMPLE 14

FAAH Influences Seedling Growth and Development

An analysis was carried out to the influence of NAE metabolism on regulation of seed germination and seedling growth. The profound dose-dependent effects of NAE12:0 on *Arabidopsis* seedling development described above supported this concept of NAE as a regulator of seedling development. Here, for the first time, a molecular-genetic association between seedling growth and endogenous NAE metabolism can be made.

Figure 14:
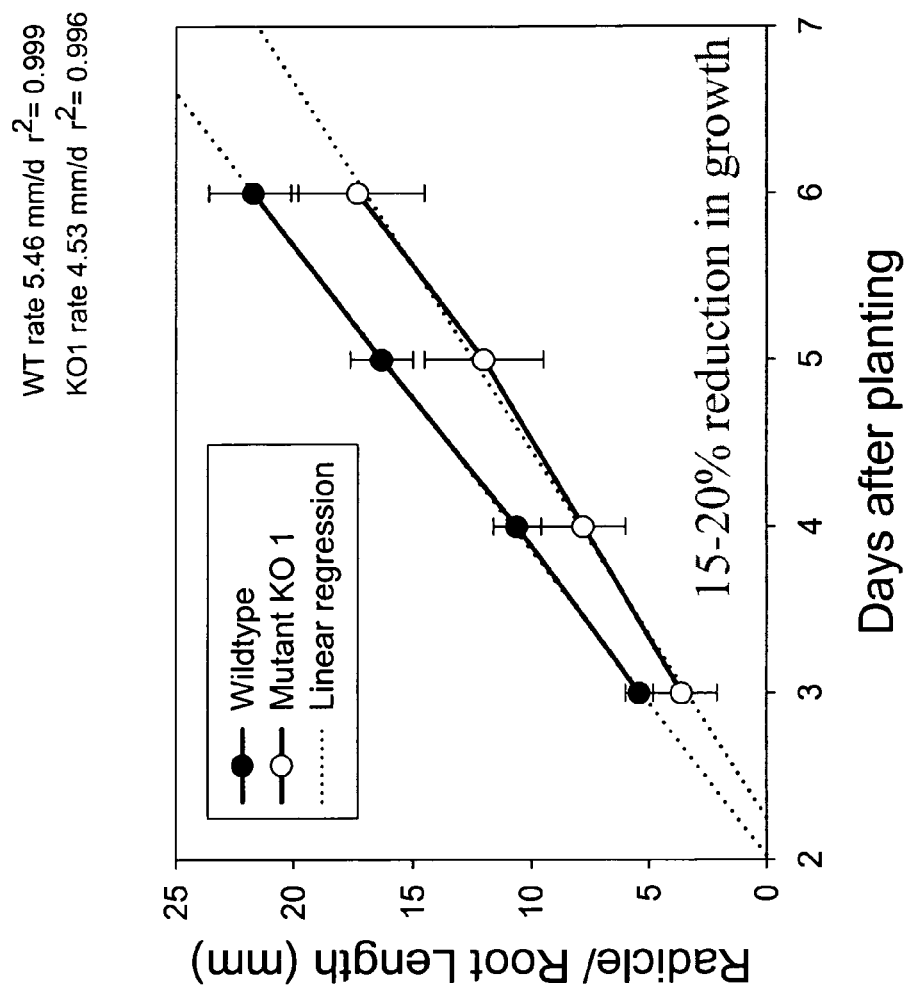
FIG. 14. Lengths of *Arabidopsis* seedling radicles/roots were measured daily after planting on MS medium. The FAAH knockout (KO1, SALK 118043) showed a significant reduction (p<0.0001) in primary root length and rate of primary root elongation compared to wildtype at all time points. Data points are averages of 20 or more seedlings germinated and grown under identical conditions (and from plants harvested at the same time). Data were compared with a student's t-test.

Phenotypic comparisons were made between *Arabidopsis* seedling roots of wildtype and At5g64440 knockout lines at 4-d after planting (FIG. 14). Although the timing of radicle emergence did not appear to be different between wild type and mutant seedlings, the rate of primary root elongation was reduced by 15-20% in the mutants (over 6 days postgerminative growth). Conversely, constitutive overexpression of the FAAH cDNA in transgenic seeds and seedlings appeared to accelerate seedling growth compared with wildtype seedlings. In this analysis, comparisons were made of *Arabidopsis* 8-d-old seedlings germinated and grown under identical conditions. Wildtype seedlings were compared to seedlings overexpressing the At5g64440 FAAH cDNA. The FAAH overexpressing seedlings appeared to have accelerated seedling growth compared to wildtype. The data collectively provided genetic evidence to support NAE metabolism and the At5g64440 *Arabidopsis* FAAH as an important pathway in the proper regulation of plant growth and development.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,302,523
U.S. Pat. No. 5,322,783

U.S. Pat. No. 5,384,253
U.S. Pat. No. 5,464,765
U.S. Pat. No. 5,508,184
U.S. Pat. No. 5,508,468
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
Abdullah et al., *Biotechnology*, 4:1087, 1986.
Altschul et al., *Nucleic Acids Res.*, 25:3389-3402, 1997.
Bates, *Mol. Biotechnol.*, 2(2):135-145, 1994.
Battraw and Hall, *Theor. App. Genet.*, 82(2):161-168, 1991.
Bevan et al., *Nucleic Acids Research*, 11(2):369-385, 1983.
Bhattacharjee; An; Gupta, J. *Plant Bioch. and Biotech.* 6, (2):69-73. 1997.
Bisogno et al., *J. Biol. Chem.*, 272:3315-3323, 1997.
Blancaflor et al., *Planta*, 217(2):206-17, 2003.
Boger et al., *Bioorg. Med. Chem. Lett.*, 10:2613-2616, 2000.
Bouchez et al., *EMBO Journal*, 8(13):4197-4204, 1989.
Bower et al., *The Plant Journal*, 2:409-416. 1992.
Bracey et al., *Science*, 298:1793-1796, 2002.
Bradford, *Anal. Biochem.*, 72:248-254, 1976.
Buchanan-Wollaston et al., *Plant Cell Reports* 11:627-631. 1992
Buckley et al., *Eur. J. Pharmacol.*, 396:141-149, 2000.
Buising and Benbow, *Mol Gen Genet*, 243(1):71-81. 1994.
Callis, Fromm, Walbot, *Genes Dev.*, 1: 1183-1200, 1987.
Casa et al., *Proc. Nat'l Acad. Sci. USA*, 90(23):11212-11216, 1993.
Chandler et al., *The Plant Cell*, 1:1175-1183, 1989.
Chang and Abelson, *Nucleic Acids Res.*, 18, 7180-7180, 1990.
Chapman et al., *Plant Physiol.*, 120:1157-1164, 1999.
Chapman, *Chem. Phys. Lipids*, 108:221-230, 2000.
Chebrou et al., *Biochim. Biophys. Acta*, 1298:185-293, 1996.
Christou; et al., *Proc. Nat'l Acad. Sci. USA*, 84(12):3962-3966, 1987.
Chu et al., *Scientia Sinica*, 18:659-668, 1975.
Conkling et al., *Plant Physiol.*, 93:1203-1211, 1990.
Cravatt and Lichtman, *Chem. Phys. Lipids*, 121:135-148, 2002.
Cravatt et al., *Nature*, 384:83-87, 1996.
Curnow et al., *Proc. Natl. Acad. Sci. USA*, 94:11819-11826, 1997.
Dalzell and Kerven, *J. Sci. Food Agric.*, 78:405-416, 1998.
De Block et al., *The EMBO Journal*, 6(9):2513-2518, 1987.
De Block, De Brouwer, Tenning, *Plant Physiol.*, 91:694-701, 1989.
Dellaporta et al., In: *Chromosome Structure and Function: Impact of New Concepts*, 18th Stadler Genetics Symposium, 11:263-282, 1988.
Desarnaud et al., *J. Biol. Chem.*, 270:6030-6035, 1995.
Deutsch et al., *Biochem. Pharmcol.*, 53:255-260, 1997.
D'Halluin et al., *Plant Cell*, 4(12):1495-1505, 1992.
Ebert et al., 84:5745-5749, *Proc. Nat'l Acad. Sci. USA*, 1987.
Elbing and Brent, *Curr. Prot. Mol. Biol.*, 1.2.1-1.2.2, 2002.
Ellis et al., *EMBO Journal*, 6(11):3203-3208, 1987.
Fowler et al., *Biochem. Pharmacol.*, 62:517-526, 2001.
Fraley et al., *Bio/Technology*, 3:629-635, 1985.
Fromm et al., *Nature*, 319:791-793, 1986.
Gallie et al., *The Plant Cell*, 1:301-311, 1989.
Gelvin et al., In: *Plant Molecular Biology Manual*, 1990.
Ghosh-Biswas et al., *J. Biotechnol.*, 32(1):1-10, 1994.
Giang and Cravatt, *Proc. Natl. Acad. Sci. USA*, 94:2238-2242, 1997.
Goparaju et al., *Biochem. Biophys. Acta*, 1441:77-84, 1999.
Hagio, Blowers, Earle, *Plant Cell Rep.*, 10(5):260-264, 1991.
Hamilton et al., *Proc. Natl. Acad. Sci. USA*, 93(18):9975-9979, 1996.
Hansen et al., *Chem. Phys. Lipids.*, 108:135-150, 2000.
Haseloff et al., *Proc. Natl. Acad. Sci. USA*, 94(6):2122-2127, 1997.
Hashimoto et al., *Biochim. Biophys. Acta*, 1088:225-233, 1991.
He et al., *Plant Cell Reports*, 14 (2-3):192-196, 1994.
Hensgens et al., *Plant Mol. Biol.*, 22(6):1101-1127, 1993.
Hiei et al., *Plant. Mol. Biol.*, 35(1-2):205-218, 1997.
Hillard et al., *J. Neurochem.*, 64:677-683, 1995.
Hinchee et al., *Bio/technol.*, 6:915-922, 1988.
Hou and Lin, *Plant Physiology*, 111:166, 1996.
Hudspeth and Grula, *Plant Mol. Biol.*, 12:579-589, 1989.
Ikuta et al., *Bio/technol.*, 8:241-242, 1990.
Ishidia et al., *Nat. Biotechnol.*, 14(6):745-750, 1996.
Jones, *J. Mol. Biol.*, 292:195-202, 1999.
Kaeppler et al., *Plant Cell Reports* 9: 415-418, 1990.
Kaeppler, Somers, Rines, Cockburn, Theor. *Appl. Genet.*, 84(5-6):560-566, 1992.
Katz et al., *J. Gen. Microbiol.*, 129:2703-2714, 1983.
Klee, Yanofsky, Nester, *Bio-Technology*, 3(7):637-642, 1985.
Knittel, Gruber; Hahne; Lenee, *Plant Cell Reports*, 14(2-3): 81-86, 1994.
Krogh et al., *J. Mol. Biol.*, 305:567-580, 2001.
Lamber, D. M., and Di Marzo, V. (1999) *Current Med. Chem.* 6, 663-674
Lambert et al., *Current Med. Chem.*, 9:739-755, 2002.
Lawton et al., *Plant Mol. Biol.* 9:315-324, 1987.
Lazzeri, *Methods Mol. Biol.*, 49:95-106, 1995.
Lee; Suh; Lee, *Korean J Genet.*, 11(2):65-72, 1989.
Lorz et al., *Mol Gen Genet*, 199:178-182, 1985.
Marcotte et al., *Nature*, 335:454, 1988.
Mayaux et al., *J. Bacteriol.*, 172:6764-6773, 1990.
McCabe, Martinell, *Bio-Technology*, 11(5):596-598, 1993.
McCormac et al., *Euphytica*, v. 99 (1) p. 17-25, 1998.
McGuffin et al., *Bioinformatics*, 16:404-405, 2000.
McKhann and Hirsch, *Plant Mol. Biol.*, 24(5):767-77, 1994
Murakami et al., *Mol. Gen. Genet.*, 205:42-50, 1986.
Murashige and Skoog, Physiol. *Plant.*, 15:473-497, 1962.
Nagatani et al., *Biotech. Tech.*, 11(7):471-473, 1997.
Nakai and Kanehisa, *Genomics*, 14:897-911, 1992.
Odell et al., *Nature*, 313:810-812, 1985.
Ogawa et al., *Sci. Rep.*, 13:42-48, 1973.
Omeir et al., *Biochem. Biophys. Res. Commun.*, 264:316-320, 2000.
Omirulleh et al., *Plant Mol. Biol.*, 21(3):415-428, 1993.
Ow et al., *Science*, 234:856-859, 1986.
Paria and Dey, Chem. Phys. *Lipids*, 108:211-220, 2000.
Patricelli and Cravatt, *J. Biol. Chem.*, 275:19177-19184, 2000.
Patricelli et al., *Biochemistry*, 38:9804-9812, 1999.
PCT App. WO 94/09699
PCT App. WO 95/06128
PCT App. WO 97/41228
Pertwee et al., *Eur. J. Pharmacol.*, 272:73-78, 1995.
Pertwee, *Prog. Neurobiol.*, 63:569-611, 2001.
Potrykus et al., *Mol. Gen. Genet.*, 199:183-188, 1985.
Prasher et al., *Biochem. Biophys. Res. Commun.*, 126(3): 1259-1268, 1985.

Reichel et al., *Proc. Natl. Acad. Sci. USA*, 93 (12) p. 5888-5893. 1996.
Rhodes et al., *Methods Mol. Biol.*, 55:121-131, 1995.
Ritala et al., *Plant Mol. Biol.*, 24(2):317-325, 1994.
Rogers et al., *Methods Enzymol.*, 153:253-277, 1987.
Sagasser et al., *Genes Dev.*, 16:138-149, 2002.
Sambrook et al., In: *Molecular Cloning-A Laboratory Manual* (second edition), Cold Spring Harbour Laboratory Press, 1989.
Sarker et al., *FEBS Lett.*, 472:39-44, 2000.
Schmid and Berdyshev, *Prostag. Leukotr. Essent. Fatty Acids*, 66:363-376, 2002.
Schmid et al., *Chem. Phys. Lipids*, 121:111-134, 2002.
Schmid et al., *Chem. Phys. Lipids*, 80:133-142, 1996.
Schmid et al., *Prog. Lipid Res.*, 29:1-43, 1990.
Sheen et al., *Plant Journal*, 8(5):777-784, 1995.
Shrestha et al., *J. Biol. Chem.* 278: 34990-34997, 2003.
Shrestha et al., *Plant Physiol.*, 130:391-401, 2002.
Singsit et al., *Transgenic Res.*, 6(2):169-176, 1997.
Sonnhammer et al., *Proc. Int. Conf. Intell. Syst. Mol. Biol.*, 6:175-182, 1998.
Spencer et al., *Plant Molecular Biology*, 18:201-210, 1992.
Stalker et al., *Science*, 242:419-422, 1988.
Sullivan et al., *Mol. Gen. Genet.*, 215(3):431-440, 1989.
Sutcliffe, *Proc. Natl. Acad. Sci. USA*, 75:3737-3741, 1978.
Thillet et al., *J. Biol. Chem.*, 263:12500-12508, 1988.
Thomas et al., *Plant Sci.* 69:189-198, 1990.
Thompson et al., *Euphytica*, 85(1-3):75-80, 1995.
Thompson et al., *The EMBO Journal*, 6(9):2519-2523, 1987.
Tian, Sequin, Charest, *Plant Cell Rep.*, 16:267-271, 1997.
Tiger et al., *Biochem. Pharmacol.*, 59:647-653, 2000.
Tingay et al., *The Plant Journal* v. 11 (6) p. 1369-1376. 1997.
Tomes et al., *Plant. Mol. Biol.* 14(2):261-268, 1990.
Torbet, Rines, Somers, *Crop Science*, 38(1):226-231, 1998.
Torbet, Rines, Somers, *Plant Cell Reports*, 14(10):635-640, 1995.
Toriyama et al., *Theor Appl. Genet.*, 73:16, 1986.
Tripathy et al., *Plant Physiol.*, 121:1299-1308, 1999.
Tripathy et al., *Plant Physiol.*, 131:1781-1791, 2003.
Tsuchiya et al., *J. Bacteriol.*, 171:3187-3191, 1989.
Tsukada; Kusano; Kitagawa, *Plant Cell Physiol.*, 30(4)599-604, 1989.
Twell et al., *Plant Physiol* 91:1270-1274, 1989.
Uchimiya et al., *Mol. Gen. Genet.*, 204:204, 1986.
Ueda et al., *Chem. Phys. Lipids*, 108:107-121, 2000.
Ueda, *Prostaglandis Other Lipid Mediators*, 68-69:521-534, 2002.
Van der Stelt et al., *J. Neurosci*, 21:765-8771, 2001.
Van Eck; Blowers; Earle, *Plant Cell Reports*, 14(5):299-304, 1995.
Vasil et al., *Plant Physiol.*, 91:1575-1579, 1989.
Walker et al., *Proc. Natl. Acad. Sci. USA*, 84:6624-6628, 1987.
Wang et al., *Molecular and Cellular Biology*, 12(8):3399-3406, 1992.
Wilson and Nicoll, *Science*, 296:678-682, 2002.
Yamada et al., *Plant Cell Rep.*, 4:85, 1986.
Yang and Russell, *Proc. Natl. Acad. Sci. USA*, 87:4144-4148, 1990.
Zheng and Edwards, *J. Gen. Virol.*, 71:1865-1868, 1990.
Zhou et al., *Plant Cell Reports*, 12(11).612-616, 1993.
Zukowsky et al., *Proc. Natl. Acad. Sci. USA*, 80:1101-1105, 1983.

What is claimed is:

1. An isolated nucleic acid sequence encoding plant fatty acid amide hydrolase, wherein the nucleic acid sequence is operably linked to a heterologous promoter functional in plants, and wherein the nucleic acid is further defined as selected from the group consisting of:
   (a) a nucleic acid sequence encoding the polypeptide of SEQ ID NO:2; and
   (b) a nucleic acid sequence comprising the sequence of SEQ ID NO:1.

2. The isolated nucleic acid sequence of claim 1, further comprised in a recombinant vector, wherein the nucleic acid sequence is in sense or antisense orientation relative to the heterologous promoter.

3. The isolated nucleic acid sequence of claim 2, further comprising at least one additional sequence chosen from the group consisting of: a regulatory sequence, a selectable marker, a leader sequence and a terminator.

4. The isolated nucleic acid sequence of claim 3, wherein the additional sequence is a heterologous sequence relative to the nucleic acid sequence.

5. The isolated nucleic acid sequence of claim 2, wherein the promoter is a developmentally-regulated, organelle-specific, inducible, tissue-specific, constitutive, cell-specific, seed specific, or germination-specific promoter.

6. The isolated nucleic acid sequence of claim 2, defined as an isolated expression cassette.

7. A transgenic plant transformed with a selected DNA comprising the nucleic acid sequence of claim 1, wherein the plant expresses the nucleic acid sequence.

8. The transgenic plant of claim 7, further defined as a monocotyledonous plant.

9. The transgenic plant of claim 7, further defined as a dicotyledonous plant.

10. The transgenic plant of claim 7, further defined as an $R_0$ transgenic plant.

11. The transgenic plant of claim 7, further defined as a progeny plant of any generation of an $R_0$ transgenic plant, wherein said transgenic plant has inherited said selected DNA from said $R_0$ transgenic plant.

12. A seed of the transgenic plant of claim 7, wherein said seed comprises said selected DNA.

13. A plant or bacterial host cell transformed with a selected DNA comprising the nucleic acid sequence of claim 1, wherein the cell expresses the nucleic acid sequence.

14. The host cell of claim 13, wherein said host cell expresses a protein encoded by said selected DNA.

15. The host cell of claim 13, wherein the cell has inherited said selected DNA from a progenitor of the cell.

16. The host cell of claim 13, wherein said host cell is a plant cell.

17. A method of altering the N-Acylethanolamine metabolism of a plant comprising introducing into the plant a recombinant vector comprising a nucleic acid sequence encoding plant fatty acid amide hydrolase operably linked in sense or antisense orientation to a heterologous promoter functional in plants, wherein the nucleic acid sequence is expressed in the plant, and the plant exhibits altered N-Acylethanolamine metabolism, and is selected from the group consisting of: (a) a nucleic acid sequence encoding the polypeptide of SEQ ID NO:2; and (b) a nucleic acid sequence comprising the sequence of SEQ ID NO: 1.

18. The method of claim 17, wherein the nucleic acid sequence encoding a plant fatty acid amide hydrolase is in sense orientation.

19. The method of claim 17, wherein the recombinant vector comprises the isolated nucleic acid sequence encoding a plant fatty acid amide hydrolase is in antisense orientation.

20. The method of claim 17, wherein fatty acid amide hydrolase is down-regulated in said plant and wherein the N-Acylethanolamine content of the plant is increased.

21. The method of claim 17, wherein fatty acid amide hydrolase is up-regulated in said plant and wherein the N-Acylethanolamine content of the plant is decreased.

22. The method of claim 17, wherein the growth rate of the plant is increased or decreased as a result of the expression of the isolated nucleic acid sequence, wherein up-regulating fatty acid amide hydrolase in said plant increases growth rate of the plant and wherein down-regulating fatty acid amide hydrolase decreases plant growth rate.

23. The method of claim 17, wherein fatty acid amide hydrolase is down-regulated and the stress tolerance of the plant is increased as a result of the expression of the isolated nucleic acid sequence.

24. The method of claim 21, wherein up-regulating comprises introducing a recombinant vector into said plant, wherein the recombinant vector comprises the nucleic acid sequence of SEQ ID NO: 1.

25. The method of claim 20, wherein down-regulating comprises introducing into said plant a recombinant vector encoding the plant fatty acid amide hydrolase in antisense orientation relative to the heterologous promoter operably linked thereto, wherein the plant fatty acid amide hydrolase nucleic acid sequence is selected from the group consisting of
- (a) a nucleic acid sequence encoding the polypeptide of SEQ ID NO:2; and
- (b) a nucleic acid sequence comprising the sequence of SEQ ID NO: 1.

26. The method of claim 17, wherein introducing the isolated nucleic acid comprises plant breeding.

27. The method of claim 17, wherein introducing the isolated nucleic acid comprises genetic transformation.

28. The method of claim 17, comprising up-regulating fatty acid amide hydrolase in said plant, wherein the stress tolerance of the plant is decreased as a result of the up-regulating.

29. The method of claim 20, wherein down regulating increases the expression of endogenous plant defense genes.

30. The method of claim 21, wherein up-regulating decreases the expression of endogenous plant defense genes.

* * * * *

SEQUENCE LISTING

<160> NUMBER OF SEQ ID NOS: 26

<210> SEQ ID NO 1
<211> LENGTH: 2165
<212> TYPE: DNA
<213> ORGANISM: Arabidopsis thaliana

<400> SEQUENCE: 1

```
cagtacaaga agcttaagat ttgaagctaa catataacat tcaagttccc aacaacttca      60
ccgctcatct ccgcacggct ttcttcattt agtaatcctt cgccggatcg gatcatcgtt     120
tctcagattc ctctttttaa gtttcttctt tcagatgggt aagtatcagg tcatgaaacg     180
tgcaagtgag gttgatcttt ctactgtcaa atataaagct gaaaccatga aagctcctca     240
tttgactggc ctttccttca agttgttcgt taatttgctt gaagcaccac ttataggctc     300
tttgattgtt gattatttga agaaagacaa tggcatgaca aagattttc gcaacacagt      360 tataccagaa gagcccatgt ttagaccgga gttcccatct caagaaccgg agcatgatgt     420
tgtcattgtt ggcgaagatg aaagtcctat agacagattg gaaacagcct tgaaatgtct     480
tcctcagtat gatccttctc gtagcttgca tgcagatcca gtgtcatctt tctggtactg     540
gaagattcgt gattatgcat atgcctatag atctaagctg acaactccat tgcaggtagc     600
aaaaagaata atctcaatca tagaggagtt tggctatgac aagcctccaa caccattttt     660
gattagattt gatgccaatg aagtcataaa gcaagctgaa gcttctacac ggaggtttga     720
```

```
acaaggaaat ccaatatctg ttttggatgg aatatttgtg acaatcaagg acgatattga      780
ttgtttaccc catccgacaa atggtggaac acatggctg catgaggatc gttctgtgga       840
gaaggattca gctgttgttt caaaactgcg ttcttgtggt gcaatcttac ttggcaaggc      900
aaatatgcat gagttaggca tggggaccac cgggaacaat tcaaattacg aaccacaag      960 aaacccgcat gatcctaaaa ggtacacggg cggatcttcc tcaggttcag cagctattgt     1020
agccgctgga ctatgttcag ctgctctagg aacagatggt ggaggttccg ttcgcattcc     1080
ttcagcactt tgtggtataa cgggactgaa gacaacatat ggtcggacag atatgacagg     1140
gtcattatgt gaaggtggaa cagtggaaat aattggtcca cttgcttcat ctctggaaga     1200
tgccttcttg gtgtatgctg caatcttggg ttcttcatct gctgatagat ataatttgaa     1260
accgagccca ccgtgttttc caaagttatt gtctcacaac ggaagcaatg caataggatc     1320
tctacgacta gggaaatata caagtggtt taatgatgtc agttcaagtg acatctctga      1380
caaatgcgaa gacatcctta agctcctatc aaacaatcac ggttgcaaag tggtggagat     1440
agtggttcct gaactggaag agatgcgtgc agcccatgtt atttcgattg ggtctccaac     1500
actgtcttct cttactccct actgtgaagc tgggaaaaat tcaaaactaa gttatgacac     1560
tcgtaccagc tttgcaattt tccgttcatt ctctgcttca gactatatcg ctgctcaatg     1620
tcttaggcga agattgatgg agtatcactt gaatatcttc aaagacgttg atgtcattgt     1680 gaccccctaca actggaatga cagctccagt gatacctcct gatgctctca aaaatggaga    1740
aaccaatatt caagtgacaa ctgatttaat gcgcttcgtt ctagctgcaa atctcctcgg     1800
cttccctgcc atatcagtcc cggttggtta tgataaagag gggcttccta taggattaca     1860
aataatggga agaccttggg ccgaagctac cgtccttggt ttagctgccg cagtcgagga     1920
actggctcca gttaccaaga aacctgcaat cttttatgat attctcaata caaactgaat     1980
tcataaggat cttccacaga actgaaaagg caaggattgt ctctggctgc ggaatattat     2040
ttatgtttac attatataag gttaatatgt caattgatct acaaatcgac gattattgtg     2100
ctataaaccg tgttggaatt tcttacgtcg actatgatta attttaaaag atgtgaatta     2160
gtctt                                                                 2165
```

<210> SEQ ID NO 2
<211> LENGTH: 405
<212> TYPE: PRT
<213> ORGANISM: Arabidopsis thaliana

<400> SEQUENCE: 2

Met Gly Lys Tyr Val Met Lys Arg Ala Ser Val Asp Ser Thr Val Lys
1               5                   10                  15

Tyr Lys Ala Thr Met Lys Ala His Thr Gly Ser Lys Val Asn Ala Gly
            20                  25                  30

Ser Val Asp Tyr Lys Lys Asp Asn Gly Met Thr Lys Arg Asn Thr Val
        35                  40                  45

Met Arg Ser His Asp Val Val Gly Asp Ser Asp Arg Thr Ala Lys
    50                  55                  60

Cys Tyr Asp Ser Arg Ser His Ala Asp Val Ser Ser Trp Tyr Trp Lys
65                  70                  75                  80

Arg Asp Tyr Ala Tyr Ala Tyr Arg Ser Lys Thr Thr Val Ala Lys Arg
                85                  90                  95

Ser Gly Tyr Asp Lys Thr Arg Asp Ala Asn Val Lys Ala Ala Ser Thr
            100                 105                 110

-continued

```
Arg Arg Gly Asn Ser Val Asp Gly Val Thr Lys Asp Asp Cys His
            115                 120                 125
Thr Asn Gly Gly Thr Thr Trp His Asp Arg Ser Val Lys Asp Ser Ala
130                 135                 140
Val Val Ser Lys Arg Ser Cys Gly Ala Gly Lys Ala Asn Met His Gly
145                 150                 155                 160
Met Gly Thr Thr Gly Asn Asn Ser Asn Tyr Gly Thr Thr Arg Asn His
            165                 170                 175
Asp Lys Arg Tyr Thr Gly Gly Ser Ser Gly Ser Ala Ala Val Ala
            180                 185                 190
Ala Gly Cys Ser Ala Ala Gly Thr Asp Gly Gly Ser Val Arg Ser
            195                 200                 205
Ala Cys Gly Thr Gly Lys Thr Thr Tyr Gly Arg Thr Asp Met Thr Gly
            210                 215                 220
Ser Cys Gly Gly Thr Val Gly Ala Ser Ser Asp Ala Val Tyr Ala Ala
225                 230                 235                 240
Gly Ser Ser Ser Ala Asp Arg Tyr Asn Lys Ser Cys Lys Ser His Asn
            245                 250                 255
Gly Ser Asn Ala Gly Ser Arg Gly Lys Tyr Thr Lys Trp Asn Asp Val
            260                 265                 270
Ser Ser Ser Asp Ser Asp Lys Cys Asp Lys Ser Asn Asn His Gly Cys
            275                 280                 285
Lys Val Val Val Met Arg Ala Ala His Val Ser Gly Ser Thr Ser
290                 295                 300
Ser Thr Tyr Cys Ala Gly Lys Asn Ser Lys Ser Tyr Asp Thr Arg Thr
305                 310                 315                 320
Ser Ala Arg Ser Ser Ala Ser Asp Tyr Ala Ala Cys Arg Arg Arg Met
            325                 330                 335
Tyr His Asn Lys Asp Val Asp Val Val Thr Thr Thr Gly Met Thr Ala
            340                 345                 350
Val Asp Ala Lys Asn Gly Thr Asn Val Thr Thr Asp Met Arg Val Ala
            355                 360                 365
Ala Asn Gly Ala Ser Val Val Gly Tyr Asp Lys Gly Gly Met Gly Arg
            370                 375                 380
Trp Ala Ala Thr Val Gly Ala Ala Ala Val Ala Val Thr Lys Lys Ala
385                 390                 395                 400
Tyr Asp Asn Thr Asn
            405

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
cattcaagtt cccaacaact tcaccgc                                          27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer
```

-continued

<400> SEQUENCE: 4
gtcgacgtaa gaaattccaa cacgg        25

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
atgggtaagt atcaggtcat gaaacg        26

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gtttgtattg agaatatcat aaaagattgc        30

<210> SEQ ID NO 7
<211> LENGTH: 2472
<212> TYPE: DNA
<213> ORGANISM: Rattus norvegicus

<400> SEQUENCE: 7

```
ggtttgtgcg agccgagttc tctcgggtgg cggtcggctg caggagatca tggtgctgag        60
cgaagtgtgg accacgctgt ctggggtctc cggggtttgc ctagcctgca gcttgttgtc       120
ggcggcggtg gtcctgcgat ggaccgggcg ccagaaggcc cggggcgcgg cgaccagggc       180
gcggcagaag cagcgagcca gcctggagac catggacaag gcggtgcagc gcttccggct       240
gcagaatcct gacctggact cggaggcctt gctgaccctg ccctactcc aactggtaca        300
gaagttacag agtggagagc tgtccccaga ggctgtgttc tttacttacc tgggaaaggc       360
ctgggaagtg aacaaaggga ccaactgcgt gacctcctat ctgaccgact gtgagactca       420
gctgtcccag gccccacggc agggcctgct ctatggtgtc cctgtgagcc tcaaggaatg       480
cttcagctac aagggccacg actccacact gggcttgagc ctgaatgagg gcatgccatc       540
ggaatctgac tgtgtggtgg tgcaagtgtt gaagctgcag ggagctgtgc cctttgtgca       600
taccaatgtc ccccagtcca tgttaagctt tgactgcagt aaccctctct ttggccagac       660
catgaaccca tggaagtcct ccaagagccc aggaggttcc tcagggggtg aggggctct       720
cattggatct ggaggtttcc ctctgggttt aggcactgac attggcggca gcatccggtt       780
cccttctgcc ttctgcggca tctgtggcct caagcctact ggcaaccgcc tcagcaagag       840
tggcctgaag ggctgtgtct atggacagac ggcagtgcag ctttctcttg gccccatggc       900
ccgggatgtg gagagcctgg cgctatgcct gaaagctcta ctgtgtgagc acttgttcac       960
cttggaccct accgtgcctc ccttgccctt cagagaggag gtctatagaa gttctagacc      1020
cctgcgtgtg gggtactatg agactgacaa ctataccatg cccagcccag ctatgaggag      1080
ggctctgata gagaccaagc agagacttga ggctgctggc cacacgctga ttccttctt       1140
acccaacaac ataccctacg ccctggaggt cctgtctgcg ggcggcctgt tcagtgacgg      1200
```

-continued

```
tggccgcagt tttctccaaa acttcaaagg tgactttgtg gatccctgct tgggagacct      1260
gatcttaatt ctgaggctgc ccagctggtt taaaagactg ctgagcctcc tgctgaagcc      1320
tctgtttcct cggctggcag cctttctcaa cagtatgcgt cctcggtcag ctgaaaagct      1380
gtggaaactg cagcatgaga ttgagatgta tcgccagtct gtgattgccc agtggaaagc      1440
gatgaacttg gatgtgctgc tgaccccccat gttgggccct gctctggatt tgaacacacc     1500
gggcagagcc acagggcta tcagctacac cgttctctac aactgcctgg acttccctgc       1560
gggggtggtg cctgtcacca ctgtgaccgc cgaggacgat gcccagatgg aactctacaa      1620
aggctacttt ggggatatct gggacatcat cctgaagaag gccatgaaaa atagtgtcgg      1680
tctgcctgtg gctgtgcagt gcgtggctct gccctggcag aagagctgt gtctgaggtt       1740 catgcgggag gtgaacagc tgatgacccc tcaaaagcag ccatcgtgag ggtcgttcat       1800
ccgccagctc tggaggacct aaggcccatg cgctgtgcac tgtagcccca tgtattcagg      1860
agccaccacc cacgagggaa cgcccagcac agggaagagg tgtctacctg ccctccctg       1920 gactcctgca gccacaacca agtctggacc ttcctccccg ttatggtcta ctttccatcc      1980
tgattccctg cttttatgg cagccagcag gaatgacgtg ggccaaggat caccaacatt      2040
caaaaacaat gcgtttatct attttctggg tatctccatt agggccctgg gaaccagagt      2100
gctgggaagg ctgtccagac cctccagagc tggctgtaac cacatcactc tcctgctcca      2160
aagcctccct agttctgtca cccacaagat agacacaggg acatgtcctt ggcacttgac      2220
tcctgtcctt cctttcttat tcagattgac cccagccttg atggaccctg ccctgcact       2280 tccttcctca gtccacctct ctgccgacac gccctttta tggctcctct atttgttgtg       2340
gagacaaggt ttctctcagt agccctggct gtccaggacc tcactctgta gatgaggctg      2400
gctttcaact cacaaggctg cctgcctggg tgctgggatt aaaggcgtat gccaccacaa      2460
agaaaaaaaa aa                                                          2472
```

<210> SEQ ID NO 8
<211> LENGTH: 8793
<212> TYPE: DNA
<213> ORGANISM: Oryza sativa

<400> SEQUENCE: 8

```
atgacgccgg tggaggaggt ggacctgtcg gcggtgaggt accagtcgcc gtcgctgcag       60
gcgccgcacc tcaccggctt ctctctcagg gccttcgtct ggctcatgga gtcgcccta      120 ttcggccgcc tcctcacctc cgtcctcaag tcgcagaaca acatcacaag ggtacgttgg     180
gtattagctt tgcctaatta aatttgctac tatgctaata atgaattgat ggtgatgaat     240
ttttggtgtt tgatgcactg cacgcaccgc agatgctgca ggacacggtg atccccgagc     300
gccccatgta cctccccgag tacccgccgc agggtatgcc tagtatacta tatcccacct     360
tccatagcat tcccaatttc atattccttt ccttcctgct tcactttatt acccaaacat     420
tctcatcatc aaatagttat tatactaaat gtccggtatc gctaatccta gttcgagcgc     480
cgcacaatgc tccctcgttc gttttttcgt ttttttttacc accccacctt ctgtgtttct     540
tttttctctt ttccatctta tctgtgcttc atcaaaggac ccggtaaaat attaaccatc     600
cgtttagttt ttcttttccaa gttcattttt ctaatgtttc acaacgtttt aaaagtaacg    660
aatttacttt gtggagtttt tcaaaagtaa cgaatttact cgcatgaatg cccctttcaa     720
aagtaacaaa tttacttgca caaatgccct cacattgtat gtgcatcatt cctagatggt     780
cgtaaaagaa tacctaacaa atttacttgc acgaatgccc tcacattgta cgtgcatcat     840
```

```
tcctagatga tcgtaaaaga ataccagtgt tataaatatt atttagattt cgtggtctgc    900
gactaaaata attaccaccg tcctctcaat atagcccatg atctcgtagc caccatgtag    960
taatatgttt actaatgtgt ttaatacaca gtataagggt aaaaactgag gcttcgtggt   1020
ctgcgagtaa acaattacc accctctctc tatatagccc atgatctcgt atccactatg   1080
tagtaatatg tttactggtg tgttcaatat acagtataaa aagtaaaaac tgatactaag   1140
agtattgtta gtctgtatca caaaatggcc gtacgaatga aaaaaattac aggctcaatc   1200
acacacaagt gataagatta ctcacaggtg aatcaaacta gaaagaaaaa aaaagattc    1260
atccaaaaat ccatcgtgaa actacatcct ggtggctttg ctggatcttg ctataaggat   1320
ggagaggctg gtctgtgtct tgtgactggt agtggagaga gcaaccgagt ggcgaacggt   1380
acgcgacgat ggaatcaagg gaggatgtag cagcatggta tagagatggg ctcgacgttg   1440
cgcagtagca gccatccatc atctagcaag cgcaaaaaaa aagcaaaaac attattgttc   1500
atgtcataga gacgacgagc aaatgaaaaa tagcaaacaa cctccatcac tggcggactc   1560
caccttgtcc tgcggccagc cacatggagc acgatgtgca aatgtaggat ctgtgcagac   1620
catcaattca gatcaggtaa tattgcagat tacacgttaa tttgatttgc aaaaagaaat   1680
tgggcttca tacgtgaagt tgaaggagag tatgcagatg caaatcggag tgtcatttcc    1740
atacttgctt gttctatcaa cgtcgccgat gtggagcagc cgccggttgt tgctcttgac   1800
ccaggtgaac acctccttgc cgattaagct gtgccttcgc ctcaaccgcc gccggtcacc   1860
gccgtcaacc gccacggtgt cgtcatcctc gtccatggtg tgttaccgat ctgtaggcta   1920
ggatggtgga tcgattcaga ttcgaagaaa aaagaaaaa atgaagtggg ggcaagagtg    1980
gttggttggg tacgggaaaa atagaatata taccagaagc agagaagttg tttttatcgc   2040
agtaaatcat taactccgat aatagtggga gcaggatgac gggacgtggg gtgggatcga   2100
aagcagggaa gttgttttta ttatcgaagt aaatcgttta ctccgataac ggtgggagtg   2160
ggatgacggg acgtggggtg aggtgggcct ggactaatac atgtttggcg ctcggaatac   2220
taggaacgtg ctgcgctcct aattgtagta ctattaaatg tcttacaaaa aacaaacaaa   2280
agatttgctc ctttaagtac catcaaacat caaacatgct gctgcaaaac cacaccttaa   2340
accctctgcc cctgtctatt ttccttgcaa tccatttgtt ttcttaccca tatttttgt    2400
acactactgc tgtggtgctc acatttggaa ctggtgctgc tttgccagag ccggagcaag   2460
gagttttgct tctgggggat gacagggacc ctgtggacag agttgaggaa gcacttcact   2520
gcctcccgcc ctatgatccg tctctgcgtt ggccggccgg ggacaaaccc cctttcctct   2580
actggaagat ccgtgatttt gcgcatgcgt accgctccgg gatcacaacc ccgtctgttg   2640
tcagtagccc cattggattg aacaaatcat tattttcttc tctgcctccc ctcctgcatg   2700
tgtgccactt gactttcttc ttgttgcata ggttgcggag catatcattg ccggtgtgga   2760
agagtggagc aacaagaagc ctcccatgcc tatgttggtt tatttttaacg cagatgatct   2820
aaggaaacaa gctgaagctt ccacaaagag atttcagcaa ggtttttccct tctctaaaat   2880
catgatattt ttgtattgtt gacttttta tatatatatt tgggttaaat actttcaaat    2940
tgaaactcca ccatattcta tctcatcttc ttgacatgtg atggtgctcc ttggctcagg   3000
aaacccaatt tccatcttgg acgggatctt tatcgccatt aaggatgaca ttgactgctt   3060
cccatatcca tcaagggtt agttaacaga ctgaagggc ctggcaattt ggttgctgta    3120
tctgagaagc gtattccaac ttataccttt ttttaaaaa aaatacaggt gctactacat   3180
```

-continued

| | |
|---|---|
| ttttcgacaa aattcgctct gtggagaaag acgcagtttg tgttgctcgt ttgcggaaat | 3240 |
| gtggagtgtt attcattggg aaagctaata tgcatgagct aggccttgga gtaactggaa | 3300 |
| acaatccaaa ctatgggtat gcattatcat catgtgactg cttatttgt tcagatccct | 3360 |
| tagctagtat ctagggagca cctgacggtt tgtgtggtca caaatgagaa atatcaacaa | 3420 |
| cattttcaag gccaaacaga ctgtattatt ttattagctg tttcctagaa tcaaattaaa | 3480 |
| ttgagcatta gtaaatctag ttgactaacc aaagtactgg gatgaaaata aatattttga | 3540 |
| gctatatcag tcacatccaa atcaacaca ttttttaaa agattaggaa ttcaaaattt | 3600 |
| tgatccaatc ttaagtgata gtccaattta ctgttttctg atgcctagtg tagtgcttaa | 3660 |
| ccatcttgtt tcttaacctt tccatttgca gaacagcaag aaatccacat tcaattgata | 3720 |
| gatatactgg tggttcttca tcaggtccag ctgcactagt ctcatcaggg ttatgctcag | 3780 |
| cagcaattgg aacagatggt ggaggtctgt acataagctt cattgcccct agattcttgt | 3840 |
| gttgtctgta ctagtctcca gctactactt tttttactgt gacaggttct gttaggatac | 3900 |
| catcttctct atgtggcatt attggtttga agacaaccta cggacggaca gatatgactg | 3960 |
| ggtaactaaa agaagttaga attcacttaa tatttactgt agtaactcct ttgagcatca | 4020 |
| taattcaaat cgattataaa tttataatag atttcaacat cacatctata gacgatatag | 4080 |
| ccctctgcta acattccaga agttctgaaa ctgttttcta ttatggaagt tattaaaaac | 4140 |
| aatgaaataa aggacgagtt gttttttat ggctatccta cacctgatca tattacaata | 4200 |
| tatttacatg catcctatta gaagtatgtg taattagaga ttctgctttc agggcacttt | 4260 |
| gtgattgtgg gaccgttgaa gttgcttctc ctctagcagc ttcagtggag gatgctttgc | 4320 |
| tagtgtaagc tatttacctt gctagagaga tcatgagatc tgagatcatt tgcacaagtc | 4380 |
| tgttaggctt acgtttcttg ccaattaagc gtgaagtttg tcgacactat ttttccatga | 4440 |
| tataaatgat cttgtaagct tgactgtcat cttaatgaac tgacttttca ggtattctgc | 4500 |
| aatagcaggc tctaggccta tggataagct taccctgaga ccagtaagat atttatgatg | 4560 |
| tactttttc atcttcctgt taaataccac aacctactaa taaattggat aggtaacacg | 4620 |
| ataattgact gcaaaacaga gaattgtggc tggctggttc attcttcctt gggccatatg | 4680 |
| accagctgcc cagtcatagc atctaggcag tttgctactt cctccgtttc atattataaa | 4740 |
| actttctagc attactcaca ttcatatata tgttaatgaa tctagacata tatgtgtgcc | 4800 |
| tagattcatt aacatctata tgaatgtctt ataacctgaa acggaggtag tattttttat | 4860 |
| atgagggac aatattgtct gtttactgat tgatatagca tactgcaatg ttttattttt | 4920 |
| tttaaaaaag ttaaatgtta atctacatc gtaatacagc caaatgttta gcttcttaat | 4980 |
| tgtccctgg aattcacatt tgatatcgat cttaaagcaa cctgtcaagc tcacatcttc | 5040 |
| tgcatttctt tccatttcct ctctacagtc accgctctgt gtccctaatt tggtgtctcc | 5100 |
| tgacaacaac aatatactgg gatcggtgaa aataggaaaa tatactgagg taaacttttc | 5160 |
| acatcaagca tcattttggt atgcatgagc ctgttctaaa ttacactggt ttttgtagtg | 5220 |
| gtttcatgat gtctccgatc gtgatatctc taatacatgt gaggatgcac ttaaccttct | 5280 |
| ttgcagcagc ttcggatgtc aagtaagatc atcactatct aacataccttt agacaatagg | 5340 |
| agtacagtat tctactagtt aattatcaca gtttatatat agcagcaaca ataggccttt | 5400 |
| gcttttggtt gtgcaatttc ttctattaat ggcaacatgt tttattgtgt ggttttctgt | 5460 |
| ttttttcctta ctgatgtgac attccaatgt gtacagatat ttctatgtgc atcaattgca | 5520 |
| ttatcgataa tggatatgtt gaaataactg tgaaatataa atgatatgtt tatttttta | 5580 |

```
attctgtaaa tcataattgg tttataattg attactgagc tgctttatct ggagctttta    5640
ggaagctaat gagttgtatg agttacgctt aaacttttc cagctacgaa atgtttgaat     5700
gagagccaat tataatgatg tgttcctgta aaaattttct gtcatgtaag ttgataagat    5760
tttatttatg tgtttaaaga tagaagaaat aatactgcca gaacttgagg agatgcgtac   5820
tgcccatgtt gtctcaattg gcacagaatc attctgtgat ttgaatcctc attacagagc   5880
agggtacaca tctattttaa tgaatatcat attctacatg ttgttctgag atataatttt    5940
tgaaatttcc ttcaggaaat agtgtgtttg ctgttctgta gtaatgatct tctgctaatt   6000
tcctccagaa aacgaactga atttacgtta gacactcgaa caagtttggc acttttgga    6060 tcattcactt cgactgacta tgttgcttct caacgaataa ggtgagtaaa gggtatacat   6120
tcagctgatg catagatttt tctatttctg atgcaattta gtctaaagca taaatcatat   6180
gctgctgacc tattattgaa gtgagcacca ggggatgctg attttgtgc tatcttattc    6240 ttcttgtatg atgtctccta tattgtgcta aatgtaacgg ggcatgttta ggagaaggat   6300
aatgtactat cacaatgaag ctttcaagaa ggttgatgtc atagcaactc ctacaactgg   6360
gtaataaatc cacaaatttc atcataatca atctgtacat cttaccactt gctcttacta   6420
atttgatgca tacttcctcc tccatctatt atcttttgct tactcaagca ggccagtgca   6480
caatggaagt ttgtagtttt cagtcacaag tatttctaag caatgtccat ttgacaattt   6540
tctgatagtt gtggcaaaca ccatttggac gatcatgttt tggaaaatga aaactgcgtt   6600
aatcctgagt ctcgattcct ggacatgaac actgtgtcag ttcatctgcc tcatcatgtt   6660
gaagagttta acctgctgtt acctgttatt agtcttacga ttcaaagatt gatcaatgtt   6720
cttatgctca tgcacaatga caaccctaat tgtgaaaagt agaatgtaga agatatctag   6780
tgtgtctgga aggactttaa actttcttat atcaaatcaa gttcttacag taatgcaaat   6840
ggtctggctt tgtgttgtgg ataaatggtt gacctggtat tttctacatt aaatgaacat   6900
tatgttatat atctgagaat tgccctgtgg caatacagtt cagaatggac tggaatagtt   6960
aaaattaact aatctgtaag tatttgtcta tactccatag cacatagatg atgcatctct   7020
tgtctactgg taatactgca ttctagaact tttacatatt ttgcctttt agcgagatgt    7080 attttctgtt gctaaaacag ctaaggaaat tttgttgttt ctccagcatc actgctccag   7140
aaataccaca aagttctctg aagttaggag agtccaatta cgttgtgtca ggtaaacagt   7200
ttggaggaca ttttctcttg gtatcttcat tagctatttt gcctgtttac ctgtgcgaaa   7260 tcatagctttt aagttgaga aaaccagaaa tcaggacgcg tcaattgtta tttgatcatg    7320
tcatgtttct attttgcatt tatatgatgcc tgtatagggg caggtttggt aaggtggcaa   7380
gccaaacact ccatcaaaac cttatttacc aaaattttgg gaatgtccat gtactcgtct   7440
tgtattatca aaattttggc actaagcaca aaaaaggcc ttctctacct cttccaaata    7500
atcctagggt ggagaaccta accgttctat aagtcgttca gtttgaacaa ggaaaatttt   7560
gtagggaggc ttcttattct ttgtagcagg aatcatgtaa acaaggaatc tttgttcctg   7620
tctggattga tatacaactt agttacacaa cttagaagta acaagtccat catctttcat   7680
ctataagtga cttgaattaa agtgcatatg tatgcctgtt ttgatgctaa ctacaaattt   7740
ggctattttc ttctgtatat agaccatgca aaacttttt tgtctgacac cgccgcttca    7800
ttgcagctta cctgatgcga ttcgtgatag ctggcaatct tcttggtttg cccgcgataa   7860
ctgtacctgt aagttgtgca aactcatggt tatgttttat gtatgtattg catctttcct   7920
```

-continued

| | | | | |
|---|---|---|---|---|
| ttaaaaacga | agagcatgta | ctgcatgttt | aacttagcat | tctgcatgaa | gtgaattttg | 7980 |
| gataagagtg | attcataaat | attttgctta | aatactgtca | ttatttccaa | tagagaagaa | 8040 |
| ttttctcagg | gttggatttt | ttgttcagta | actgaatatc | tttaaaaggc | gcacttgttc | 8100 |
| tatatgttac | tacttctgga | ctcaggttgg | tcatgataag | caagggcttc | ctataggctt | 8160 |
| gcaactgata | ggtcgaccat | ggggcgaggc | tagcttatta | agggtggctt | ctgcaatcga | 8220 |
| ggtattgtgc | aactacatca | taaatattaa | atatcgtgtt | tgggtttctc | ctgcagcaag | 8280 |
| tctagattgg | actgttctta | gtatgaatcc | tgatgaatat | ctgaacattt | tcaagacagt | 8340 |
| ccactatatt | tggcccttc | attgcaagtt | tacctctaat | tcttgtgaaa | acttatatat | 8400 |
| atttctatag | cacttgttac | tgcaattctg | agtagtacca | tgaacttaga | aagttttcta | 8460 |
| ttagtattat | tatttttat | ttatcttctt | aaattgtctt | gtttcattgg | tgtgccaact | 8520 |
| gcattttggt | attttccacc | ccattagaat | ttattttca | gttggaggtg | catttccaat | 8580 |
| atggcaatat | aaatacaagt | attatgattg | tgcattactt | ggagtattct | tcttttaatg | 8640 |
| gtctagccac | ataatccaaa | gtccaatagt | taaattatct | gctgatgcta | aagaatcgg | 8700 |
| tgtacagctg | acgttggttg | tgcctgcttg | taggagctct | gtctgcagaa | gcggaaacgg | 8760 |
| ccatctgcat | ttcatgacat | cctgaacgct | tga | | | 8793 |

```
<210> SEQ ID NO 9
<211> LENGTH: 1737
<212> TYPE: DNA
<213> ORGANISM: Oryza sativa

<400> SEQUENCE: 9
```

| | | | | | |
|---|---|---|---|---|---|
| atgacgccgg | tggaggaggt | ggacctgtcg | gcggtgaggt | accagtcgcc | gtcgctgcag | 60 |
| gcgccgcacc | tcaccggctt | ctctctcagg | gccttcgtct | ggctcatgga | gtcgccccta | 120 |
| ttcggccgcc | tcctcacctc | cgtcctcaag | tcgcagaaca | acatcacaag | gatgctgcag | 180 |
| gacacggtga | tccccgagcg | ccccatgtac | ctccccgagt | acccgccgca | ggagccggag | 240 |
| caaggagttt | tgcttctggg | ggatgacagg | gaccctgtgg | acagagttga | ggaagcactt | 300 |
| cactgcctcc | cgccctatga | tccgtctctg | cgttggccgg | ccggggacaa | accccctttc | 360 |
| ctctactgga | agatccgtga | ttttgcgcat | gcgtaccgct | ccgggatcac | aaccccgtct | 420 |
| gttgttgcgg | agcatatcat | tgccggtgtg | gaagagtgga | gcaacaagaa | gcctcccatg | 480 |
| cctatgttgg | ttttattaa | cgcagatgat | ctaaggaaac | aagctgaagc | ttccacaaag | 540 |
| agatttcagc | aaggaaaccc | aatttccatc | ttggacggga | tctttatcgc | cattaaggat | 600 |
| gacattgact | gcttcccata | tccatcaaag | ggtgctacta | cattttcga | caaaattcgc | 660 |
| tctgtggaga | agacgcagt | ttgtgttgct | cgtttgcgga | aatgtggagt | gttattcatt | 720 |
| gggaaagcta | atatgcatga | gctaggcctt | ggagtaactg | gaaacaatcc | aaactatgga | 780 |
| acagcaagaa | atccacattc | aattgataga | tatactggta | gttcttcatc | aggtccagct | 840 |
| gcactagtct | catcagggtt | atgctcagca | gcaattggaa | cagatggtgg | aggttctgtt | 900 |
| aggataccat | cttctctatg | tggcattatt | ggtttgaaga | caacctacgg | acggacagat | 960 |
| atgactgggg | cactttgtga | ttgtgggacc | gttgaagttg | cttctcctct | agcagcttca | 1020 |
| gtggaggatg | ctttgctagt | gtattctgca | atagcaggct | ctaggcctat | ggataagctt | 1080 |
| accctgagac | catcaccgct | ctgtgtccct | aatttggtgt | ctcctgacaa | caacaatata | 1140 |
| ctgggatcgt | tgaaaatagg | aaaatatact | gagtggtttc | atgatgtctc | cgatcgtgat | 1200 |
| atctctaata | catgtgagga | tgcacttaac | cttctttgca | gcagcttcgg | atgtcaaata | 1260 |

-continued

```
gaagaaataa tactgccaga acttgaggag atgcgtactg cccatgttgt ctcaattggc      1320
acagaatcat tctgtgattt gaatcctcat tacagagcag gaaaacgaac tgaatttacg      1380
ttagacactc gaacaagttt ggcactttt ggatcattca cttcgactga ctatgttgct       1440
tctcaacgaa taagcatcac tgctccagaa ataccacaaa gttctctgaa gttaggagag      1500
tccaattacg ttgtgtcagc ttacctgatg cgattcgtga tagctggcaa tcttcttggt      1560
ttgcccgcga taactgtacc tgttggtcat gataagcaag ggcttcctat aggcttgcaa      1620
ctgataggtc gaccatgggg cgaggctagc ttattaaggg tggcttctgc aatcgaggag      1680
ctctgtctgc agaagcggaa acggccatct gcatttcatg acatcctgaa cgcttga        1737
```

<210> SEQ ID NO 10
<211> LENGTH: 578
<212> TYPE: PRT
<213> ORGANISM: Oryza sativa

<400> SEQUENCE: 10

```
Met Thr Pro Val Glu Glu Val Asp Leu Ser Ala Val Arg Tyr Gln Ser
 1               5                  10                  15

Pro Ser Leu Gln Ala Pro His Leu Thr Gly Phe Ser Leu Arg Ala Phe
            20                  25                  30

Val Trp Leu Met Glu Ser Pro Leu Phe Gly Arg Leu Leu Thr Ser Val
        35                  40                  45

Leu Lys Ser Gln Asn Asn Ile Thr Arg Met Leu Gln Asp Thr Val Ile
    50                  55                  60

Pro Glu Arg Pro Met Tyr Leu Pro Glu Tyr Pro Gln Glu Pro Glu
65                  70                  75                  80

Gln Gly Val Leu Leu Leu Gly Asp Asp Arg Asp Pro Val Asp Arg Val
                85                  90                  95

Glu Glu Ala Leu His Cys Leu Pro Pro Tyr Asp Pro Ser Leu Arg Trp
            100                 105                 110

Pro Ala Gly Asp Lys Pro Pro Phe Leu Tyr Trp Lys Ile Arg Asp Phe
        115                 120                 125

Ala His Ala Tyr Arg Ser Gly Ile Thr Thr Pro Ser Val Val Ala Glu
    130                 135                 140

His Ile Ile Ala Gly Val Glu Glu Trp Ser Asn Lys Lys Pro Pro Met
145                 150                 155                 160

Pro Met Leu Val Tyr Phe Asn Ala Asp Asp Leu Arg Lys Gln Ala Glu
                165                 170                 175

Ala Ser Thr Lys Arg Phe Gln Gln Gly Asn Pro Ile Ser Ile Leu Asp
            180                 185                 190

Gly Ile Phe Ile Ala Ile Lys Asp Asp Ile Asp Cys Phe Pro Tyr Pro
        195                 200                 205

Ser Lys Gly Ala Thr Thr Phe Phe Asp Lys Ile Arg Ser Val Glu Lys
    210                 215                 220

Asp Ala Val Cys Val Ala Arg Leu Arg Lys Cys Gly Val Leu Phe Ile
225                 230                 235                 240

Gly Lys Ala Asn Met His Glu Leu Gly Leu Gly Val Thr Gly Asn Asn
                245                 250                 255

Pro Asn Tyr Gly Thr Ala Arg Asn Pro His Ser Ile Asp Arg Tyr Thr
            260                 265                 270

Gly Gly Ser Ser Ser Gly Pro Ala Ala Leu Val Ser Ser Gly Leu Cys
        275                 280                 285
```

```
Ser Ala Ala Ile Gly Thr Asp Gly Gly Gly Ser Val Arg Ile Pro Ser
290                 295                 300
Ser Leu Cys Gly Ile Ile Gly Leu Lys Thr Thr Tyr Gly Arg Thr Asp
305                 310                 315                 320
Met Thr Gly Ala Leu Cys Asp Cys Gly Thr Val Glu Val Ala Ser Pro
                325                 330                 335
Leu Ala Ala Ser Val Glu Asp Ala Leu Leu Val Tyr Ser Ala Ile Ala
                340                 345                 350
Gly Ser Arg Pro Met Asp Lys Leu Thr Leu Arg Pro Ser Pro Leu Cys
                355                 360                 365
Val Pro Asn Leu Val Ser Pro Asp Asn Asn Ile Leu Gly Ser Val
370                 375                 380
Lys Ile Gly Lys Tyr Thr Glu Trp Phe His Asp Val Ser Asp Arg Asp
385                 390                 395                 400
Ile Ser Asn Thr Cys Glu Asp Ala Leu Asn Leu Leu Cys Ser Ser Phe
                405                 410                 415
Gly Cys Gln Ile Glu Glu Ile Ile Leu Pro Glu Leu Glu Met Arg
                420                 425                 430
Thr Ala His Val Val Ser Ile Gly Thr Glu Ser Phe Cys Asp Leu Asn
                435                 440                 445
Pro His Tyr Arg Ala Gly Lys Arg Thr Glu Phe Thr Leu Asp Thr Arg
450                 455                 460
Thr Ser Leu Ala Leu Phe Gly Ser Phe Thr Ser Thr Asp Tyr Val Ala
465                 470                 475                 480
Ser Gln Arg Ile Ser Ile Thr Ala Pro Glu Ile Pro Gln Ser Ser Leu
                485                 490                 495
Lys Leu Gly Glu Ser Asn Tyr Val Val Ser Ala Tyr Leu Met Arg Phe
                500                 505                 510
Val Ile Ala Gly Asn Leu Leu Gly Leu Pro Ala Ile Thr Val Pro Val
                515                 520                 525
Gly His Asp Lys Gln Gly Leu Pro Ile Gly Leu Gln Leu Ile Gly Arg
                530                 535                 540
Pro Trp Gly Glu Ala Ser Leu Leu Arg Val Ala Ser Ala Ile Glu Glu
545                 550                 555                 560
Leu Cys Leu Gln Lys Arg Lys Arg Pro Ser Ala Phe His Asp Ile Leu
                565                 570                 575
Asn Ala
```

<210> SEQ ID NO 11
<211> LENGTH: 1803
<212> TYPE: DNA
<213> ORGANISM: Oryza sativa

<400> SEQUENCE: 11

| | | |
|---|---|---|
| atgacgccgg tggaggaggt ggacctgtcg gcggtgaggt accagtcgcc gtcgctgcag | 60 |
| gcgccgcacc tcaccggctt ctctctcagg gccttcgtct ggctcatgga gtcgccccta | 120 |
| ttcggccgcc tcctcaccct cgtcctcaag tcgcagaaca acatcacaag gatgctgcag | 180 |
| gacacggtga tccccgagcg ccccatgtac ctccccgagt accgccgca ggagccggag | 240 |
| caaggagttt tgcttctggg ggatgacagg gaccctgtgg acagagttga ggaagcactt | 300 |
| cactgcctcc cgccctatga tccgtctctg cgttggccgg ccggggacaa acccccttc | 360 |
| ctctactgga gatccgtgga ttttgcgcat gcgtaccgct ccgggatcac aacccgtct | 420 |
| gttgttgcgg agcatatcat tgccggtgtg aagagtggga gcaacaagaa gcctcccatg | 480 |

```
cctatgttgg tttattttaa cgcagatgat ctaaggaaac aagctgaagc ttccacaaag      540
agatttcagc aaggaaaccc aatttccatc ttggacggga tctttatcgc cattaaggat      600
gacattgact gcttcccata tccatcaaag ggtgctacta cattttttcga caaaattcgc     660 tctgtggaga agacgcagt ttgtgttgct cgtttgcgga aatgtggagt gttattcatt       720
gggaaagcta atatgcatga gctaggcctt ggagtaactg gaaacaatcc aaactatgga      780
acagcaagaa atccacattc aattgataga tatactggtg gttcttcatc aggtccagct      840
gcactagtct catcagggtt atgctcagca gcaattggaa cagatggtgg aggttctgtt      900
aggataccat cttctctatg tggcattatt ggtttgaaga caacctacgg acggacagat      960
atgactgggg cactttgtga ttgtgggacc gttgaagttg cttctcctct agcagcttca     1020
gtggaggatg ctttgctagt gtattctgca atagcaggct ctaggcctat ggataagctt     1080
accctgagac catcaccgct ctgtgtccct aatttggtgt ctcctgacaa caacaatata     1140
ctgggatcgg tgaaaatagg aaaatatact gagtggtttc atgatgtctc cgatcgtgat     1200
atctctaata catgtgagga tgcacttaac cttctttgca gcagcttcgg atgtcaaata     1260
gaagaaataa tactgccaga acttgaggag atgcgtactg cccatgttgt ctcaattggc     1320
acagaatcat tctgtgattt gaatcctcat tacagagcag gaaaacgaac tgaatttacg     1380
ttagacactc gaacaagttt ggcactttttt ggatcattca cttcgactga ctatgttgct     1440
tctcaacgaa taaggagaag gataatgtac tatcacaatg aagctttcaa gaaggttgat     1500
gtcatagcaa ctcctacaac tggcatcact gctccagaaa taccacaaag ttctctgaag     1560
ttaggagagt ccaattacgt tgtgtcagct tacctgatgc gattcgtgat agctggcaat     1620
cttcttggtt tgcccgcgat aactgtacct gttggtcatg ataagcaagg gcttcctata     1680
ggcttgcaac tgataggtcg accatggggc gaggctagct tattaagggt ggcttctgca     1740
atcgaggagc tctgtctgca gaagcggaaa cggccatctg catttcatga catcctgaac     1800
gct                                                                   1803
```

<210> SEQ ID NO 12
<211> LENGTH: 601
<212> TYPE: PRT
<213> ORGANISM: Oryza sativa

<400> SEQUENCE: 12

```
Met Thr Pro Val Glu Glu Val Asp Leu Ser Ala Val Arg Tyr Gln Ser
  1               5                  10                  15

Pro Ser Leu Gln Ala Pro His Leu Thr Gly Phe Ser Leu Arg Ala Phe
             20                  25                  30

Val Trp Leu Met Glu Ser Pro Leu Phe Gly Arg Leu Leu Thr Ser Val
         35                  40                  45

Leu Lys Ser Gln Asn Asn Ile Thr Arg Met Leu Gln Asp Thr Val Ile
     50                  55                  60

Pro Glu Arg Pro Met Tyr Leu Pro Glu Tyr Pro Gln Glu Pro Glu
 65                  70                  75                  80

Gln Gly Val Leu Leu Leu Gly Asp Asp Arg Asp Pro Val Asp Arg Val
                 85                  90                  95

Glu Glu Ala Leu His Cys Leu Pro Pro Tyr Asp Pro Ser Leu Arg Trp
            100                 105                 110

Pro Ala Gly Asp Lys Pro Pro Phe Leu Tyr Trp Lys Ile Arg Asp Phe
        115                 120                 125
```

-continued

```
Ala His Ala Tyr Arg Ser Gly Ile Thr Thr Pro Ser Val Val Ala Glu
    130                 135                 140
His Ile Ile Ala Gly Val Glu Glu Trp Ser Asn Lys Lys Pro Pro Met
145                 150                 155                 160
Pro Met Leu Val Tyr Phe Asn Ala Asp Asp Leu Arg Lys Gln Ala Glu
                165                 170                 175
Ala Ser Thr Lys Arg Phe Gln Gln Gly Asn Pro Ile Ser Ile Leu Asp
            180                 185                 190
Gly Ile Phe Ile Ala Ile Lys Asp Asp Ile Asp Cys Phe Pro Tyr Pro
        195                 200                 205
Ser Lys Gly Ala Thr Thr Phe Phe Asp Lys Ile Arg Ser Val Glu Lys
    210                 215                 220
Asp Ala Val Cys Val Ala Arg Leu Arg Lys Cys Gly Val Leu Phe Ile
225                 230                 235                 240
Gly Lys Ala Asn Met His Glu Leu Gly Leu Gly Val Thr Gly Asn Asn
                245                 250                 255
Pro Asn Tyr Gly Thr Ala Arg Asn Pro His Ser Ile Asp Arg Tyr Thr
                260                 265                 270
Gly Gly Ser Ser Ser Gly Pro Ala Ala Leu Val Ser Ser Gly Leu Cys
        275                 280                 285
Ser Ala Ala Ile Gly Thr Asp Gly Gly Gly Ser Val Arg Ile Pro Ser
    290                 295                 300
Ser Leu Cys Gly Ile Ile Gly Leu Lys Thr Thr Tyr Gly Arg Thr Asp
305                 310                 315                 320
Met Thr Gly Ala Leu Cys Asp Cys Gly Thr Val Glu Val Ala Ser Pro
                325                 330                 335
Leu Ala Ala Ser Val Glu Asp Ala Leu Leu Val Tyr Ser Ala Ile Ala
            340                 345                 350
Gly Ser Arg Pro Met Asp Lys Leu Thr Leu Arg Pro Ser Pro Leu Cys
        355                 360                 365
Val Pro Asn Leu Val Ser Pro Asp Asn Asn Ile Leu Gly Ser Val
    370                 375                 380
Lys Ile Gly Lys Tyr Thr Glu Trp Phe His Asp Val Ser Asp Arg Asp
385                 390                 395                 400
Ile Ser Asn Thr Cys Glu Asp Ala Leu Asn Leu Leu Cys Ser Ser Phe
                405                 410                 415
Gly Cys Gln Ile Glu Glu Ile Ile Leu Pro Glu Leu Glu Glu Met Arg
            420                 425                 430
Thr Ala His Val Val Ser Ile Gly Thr Glu Ser Phe Cys Asp Leu Asn
        435                 440                 445
Pro His Tyr Arg Ala Gly Lys Arg Thr Glu Phe Thr Leu Asp Thr Arg
    450                 455                 460
Thr Ser Leu Ala Leu Phe Gly Ser Phe Thr Ser Thr Asp Tyr Val Ala
465                 470                 475                 480
Ser Gln Arg Ile Arg Arg Ile Met Tyr Tyr His Asn Glu Ala Phe
                485                 490                 495
Lys Lys Val Asp Val Ile Ala Thr Pro Thr Thr Gly Ile Thr Ala Pro
            500                 505                 510
Glu Ile Pro Gln Ser Ser Leu Lys Leu Gly Glu Ser Asn Tyr Val Val
        515                 520                 525
Ser Ala Tyr Leu Met Arg Phe Val Ile Ala Gly Asn Leu Leu Gly Leu
    530                 535                 540
Pro Ala Ile Thr Val Pro Val Gly His Asp Lys Gln Gly Leu Pro Ile
```

```
                545                 550                 555                 560
Gly Leu Gln Leu Ile Gly Arg Pro Trp Gly Glu Ala Ser Leu Leu Arg
                    565                 570                 575
Val Ala Ser Ala Ile Glu Glu Leu Cys Leu Gln Lys Arg Lys Arg Pro
                580                 585                 590
Ser Ala Phe His Asp Ile Leu Asn Ala
        595                 600

<210> SEQ ID NO 13
<211> LENGTH: 2336
<212> TYPE: DNA
<213> ORGANISM: Medicago truncatula

<400> SEQUENCE: 13
aattcggcac gaggcttcaa tttgcatttc caatttcaac ttccttttc gctaactaca      60 acaattccaa tctgtaacag ttagttaagc tcgcgcgttt tatttttttt tatttctgaa    120
gatggggaag aagcgtgtaa tggtgccggc gaaggacgta gatttgtctt caatcaaata    180
cgaacctgaa attgttcaag ctccacattt gactggcttt tggtttcgat tttttgtgag    240
gttaattgaa gctccattga taggtccttt cttgttgact atgttgaaga aggaaaataa    300
aattgatcag ttattgcgga acactgtgtt cccgaggaa cccatgttta aacctgaata    360
tccacctcaa gaaaaggaac acagtgttgt tgagcttgac gaagacggga gacctgaagg    420
cagagttgag tctgccttga actgtcttcc acattatgat cctgctaaat tatgggaaaa    480
ttcatctgca accttcggt actggaaaat acgtgactat gcttatgctt atcagtctag    540
aaaagtaacc ccatctatgg ttgctgagag catcatctca atgatagagg agaatggaat    600
agataaacct ccgacaccac tattgttatc ttttgatgct gcagaagtcc gaaagcaggc    660
agcagcatct actcagaggt ttgaatcagg aaatccatta tcaatattgg atggaatttt    720
cattgctatc aaagatgaca tagattgcca tcctcacccg tctactggtg atcaacatg    780 gatgcatgag gtacgtgatg taagaagga tgctgtctgt gtttcaagac ttcgtagctg    840
tggtgtcata ttcataggga agacaaatat gcatgagttt ggcatgggta acaggaaa     900 taattctaat tacggaactg caagaaatcc tcatgcacct gataggtata ctggtggatc    960
ctcttcaggt ccagctgcaa ttgttgcttc cggactatgt tctgctgcac ttggcaccga   1020
tggtggaagt tcggtacgta ttccttcttc cctatgtggt gtggtaggat gaagataaa   1080 ttacgggcga acaagcatgg agggtccctt gtgtgattct gggacagtgg aagttattgg   1140
acccattgct tcaacagtag aggatgcgat gctagtgtat gcggcaatgt gggtgcatc    1200 acctgcaaat agaatcagta tgaaaccgtc aacaccttgt ctgccaactc tgtcgtctga   1260
tgatgataca gatgctttga gatcattaag aatagggatt tatacaccgt ggtttaataa   1320
tgtccattca actgaagtct ctgataaatg tgaggatgcc ttaatctgc tgtcaaaggc    1380 acatggttgt gaagtggtag aagttgttat accagagatt gtggagatgc gaactgccca   1440 tcttgttttcc attggctctg aatgcttaag ttcactgaat cctgatattg aagacgggaa   1500
aggtgtaaaa ttgtcatatg atactcgcac aagtttggca ctttccagt catttaccgc   1560 agcagattat gttgcagctc aatgtattag acgaaggatt atgcattact tcatggagat   1620
tttcaagaaa gttgatgtca tagtgactcc aacaactggt atgacagctc ccagaatacc   1680
tccaagtgcc cttaaaagtg gtgaaacaga tatgccgact acaggttacc tcatgcggtt   1740
cgttgttcca gcaaatcttt tgggactccc tgccatttct gtcccggtgg gttacgataa   1800
```

-continued

```
agaaggactt ccaataggtt tgcaagtaat tggccgacca tgggcagagg ctactatttt    1860
gcgtgtagca gctgcagtag agaaactctg cggggagtca agagaagac ctgtgacata     1920 ctacgatgtt ctgggggcta actgaagctt aaaatactct tgtgggtcat taatctgtgg   1980
ctgaaaactt ctagcgttat ttggagatcg ctatcctttt aacaggattt acggtttggc    2040
aaacttcctt gcaaataata tctacagaca agattgtgtt aataacctct acagtcataa    2100
aatattgttt agaaaataat ggatgaacac actatcaaaa tgcagaaggg gaagtataca    2160
gtcaagatta tatttcattt cagattaatt tttttgttaa ttgttatccc ctcaaatatt    2220
tttcatttcc tatgatacat ttgcagttac tactgttcta taattataa acagattaat    2280 gtcatccatt ttttaacgtt atttgaagta gttttaataa aaaaaaaaaa aaaaaa        2336
```

<210> SEQ ID NO 14
<211> LENGTH: 607
<212> TYPE: PRT
<213> ORGANISM: Medicago truncatula

<400> SEQUENCE: 14

```
Met Gly Lys Lys Arg Val Met Val Pro Ala Lys Asp Val Asp Leu Ser
 1               5                  10                  15

Ser Ile Lys Tyr Glu Pro Glu Ile Val Gln Ala Pro His Leu Thr Gly
            20                  25                  30

Phe Trp Phe Arg Phe Val Arg Leu Ile Glu Ala Pro Leu Ile Gly
        35                  40                  45

Pro Phe Leu Leu Thr Met Leu Lys Lys Glu Asn Lys Ile Asp Gln Leu
    50                  55                  60

Leu Arg Asn Thr Val Phe Pro Glu Pro Met Phe Lys Pro Glu Tyr
65                  70                  75                  80

Pro Pro Gln Glu Lys Glu His Ser Val Val Glu Leu Asp Glu Asp Gly
                85                  90                  95

Arg Pro Glu Gly Arg Val Glu Ser Ala Leu Asn Cys Leu Pro His Tyr
            100                 105                 110

Asp Pro Ala Lys Leu Trp Glu Asn Ser Ser Ala Thr Phe Arg Tyr Trp
        115                 120                 125

Lys Ile Arg Asp Tyr Ala Tyr Ala Tyr Gln Ser Arg Lys Val Thr Pro
    130                 135                 140

Ser Met Val Ala Glu Ser Ile Ile Ser Met Ile Glu Glu Asn Gly Ile
145                 150                 155                 160

Asp Lys Pro Pro Thr Pro Leu Leu Leu Ser Phe Asp Ala Ala Glu Val
                165                 170                 175

Arg Lys Gln Ala Ala Ser Thr Gln Arg Phe Glu Ser Gly Asn Pro
            180                 185                 190

Leu Ser Ile Leu Asp Gly Ile Phe Ile Ala Ile Lys Asp Asp Ile Asp
        195                 200                 205

Cys His Pro His Pro Ser Thr Gly Gly Ser Thr Trp Met His Glu Val
    210                 215                 220

Arg Asp Val Lys Lys Asp Ala Val Cys Val Ser Arg Leu Arg Ser Cys
225                 230                 235                 240

Gly Val Ile Phe Ile Gly Lys Thr Asn Met His Glu Phe Gly Met Gly
                245                 250                 255

Thr Thr Gly Asn Asn Ser Asn Tyr Gly Thr Ala Arg Asn Pro His Ala
            260                 265                 270

Pro Asp Arg Tyr Thr Gly Gly Ser Ser Ser Gly Pro Ala Ala Ile Val
        275                 280                 285
```

```
Ala Ser Gly Leu Cys Ser Ala Ala Leu Gly Thr Asp Gly Gly Ser Ser
        290                 295                 300
Val Arg Ile Pro Ser Ser Leu Cys Gly Val Val Gly Leu Lys Ile Asn
305                 310                 315                 320
Tyr Gly Arg Thr Ser Met Glu Gly Ser Leu Cys Asp Ser Gly Thr Val
                325                 330                 335
Glu Val Ile Gly Pro Ile Ala Ser Thr Val Glu Asp Ala Met Leu Val
            340                 345                 350
Tyr Ala Ala Met Leu Gly Ala Ser Pro Ala Asn Arg Ile Ser Met Lys
        355                 360                 365
Pro Ser Thr Pro Cys Leu Pro Thr Leu Ser Ser Asp Asp Thr Asp
    370                 375                 380
Ala Leu Arg Ser Leu Arg Ile Gly Ile Tyr Thr Pro Trp Phe Asn Asn
385                 390                 395                 400
Val His Ser Thr Glu Val Ser Asp Lys Cys Glu Asp Ala Leu Asn Leu
                405                 410                 415
Leu Ser Lys Ala His Gly Cys Glu Val Val Glu Val Ile Pro Glu
            420                 425                 430
Ile Val Glu Met Arg Thr Ala His Leu Val Ser Ile Gly Ser Glu Cys
        435                 440                 445
Leu Ser Ser Leu Asn Pro Asp Ile Glu Asp Gly Lys Gly Val Lys Leu
    450                 455                 460
Ser Tyr Asp Thr Arg Thr Ser Leu Ala Leu Phe Gln Ser Phe Thr Ala
465                 470                 475                 480
Ala Asp Tyr Val Ala Ala Gln Cys Ile Arg Arg Ile Met His Tyr
                485                 490                 495
Phe Met Glu Ile Phe Lys Lys Val Asp Val Ile Val Thr Pro Thr Thr
            500                 505                 510
Gly Met Thr Ala Pro Arg Ile Pro Pro Ser Ala Leu Lys Ser Gly Glu
        515                 520                 525
Thr Asp Met Pro Thr Thr Gly Tyr Leu Met Arg Phe Val Val Pro Ala
    530                 535                 540
Asn Leu Leu Gly Leu Pro Ala Ile Ser Val Pro Val Gly Tyr Asp Lys
545                 550                 555                 560
Glu Gly Leu Pro Ile Gly Leu Gln Val Ile Gly Arg Pro Trp Ala Glu
                565                 570                 575
Ala Thr Ile Leu Arg Val Ala Ala Val Glu Lys Leu Cys Gly Glu
            580                 585                 590
Ser Lys Arg Arg Pro Val Thr Tyr Tyr Asp Val Leu Gly Ala Asn
        595                 600                 605

<210> SEQ ID NO 15
<211> LENGTH: 2145
<212> TYPE: DNA
<213> ORGANISM: Arabidopsis thaliana

<400> SEQUENCE: 15
gaacatataa cattcaagtt cccaacaact tcaccgctca tctccgcacg gctttcttca     60
tttagtaatc cttcgccgga tcggatcatc gtttctcaga ttcctctttt taagtttctt    120
ctttcagatg ggtaagtatc aggtcatgaa acgtgcaagt gaggttgatc tttctactgt    180
caaatataaa gctgaaacca tgaaagctcc tcatttgact ggcctttcct tcaagttgtt    240
cgttaatttg cttgaagcac cactttatagg ctctttgatt gttgattatt tgaagaaaga    300
```

```
caatggcatg acaaagattt ttcgcaacac agttatacca gaagagccca tgtttagacc    360
ggagttccca tctcaagaac cggagcatga tgttgtcatt gttggcgaag atgaaagtcc    420
tatagacaga ttggaaacag ccttgaaatg tcttcctcag tatgatcctt ctcgtagctt    480
gcatgcagat ccagtgtcat ctttccggta ctggaagatt cgtgattatg catatgccta    540
tagatctaag ctgacaactc cattgcaggt agcaaaaaga ataatctcaa tcatagagga    600
gtttggctat gacaagcctc caacaccatt tttgattaga tttgatgcca atgaagtcat    660
aaagcaagct gaagcttcta cacggaggtt tgaacaagga atccaatat ctgttttgga     720
tggaatattt gtgacaatca aggacgatat tgattgttta ccccatccga caaatggtgg    780
aacaacatgg ctgcatgagg atcgttctgt ggagaaggat tcagctgttg tttcaaaact    840
gcgttcttgt ggtgcaatct tacttggcaa ggcaaatatg catgagttag catggggac    900
caccgggaac aattcaaatt acggaaccac aagaaacccg catgatccta aaggtacac     960
gggcggatct tcctcaggtt cagcagctat tgtagccgct ggactatgtt cagctgctct   1020
aggaacagat ggtggaggtt ccgttcgcat tccttcagca cttttgtggta taacgggact  1080
gaagacaaca tatggtcgga cagatatgac agggtcatta tgtgaaggtg aacagtgga   1140
aataattggt ccacttgctt catctctgga agatgccttc ttggtgtatg ctgcaatctt   1200
gggttcttca tctgctgata gatataattt gaaaccgagc ccaccgtgtt ttccaaagtt   1260
attgtctcac aacggaagca atgcaatagg atctctacga ctagggaaat atacaaagtg   1320
gtttaatgat gtcagttcaa gtgacatctc tgacaaatgc gaagacatcc ttaagctcct   1380
atcaaacaat cacggttgca agtggtgga gatagtggtt cctgaactgg aagagatgcg   1440
tgcagcccat gttatttcga ttgggtctcc aacactgtct tctcttactc cctactgtga   1500
agctgggaaa aattcaaaac taagttatga cactcgtacc agctttgcaa ttttccgttc   1560
attctctgct tcagactata tcgctgctca atgtcttagg cgaagattga tggagtatca   1620
cttgaatatc ttcaaagacg ttgatgtcat tgtgacccct acaactggaa tgacagctcc   1680
agtgatacct cctgatgctc tcaaaaatgg agaaaccaat attcaagtga caactgattt   1740
aatgcgcttc gttctagctg caaatctcct cggcttccct gccatatcag tcccggttgg   1800
ttatgataaa gagggcttc ctataggatt acaaataatg ggaagaccctt gggccgaagc    1860
taccgtcctt ggtttagctg ccgcagtcga ggaactggct ccagttacca gaaacctgc    1920
aatcttttat gatattctca atacaaactg aattcataag gatcttccac agaactgaaa   1980
aggcaaggat tgtctctggc tgcggaatat tatttatgtt tacattatat aaggttaata   2040
tgtcaattga tctacaaatc gacgattatt gtgctataaa ccgtgttgga atttcttacg   2100
tcgactatga ttaattttaa aagatgtgaa ttagtcttga gcatg                   2145
```

<210> SEQ ID NO 16
<211> LENGTH: 1392
<212> TYPE: DNA
<213> ORGANISM: Hordeum vulgare
<220> FEATURE:
<221> NAME/KEY: modified_base
<222> LOCATION: (21)..(22)
<223> OTHER INFORMATION: N = a, c, g or t/u

<400> SEQUENCE: 16

```
actgcctccc tacccatcaa nnagtgccac cacattttt gacgaaatcc gccctgtgga      60
gaaagacgct gtcgccgttt ctcgtttacg gaaatgtgga gtgatcttta ttgggaaagc    120
aaatatgcac gagctaggcc ttgggtcac tggaaacaat ccaaactatg ggacagtaag    180
```

-continued

```
aaatccacat tcaatcgata gatatactgg tggttcttca tctggtccag ctgcacttgt      240
ctcatcaggg ttatgttcag gagctattgg aacagatggc ggaggctcag ttcgaatacc      300
atcctctcta tgtggaatag ttggtttgaa gacaacatac gggcgcacag atatgactgg      360
ggtcgtttgt gatgctggga ctgttgaagt tgcttcacct cttacatcat cagtggagga      420
ttctatgcta ttgtattctg cactagcagg ctctagaccc acggacaaac ttactctgag      480
accttccccg ctgtgtgttc ctaacttggt gtcctccgag aacagcaaca tcctgcaatc      540
ggtgaaagtg ggaaaatata cagagtggtt tcatgatgtc cctgataatg aggtctcaaa      600
tacatgtgaa gatgcactta acctcctatg cagcaccttc ggatgtcaga tagaagagat      660
aatcttacca gagcttgagg agatgcgtac agcccatctt gtctctattg gctcagaagc      720
attctccgac atgaatgctc attaccaagc agggaggcga acggaaatga cgttagatac      780
tcgaacaagt ttggcacttt ttaggtcatt cacttcagca gattatgttg cttctcaatc      840
tctgaggaga aggataatgt actatcacat ggaagctttc aagaaggttg acgtcatagc      900 aaccccctaca accggcatga ccgcgccaaa aataccacca agtgctttaa aaggagagtc      960
tgattatgtt gtgtcagcca agctgatgca attcattttt gccgggaacc ttcttggctt     1020
gcctgccatt actgttcctg ttggtcatga caagcaaggc cttcctatcg gcttgcaact     1080
gataggccgt ccgtggggcg aggctagctt attgagggtg gcttcggcag tagaggagct     1140
ctgcctgaag aaaagaaatc ggccatccac gttttacgac atcctgaaga cctgaaacat     1200
catcagtata ccatactatc aatagtatgt gagaggtttg tcatttgtca ggactcagga     1260
tagacacaac aaaccttctc cagtttacaa aaaactgaga aaatatttt accagaaaca      1320 ttgtagcagc aataagcaag tgaggtacaa cagtatatat ataaaaagaa ccgtttggac      1380
atttgggata tc                                                         1392
```

<210> SEQ ID NO 17
<211> LENGTH: 740
<212> TYPE: DNA
<213> ORGANISM: Gossypium hirsutum

<400> SEQUENCE: 17

```
tcccccctgt tttccagatt tgtcatcact tgagaatgca aacactttgg gatcattacg       60
actggggaag tatacagagt ggtttaatga tgtgcattca actgatatct cggatgtctg      120
tgaagatgtt cttaagcttt tgtcaaaaag ccatggatgc gaaacaatag agatagtaat      180
accagaacta catgagatgc gcactgctca tgttgtttca attggatcgg aaacacaatg      240
ctcgttaaat ccggattgtg aagacgggaa aggtgtgaaa ttgacgtatg atactcgcat      300
aagtatggca cttttctgat cattcactgc atcggattat gtagctgccc aatgtcttag      360
acgaaggata atgcaccatc acatggagat cttcaagaag gttgatgtca tagtgacccc      420
aacaactggc atgacagcac caaaaatacc atctagtgct ttgaaagatg gagagacaga      480
tatgcaggtt acagcttatc tcatgaggtt cattattgcc ggtaatcttc ttggtcttcc      540
tgccattacc gtccctgttg gttatgacaa acaaggcctt ccgataggct tgcagctcat      600
aggccgtccg tggggtgaag cgacaatttt acatttggct tctgcagttg aagaactttg      660
tgctaaatcc aggaagaaaa ctgcatcctt ctatgacatt ttaaatatca aataaaaagc      720
cttttacagc tccaagatgc                                                  740
```

<210> SEQ ID NO 18

<211> LENGTH: 1596
<212> TYPE: DNA
<213> ORGANISM: Vitis vinifera

<400> SEQUENCE: 18

| | | |
|---|---|---|
| agctgcagct tctacacaaa ggtttcagga aggaaatccc ttatctatct tggacggtat | 60 |
| ttttgtggca atcaaggatg atatagattg cttacctcat ccttctaagg gtgcaacaat | 120 |
| atggatgcac gaggttcgtc ctgttgaaaa ggatgcagtt agcgtttcaa gactgcgtag | 180 |
| ctgtggtgtt attttttgtgg ggaaggcaaa tatgcatgag ttgggcctgg gaaccagtgg | 240 |
| aaataatcca aattatggaa caacaagaaa cccccatgca ccagaaaggt atactggtgg | 300 |
| atcttcctca ggcccagcag cacttgtagc ttccggacta tgttcagctg cactgggaac | 360 |
| tgatggtgga ggttcagttc gtattccttc ttcactttgt ggtgtagtgg gcttgaaaac | 420 |
| aacatatgga cggacttcta tgatagggtc aatatgtgat tctgggactg tggaaattat | 480 |
| aggccccatt gcatcaatgg ttgaggatgt catgctagtg tatgcagcca tcttgggctc | 540 |
| ctctcctgct gatagaatct gttcaaaacc ggcacctcct tgtttgccaa atttatcatc | 600 |
| atctgaaagc ttgaatgtga tgggaacact gcgcctgggg aagtacacac agtggtttaa | 660 |
| tgatgtatac tcaactgata tctctgataa gtgtgaggat gtgctcaata tgctatccaa | 720 |
| aaaccatggg tgcaaagtaa cagagattat aataccagaa ctgaacgaga tgcgcaatgc | 780 |
| tcatattgtt tcaattggct ctgaatcagt atcttcattg attcctcatt gttatgatgg | 840 |
| gaaaatatcg aaaatgacat tggatacatg cactaatctg gcactattta ggacattcgc | 900 |
| tgcatcagat tatgttgctg cccaatgtct gaggagaagg ctaatgtact accacatgga | 960 |
| gattttcaag aatgttgata tcatagtgac cccaacaact ggtatgacgg cacctataat | 1020 |
| atcccctagt gctcttaaat tggggaatc aaatcttcag gttggaggtt acctcatgcg | 1080 |
| gtttgttgta gccgcaaatc ttcttggtct tcctgccatt tctgtccctg ttggttatga | 1140 |
| taaacaagga cttccaatag gcttacaact cataggccgg ccatggggcg aagcttcaat | 1200 |
| tttgcgattg gcttctgcag tggaggaact ctgtggtgag cctaagaaga agcctgcaca | 1260 |
| attttatgat atcttgaaag tgaaatagga atctgcaaca cacttttgct gcctatgaca | 1320 |
| attggtttct ccattacagc tccctctctg catactttga aacgtctgtt attgcttaat | 1380 |
| aaatgttgtc ataagaagct actatgctta tttaaacaat acctgtttga aacaatcact | 1440 |
| tgtttattat cttatttcca ttgggatggt taaaccattt ggatttaata tatgtatata | 1500 |
| cattgggata ctctacagaa attgaaaaaa aatgtttcaa gtgtatgaat tgatggaggg | 1560 |
| tatagtatat taaagaccct tctggataac tttcct | 1596 |

<210> SEQ ID NO 19
<211> LENGTH: 604
<212> TYPE: DNA
<213> ORGANISM: Zea mays
<220> FEATURE:
<221> NAME/KEY: modified_base
<222> LOCATION: (54)
<223> OTHER INFORMATION: N = a, c, g or t/u

<400> SEQUENCE: 19

| | | |
|---|---|---|
| tgcaactgat tatgtggctt ctcaaagcat aaggaggagg ataatgcatt atcncatgga | 60 |
| agctttcaag aaggtcaatg tcatagcaac tcctacaact ggcattactg ctccaaaaat | 120 |
| acctccaagt gctctgaagt caggagagtc agattatgtt gtgtcagctt acttgatgcg | 180 |
| attcatcata gcagggaacc ttcttggtct cccagcaata actgtgcctg ttggtcatga | 240 |

-continued

```
caagcagggg cttcctatag gtttgcaact gataggtcgt ccatgggcg aggcaagctt      300 actgagggtg gcttctgcag tggaggagct gtgtctgaag aaacggaagc gaccctctgc      360
attttatgac attttgaagg cctgaatcgt cgttgtatac ataatcacgg tgttttgcga      420
tgacatgagt atgtatgatg aaaagtgtgg gtgagagtga ctgaggagag tttcatgtcc      480
tcaagttgta aaatactgtc atcgtcacca tgatgctgat gtcattagag ctgaacgtgc      540
aaatagcata taggcgtgaa tgttgtcgtg acctttcttt ctacctgctc tcaaggtttt      600
ttct                                                                   604

<210> SEQ ID NO 20
<211> LENGTH: 1297
<212> TYPE: DNA
<213> ORGANISM: Solanum tuberosum

<400> SEQUENCE: 20
gattatgtga tgatggaaca gtggcaatta ttggaccaat gctacaaca gttgaggaca       60 ccatactcgt gtatgcagca attttggggt cctctcctgc tgatagaatc tctttgagac      120
cggtaaccat cccaaaaggc ttattcatca ccacttttct taaactctgt atttcttttg      180
actgttctgc tttcttcctt ttcttcattg taatactttg taaaagtacc ttctggtaaa      240
caggataaac ctgaaacatc atgtacatgt ttagaacatc taaaaaccat gttcttactt      300
ttaatctcac cagcagactc tagattcatt aagatatcac attcatctta ttgattttgg      360
acatcatggt ggatcaaacg ttctgtttct gtaatttatc atctccctct atttctttca      420
gtccctcccc tgtgtaccta atttctcttc acaagagagc ttgcaatctg tggaatcgct      480
gcgccttgga aaatatacag agtggtttaa tgatgtcttc tcaactgata tatctgacaa      540
gtgcgggaat gttctcagtc ggctatcaga aaagcatgga tgcgaaacgg tagaaattgt      600
aataccagag ttgcatgaga tgcgcttagc tcatgttgtt tctattggat ctgaagcatt      660
atgcgcactg aatccagact gttatgatgg gaaggagag agattgacat atgatactcg      720
caccaatctg gcacttttc gttcaattac agcagcagac tatgttgctg ctcagcggct      780
taggcggagg ttaatgtatt tccatatgga gattttcaag agggtggata tcattgtgac      840
accaacgact ggcatgacag cacccataat tccaccaggt gctcttaaag ttggggagac      900
taatttgcaa gttacaggaa atcttatgcg gttcattata acagcaaatc ttctgggact      960
tcctgcagtt actgtccctg ttggttatga caagcaaggg cttcccatag gtatacaact     1020
cattggccga ccctggtgtg aagcttccat tttgcgcttg gctgctgcaa ttgaggaaac     1080
ttgtgctgaa cccaagaaga agccactgca atattatgac attctgaaag gaactagaa      1140 attaaaacac ttatgcgtgc aggtaaacag taatgtgaat catgaagctt taagaagatg     1200
tggattcatt tatcaagatt ttggtgattc atagaaacca tcttgaaaat tgaatgtact     1260
gagtttgagg taccacttta tgaaataaaa gctgatc                              1297

<210> SEQ ID NO 21
<211> LENGTH: 820
<212> TYPE: DNA
<213> ORGANISM: Sorghum bicolor

<400> SEQUENCE: 21
gcacgaggac gatgcactta aacttctctg cagcactttc ggatgccaaa aggaaaactg      60
aatttacgct ggatactcga acaagtttgg cacttttttgg gtcattcact gcaactgatt     120
```

```
atgtggcttc tcaaagtata aggaggagga taatgcacta tcacatggaa gctttcaaga    180
aggtcgatgt catagtaact cctacaactg gcattactgc accaaaaata cctccaagtg    240
ctctgaagtc aggagagtca gattacgttg tgtcagctta cctaatgcga ttcatcatag    300
cagggaacct tcttggtctc ccagcaataa ctgtgcctgt tggtcatgac aagcagggcc    360
ttcctatagg tttgcaactg ataggccgtc catggggtga ggcaagctta ttgagggtgg    420
cttctgcagt ggaggagctg tgcctgaaga acggaagcg gccctctgca tttatgaca    480 tattgaaagc ctgaaacgtc gttgtatata atcccggtgt cttgtgatgg catgggtgcg    540
aggaagggtg gatgagaaga gtttcatctt ctcaagttgt ctgtaataca aatactgtca    600
tcgtcaccat gatggggatg gctgcagatc acatctgcta taataaggct gatgtagtta    660
gctagagctc agtgtgtact tggtatggat atttagagct caatgcacaa gctgacgtgt    720
ggattcaaca aggcgtgagt gtttttcttt ttacaagtta ggcgtgaatg ttgttgttgt    780
gactcttctt cctacctgct cccaatcttt ttttaaaatt                         820

<210> SEQ ID NO 22
<211> LENGTH: 827
<212> TYPE: DNA
<213> ORGANISM: Glycine max

<400> SEQUENCE: 22
ctctgataaa tgtgatgaag cacttaatct gctgtcaaag gcgcatggtt gtgaaagctt     60
cttgagatgc gaactgccca tgttgttttcc attggctctg aatgcttatg ttcactgaat   120
cctgattgtg aagacgggaa aggtgtaaat ttgacatatg atactcgtac aagtttggca   180
ctttttcggt catttacagc agccgattat gttgcagccc aatgtattag acgaaggagt   240
atgtattacc acctggagat tttcaagaaa gtggatgtca tagtaacacc gaccactggc   300 atgcacagcac ccataatacc tcccagtgct cttaaaagtg gtgaaacaga tatgcagact   360
acagctaacc ttatgcagtt cgttgttcct gcaaatcttt gggattccc tgccatttct    420 gtcccggttg gttacgataa agtaggactt ccaataggtt tgcaaataat gggtcgacca    480
tgggcggaag ctactgtact gcgtgtagcc gctgaagtgg agaaactctg tggtgagtgg    540
aagaaaaaac ccgcgtcgta tatgatgtt ctgaaggcta atgaagcta agatattctt      600 gctggttacg gtttataagt agcctttgct gttttatcat ttggaaatcg ctatccattt    660
agcaaatgct gtgtgtgctt tcatcctcgg tgcatctcat ttctccaaag gatttatgat   720
ttgagaagtt cttaggaaat aaatctgcat agtaataatt aaagacaaaa tcaaaaatta   780
tttagaaaat cacgggcgaa ggtaacttgc tcgtcgtcaa tatgtaa                  827

<210> SEQ ID NO 23
<211> LENGTH: 555
<212> TYPE: DNA
<213> ORGANISM: Glycine max

<400> SEQUENCE: 23
attccttctt ccctttgtgg tgtggtggga tttaagacaa cttacgggcg gacaagcatg     60
gaggggtcat tatgtgattc tgggactgtg gaaattattg gacccattgc ttcaacggtg   120
gaggatgtct tgctagtgta ttctgcaatg ttgggtgcat cacctgcaaa tagaatcagt   180
ttgaaaccgt caccaccttg tttgccaagt ctgtcatcca acgataattc aaatgccttg    240
ggatctttaa gaattggaaa gtacaccccg tggtttaatg atgtgcattc aactgaaatc    300
tctgataaat gtgatgaagc acttaatctg ctgtcaaagg cgcatggttg tgaaatgata    360
```

```
gaaattgtta taccagagct tcttgagatg cgaactgccc atgttgtttc cattggctct    420
gaatgcttat gttcactgaa tcctgattgt gaagacggga aaggtgtaaa tttgacatat    480
gatactcgta caagtttggc acttttttcgg tcatttacag cagccgatta tgttgcagct   540
caatgtatta gacga                                                     555
```

```
<210> SEQ ID NO 24
<211> LENGTH: 1371
<212> TYPE: DNA
<213> ORGANISM: Lycopersicon esculentum

<400> SEQUENCE: 24 aagtttatg ctgacatgac cgggtcatta tgtggtgatg aacagtggc aattattgga      60 ccgattgcta caacagttga ggacaccata cttgtgtatg cagcaatttt ggggtcctct   120
cccgctgata gaatctcttt gagaccgtcc ctcccttgtg tacctaattt ctcttcacaa   180
gagagcttgc aatctgtgga atcgctgcgc cttggaaaat atacagagtg gtttaatgat   240
gtcttctcaa ttgatatatc tgacaagtgc gggaatgttc tcagtcagct atcagaagag   300
catggatgca gaatcgtaga aattgtaata ccagagttgc atgagatgcg catagctcat   360
gttgtttcta ttggatcgga agcattatgc gcactgaatc cagactgttg tgatgggaag   420
ggagagagat tgacatatga tactcgcacc aatctgacac ttttcgttc atttacagca    480 gcagactatg ttgcttctca gcggcttagg cggaggttaa tgtatttcca tatggagatt   540
ttcaagaggg tggatatcat tgtgacacca acaactggca tgcagcacc cataattcca    600 ccaagtgctc ttaaagttgg ggagactaat atgcaagtta caggaaatct tatgcggttc   660
attataacag caaatcttct gggacttcct gcagttactg tccctgttgg ttatgacaag   720
caagggcttc ccataggtat acaactcatt ggccggccct ggtgtgaagc ttccattttg   780
cgcttggcgg ctgcaattga ggaaacttgt gctgagccca agaagaaacc actgcaatat   840
tatgacattc tgaaagggaa ctagaaatca agcttagcct gcaggagccc ggggtaaaca   900
gtaatgtgga ttatgaagct ttaagaagat gtgaattcat ttatcaagac tttggtgatt   960
catagaaacc accttgaaaa ttgaacgtac tgagtttgcg gtaccacttt atgaaataaa  1020
gctgatgaaa aggttttggc taatcaatac aaccatttgc aatgcaaata gaatccagaa  1080
acaggtgatg cccgcatagt tgcagtgaaa ttgttaaacc ttgtataaca acattatgtt  1140
cctaaacccc acaatatttg atctcgaaag ggagaaaata agaacacgaa tttttaattg  1200
accctgatat cagctgaaaa aaatcatgtt gcataaaccg agacatttc ttggctactc    1260 tgtgtacttg aggacttatt caacagtcaa tgcgagagtt tggaaacatg tagaaactaa  1320
tacttgccac atttttcatt tacatcagag tgagctccta tttactctgt g            1371
```

```
<210> SEQ ID NO 25
<211> LENGTH: 1782
<212> TYPE: DNA
<213> ORGANISM: Triticum aestivum
<220> FEATURE:
<221> NAME/KEY: modified_base
<222> LOCATION: (9)..(14)
<223> OTHER INFORMATION: N = a, c, g or t/u

<400> SEQUENCE: 25
ccctgtggna cagnagttga ggaggcactg agttgcctcg ttccgtatga cccgtcgggg    60
cgtttcacat cgaccgatga gaaaaacccc ttcctctact ggaagatccg cgactttgcg   120
```

| | |
|---|---|
| tatgcgtacc gatctgggat cacgacgccg tcagctgttg cagagcttgt catagcgggc | 180 |
| gtggaggagt ggaacaacaa gaagcctccg atgccaatgc tgatcttttt taaagcggat | 240 |
| gatctcagga agcaagctga tgcttccaca aagagatttg agaaaggaag tccaatttct | 300 |
| gttttggatg aatctttttt cgctgttaag gacgacattg actgcttacc atacccatca | 360 |
| aagagtgcca ccacattttt tgacgaaatc cgccctgtgg agaaagacgc tgttgctgtt | 420 |
| tctcgtttac ggaaatgtgg agtgatcttt attgggaaag caaatatgca cgagctaggc | 480 |
| cttggggtca ctggaaacaa tccaaactat gggacagtaa gaaatccaca ttcagtcgat | 540 |
| aggtatactg gtggttcttc atctggtcca gctgcacttg tctcatcagg ttatgctca | 600 |
| ggagcaattg gaacagacgg cggaggctca gttcgaatac catcctccct atgtggcatt | 660 |
| gttggtttga agacaacatt cggacgcaca gatatgactg gggtcgtttg tgatgctggg | 720 |
| acagttgaag ttgcttcacc tcttacatca tcagtagagg attctgtgct attgtattct | 780 |
| gcactagcag gctctagacc tatggacaaa cttacgctga ccttccct gctgtgtgtt | 840 |
| cctaacttgg tgtcctccga gaatagcaag atcctgcaat cagtgaaagt gggaaaatat | 900 |
| acagagtggt tcatgatgt ccctgataat gaggtctcaa atacatgtga agatgcactt | 960 |
| aacctcctat gcagcacctt tggatgtcag atagaagaga taatcttacc agagcttgag | 1020 |
| gagatgcgta cagcccatct tgtctctatg ggctcagaag cattctcaga catgaatgct | 1080 |
| cattaccaag cagggaggcg aactgaaatg acgttagata ctcgagcaag tttggcactt | 1140 |
| tttaagtcat tcacttcagc agattatgtt gctgctcaat gtctgaggag aaggataatg | 1200 |
| tactatcaca tggaagcttt caagaaggtt gacgtcatag caacccctac aaccggcatg | 1260 |
| accgcgccaa aaataccacc aagtgctctg aaaggagagt ctgattatgt tgtatcagcc | 1320 |
| aagctgatgc aattcatttt tgccgggaac cttcttggct tgcctgccat ttctgttcct | 1380 |
| gttggtcatg acaagcaagg ccttcctatc ggcttgcaac tgataggccg tccgtggggc | 1440 |
| gaggctagct tattgagggt ggcttcggca gtagaggagc tctgcctgaa gagaagaagt | 1500 |
| cggccatcca cattctacga catcctgaag acctgaaaca tcatcagtat gcaatatcaa | 1560 |
| tagtatgtca gaggtttgtc atttgtcagt gactcaggat agacacagca aacccttccc | 1620 |
| cagtttataa aaaactgaga aaataatttt accagagata ttgtagcagc aataagcaag | 1680 |
| tgaggtacag tagtatataa aaaaaatttg tttggacgtt tggggtatat ctgccgtttt | 1740 |
| ttcctgttgt gattcaattg ttcgtaatgt tcttgatctg gc | 1782 |

<210> SEQ ID NO 26
<211> LENGTH: 931
<212> TYPE: DNA
<213> ORGANISM: Saccharum officinarum
<220> FEATURE:
<221> NAME/KEY: modified_base
<222> LOCATION: (906)..(926)
<223> OTHER INFORMATION: N = a, c, g or t/u

<400> SEQUENCE: 26

| | |
|---|---|
| ggtttaatga tgtttctgat catgagatat cgagtacatg tgacgatgca cttaaactac | 60 |
| tctgcagcgc tttcggatgt caaatagaag agataacatt accagagctt gaagagatgc | 120 |
| gtactgccca tgttgtctca attggctcag agtcattctg tgacctgaat cctcattaca | 180 |
| aagcaggaag gaaaactgag tttacgctgg atactcgaac aagtttggca cttttttggt | 240 |
| cgttcactgc aactgattat gtggcatctc aaagtataag gaggaggata atgcactatc | 300 |
| acatggaagc tttcaagaag gtcgatgtca tagcaactcc tacaactggc attactgctc | 360 |

```
caaaaatacc tccaagtgct ctgaagtcag gagagtcaaa ttatgttgtg tcagcttacc    420
tgatgcgatt catcatagca gggaaccttc ttggtctccc agcaataact gtgcctgttg    480
gtcatgacaa gcagggcctt cctataggtt tgcaactgat aggccgtcca tggggtgagg    540
caagcttatt gagggtggct tctgcagtgg aggagctgtg tctgaagaaa cggaagcgac    600
cctctgcatt ttatgacatt ttgaaggcct gaaacgtcgt tgtatataat tccggtgttt    660
tgtcgtgatg gcatgggtgt gattgtgagg aagggtgggt gagagtggct gagaagagtt    720
tcatcttctc aagttgtctg taatacaaat actgtcatcg tcaccatgat atgggatggg    780
gatggccgca gatcacatct gctatgagta agctggtggt cgtagagctc aatgggttta    840
aatccggcgt atgggttcca caaggggtga atcttttaa aattttaaaa aattgttgat     900
tctttnaaga aaaangatg gccgggcggc c                                    931
```